United States Patent [19]

Los et al.

[11] Patent Number: 4,650,514

[45] Date of Patent: Mar. 17, 1987

[54] (2-IMIDAZOLIN-2-YL)THIENO- AND FURO[2,3-B] AND [3,2-B]PYRIDINES AND INTERMEDIATES FOR THE PREPARATION THEREOF, AND USE OF SAID COMPOUNDS AS HERBICIDAL AGENTS

[75] Inventors: Marinus Los, Pennington; David W. Ladner, Hamilton Square; Barringtin Cross, Rocky Hill, all of N.J.

[73] Assignee: American Cyanamid Company, Stamford, Conn.

[21] Appl. No.: 676,133

[22] Filed: Nov. 29, 1984

Related U.S. Application Data

[63] Continuation-in-part of Ser. No. 611,191, May 21, 1984, abandoned, which is a continuation-in-part of Ser. No. 500,219, Jun. 2, 1983, abandoned.

[51] Int. Cl.[4] .............. C07D 491/048; C07D 495/04; A01N 43/08; A01N 43/10
[52] U.S. Cl. .......................................... 71/90; 71/92; 546/114; 546/115; 546/116; 546/80; 546/89; 546/64; 546/10; 546/15

[58] Field of Search ................ 546/114–116, 546/80, 89, 10, 15; 71/90, 92

[56] References Cited

U.S. PATENT DOCUMENTS 4,017,510  4/1977  Los ................................... 71/92 X

FOREIGN PATENT DOCUMENTS 41623  12/1981  European Pat. Off. .
41624  12/1981  European Pat. Off. .

OTHER PUBLICATIONS

Frehel, et al., *Chemical Abstracts*, vol. 97, (1982), Entry 72346t.

*Primary Examiner*—Donald G. Daus
*Assistant Examiner*—William A. Teoli, Jr.
*Attorney, Agent, or Firm*—H. G. Jackson

[57] ABSTRACT

There are provided novel (2-imidazolin-2-yl)-thieno and furo compounds, and intermediate compounds for the preparation thereof, and a method for controlling a wide variety of annual and perennial plant species therewith.

32 Claims, No Drawings

(2-IMIDAZOLIN-2-YL)THIENO- AND FURO[2,3-B] AND [3,2-b]PYRIDINES AND INTERMEDIATES FOR THE PREPARATION THEREOF, AND USE OF SAID COMPOUNDS AS HERBICIDAL AGENTS

This application is a continuation-in-part of abandoned U.S. Ser. No. 611,191 filed May 21, 1984 which is a continuation-in-part of abandoned U.S. Ser. No. 500,219 filed June 2, 1983.

The present invention relates to novel (2-imidazolin-2-yl)thieno- and furopyridine compounds, and intermediates for the preparation of said pyridine compounds and a method for controlling undesirable annual and perennial plant species therewith.

More particularly, this invention relates to 6-(2-imidazolin-2-yl)thieno- and furo[2,3-b] and 5-(2-imidazolin-2-yl)thieno- and furo[3,2-b]pyridine compounds and the corresponding 2,3-dihydrothieno and 2,3-dihydrofuro compounds having the structures (Ia) and (Ib):

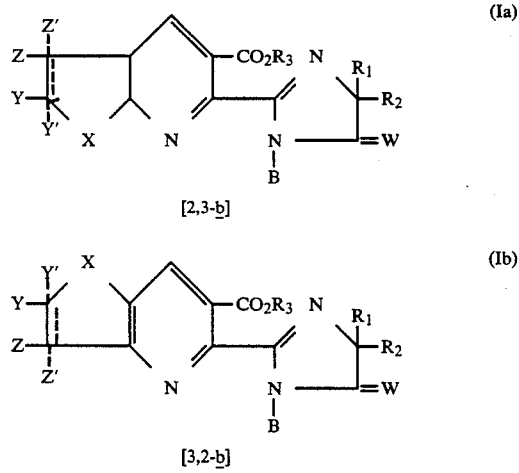

wherein ≟ represents a single or a double bond; $R_1$ is $C_1$–$C_4$ alkyl; $R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl; $R_3$ is hydrogen; $C_1$–$C_4$ alkyl, which may be interrupted by O or S and is optionally substituted with one of the following groups: furyl, phenyl, halophenyl, $C_1$–$C_4$ alkylphenyl, $C_1$–$C_4$ alkoxyphenyl or nitrophenyl; $C_3$–$C_6$ alkenyl optionally substituted with one or two halogens; $C_3$–$C_6$ alkynyl; or a cation of alkali metals, alkaline earth metals, manganese, copper, iron, ammonium or organic ammonium; B is H, $COR_4$ or $SO_2R_5$, provided that when B is $COR_4$, $R_3$ cannot be hydrogen or a salt-forming cation; $R_4$ is $C_1$–$C_4$ alkyl, chloromethyl or phenyl optionally substituted with one chloro, one nitro, one methyl, or one methoxy group; $R_5$ is $C_1$–$C_5$ alkyl or phenyl optionally substituted with one methyl group, chloro or nitro; W is O or S; X is O, S, or, where ≟ is a single bond, X is S=O; Y and Y', Z and Z' are hydrogen, halogen, $C_1$–$C_6$ alkyl, $C_1$–$C_6$ alkoxy, $C_1$–$C_6$ alkanoyloxy, $C_1$–$C_4$ alkylthio, phenoxy, $C_1$–$C_4$ haloalkyl, $C_1$–$C_4$ haloalkoxy, nitro, cyano, $C_1$–$C_4$ dialkylamino or phenyl optionally substituted with one or two $C_1$–$C_4$ alkyl, $C_1$–$C_4$ alkoxy, halogen, or any combination of two of these groups with the proviso that when Y and Z are the same group they are H, halogen, alkyl or alkoxy, and when Y and Y' or Z and Z' are the same group they are hydrogen or alkyl; and, when taken together, Y and Z may form a ring in which YZ are represented by the structure $-(CH_2)_n-$, where n is an integer of 3 or 4, or

wherein L, M, Q and $R_7$ each represent hydrogen, halogen, $C_1$–$C_4$ alkyl or $C_1$–$C_4$ alkoxy, with the proviso that only one of L, M, Q or $R_7$, may represent a substituent other than hydrogen, halogen, $C_1$–$C_4$ alkyl or $C_1$–$C_4$ alkoxy; the pyridine N-oxides thereof; and when $R_1$ and $R_2$ are not the same, the optical isomers thereof; and, except when $R_3$ is a salt-forming cation, the acid addition salts thereof.

A preferred group of 6-(2-imidazolin-2-yl)-thieno- and furo[2,3-b]pyridine and 5-(2-imidazolin-2-yl)thieno- and furo[3,2-b]pyridine compounds have the formula shown as (Ia) and (Ib) above, wherein ≟ represents a single or a double bond; $R_1$ is $C_1$–$C_4$ alkyl; $R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl; $R_3$ is hydrogen; $C_1$–$C_4$ alkyl, which may be optionally substituted with one of the following groups: furyl, phenyl, halophenyl, $C_1$–$C_4$ alkylphenyl, $C_1$–$C_4$ alkoxyphenyl or nitrophenyl; $C_3$–$C_6$ alkynyl; or a cation of alkali metals, alkaline earth metals, ammonium or mono, di, tri, or tetra $C_1$–$C_{22}$ alkylammonium; B is H, $COR_4$ or $SO_2R_5$, provided that when B is $COR_4$, $R_3$ cannot be hydrogen or a salt-forming cation; $R_4$ is $C_1$–$C_4$ alkyl, chloromethyl or phenyl optionally substituted with one chloro, one nitro, one methyl or one methoxy group; $R_5$ is $C_1$–$C_5$ alkyl or phenyl optionally substituted with one methyl group, chloro or nitro; W is O or S; X is O, S, or, where ≟ is a single bond, S=O; Y and Y', Z and Z' are hydrogen, halogen, $C_1$–$C_6$ alkyl, $C_1$–$C_6$ alkoxy, $C_1$–$C_6$ alkanoyloxy, $C_1$–$C_4$ haloalkyl, $C_1$–$C_4$ haloalkoxy, nitro, $C_1$–$C_4$ dialkylamino or phenyl with the proviso that when Y and Z are the same group they are H, halogen, alkyl or alkoxy, and that when ≟ is a single bond, Y, Y', Z and Z' are hydrogen, alkyl, alkoxy or halogen, and when Y and Y' or Z and Z' are the same group they are hydrogen or alkyl; and, when taken together, Y and Z may form a ring in which YZ are represented by the structure $-(CH_2)_n-$, where n is an integer selected from 3 or 4, or $-CH=CH-CH=CH-$; the pyridine N-oxides thereof; and when $R_1$ and $R_2$ are not the same, the optical isomers thereof; and, except when $R_3$ is a salt-forming cation, the acid addition salts thereof.

A more preferred group of formula (Ia) and (Ib) 6-(2-imidazolin-2-yl)thieno- and furo[2,3-b]pyridine and 5-(2-imidazolin-2-yl)thieno- and furo[3,2-b]pyridine compounds are those wherein ≟ represents a single bond; X is oxygen, sulfur, or S=O; Y and Z are hydrogen, methoxy, methyl, or chlorine, with the proviso that one of Y and Z is hydrogen; $R_3$ is hydrogen, furfuryl, propynyl, methyl or a cation of alkali metals, alkaline earth metals, ammonium or mono, di, tri or tetra $C_1$–$C_{22}$ alkylammonium; $R_1$ and $R_2$ are methyl, ethyl, isopropyl, or when taken together form a cyclohexyl or 2-methylcyclohexyl ring, and when $R_1$ and $R_2$ are not the same, the optical isomers thereof.

Another more preferred group of formula (Ia) and (Ib) 6-(2-imidazolin-2-yl)thieno- and furo[2,3-b]pyridine and 5-(2-imidazolin-2-yl)thieno- and furo[3,2-b]pyridine compounds are those wherein X is oxygen or sulfur; B is H; Y and Z are hydrogen, methyl, ethyl, chlorine, bromine, methoxy or phenyl; $R_3$ is hydrogen, propynyl, furfuryl, methyl or a cation of alkali metals, alkaline earth metals, ammonium or mono, di, tri or tetra $C_1$–$C_{22}$ alkylammonium; $R_1$ and $R_2$ are methyl, ethyl, isopropyl, or when taken together form a cyclohexyl or 2-methylcyclohexyl ring; W is O or S, and when $R_1$ and $R_2$ are not the same, the optical isomers thereof.

A most preferred group of formula (Ia) 6-(2-imidazolin-2-yl)thieno- and furo[2,3-b]pyridine compounds are those wherein X is oxygen or sulfur; Y is hydrogen or methyl; Z is hydrogen, chlorine or bromine, $R_3$ is hydrogen, propynyl, furfuryl or a sodium, ammonium or mono, di, tri or tetra $C_1$–$C_{22}$ alkylammonium cation; W is O or S, and the optical isomers thereof.

It should also be understood that when B is H the imidazolinyl thieno- and furo[2,3-b] and [3,2-b]pyridines represented by formula (Ia) and (Ib) above may be tautomeric. While, for convenience, they are depicted by single structures identified as formula (Ia) and (Ib), they may exist in either of the tautomeric forms illustrated as follows:

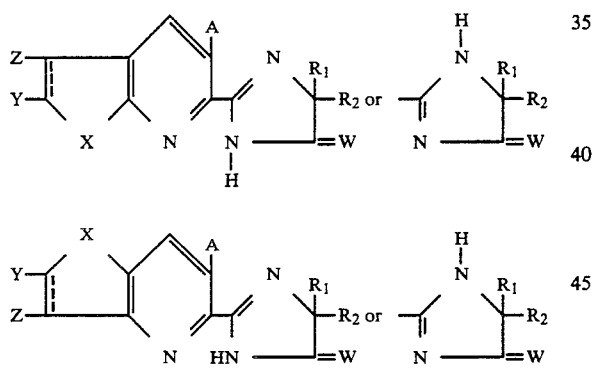

As such, both tautomeric forms of said imidazolinylpyridines are meant to be included under the formula (Ia) and (Ib) definition.

The present invention also relates to novel substituted thieno- and furoimidazopyrrolopyridinedione compounds of structure (IIa) and (IIb) below and a method for controlling undesirable annual and perennial plant species therewith in soybeans and certain cereal crops:

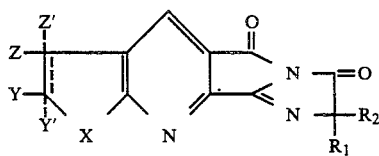

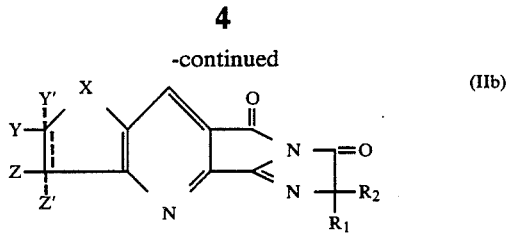

wherein X, Y, Y', Z, Z', W, $R_1$ and $R_2$ are as described for (Ia) and (Ib) above and wherein X, Y, Z, W, $R_1$ and $R_2$ in the preferred, more preferred and most preferred formula (IIa) and (IIb) compounds are as described for the preferred, more preferred and most preferred formula (Ia) and formula (Ib) compounds.

Herbicidal substituted pyridine and quinoline2-imidazolin-2-yl acids, esters and salts are disclosed in European Patent Application No. 81103638.3 filed Dec. 1, 1981. The present invention relates to novel thieno- and furo[2,3-b]pyridines and thieno- and furo[3,2-b]pyridines which when substituted in the 6 or 5 position with an imidazolinone ring and in the 5 or 6 position with a group $CO_2R_3$ as previously defined, provide potent herbicidal agents. The finding that imidazolinyl thieno- and -furopyridines provide potent herbicides is unexpected as there is no prior indication that such [2,3-b] or [3,2-b] ring system may be employed for any agronomic or herbicidal utility. This new class of herbicidal agents is highly effective when applied as a pre- or postemergence treatment, and individual members of this class exhibit unusual selectivity in soybean and cereal crops such as wheat, barley, rice, rye and oats. Further, it has been found that selectivity in cereals may be enhanced when $R_3$ is H, by the preparation of esters, particularly furfuryl, alkynyl an haloalkenyl esters.

Additionally some members of this class exhibit unexpected plant growth regulating effects such as reduced plant height and antilodging activity and increased tillering in cereal crops.

The compounds of the present invention may conveniently be prepared from the appropriately substituted thieno- and furo[2,3-b] and [3,2-b]pyridinedicarboxylic acids and esters of formula (IIIa) and (IIIb):

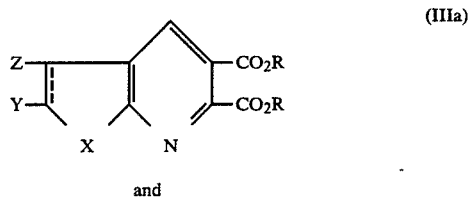

and

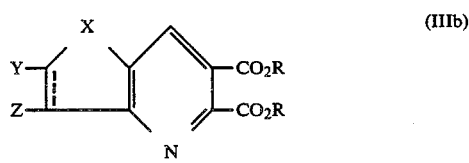

wherein X, Y and Z are as previously described and R is methyl or ethyl.

Methods suitable for preparing novel formula (Ia) and formula (Ib) unsaturated compounds wherein is a double bond from the novel formula (IIIa) and (IIIb) pyridinecarboxylic acid esters are illustrated in Flow Diagram I below.

Thus formula (IIIa) and (IIIb) diesters may be hydrolyzed to the corresponding thieno- and furo-2,3-pyridinedicarboxylic acids of formula (IVa) and (IVb) by reaction thereof with a strong base such as potassium hydroxide or sodium hydroxide. Acid anhydrides of formula (Va) and (Vb) may then be prepared by treatment of the formula (IVa) and (IVb) pyridinedicarboxylic acids with, for example, acetic anhydride. Reaction of formula (Va) and (Vb) anhydrides with an appropriately substituted aminocarboxamide or aminothiocarboxamide depicted by formula (VI) yields carbamoyl nicotinic acids of formula (VIIa) and (VIIb). Treatment of the thus-formed formula (VIIa) and (VIIb) carbamoyl nicotinic acids with about 2 to 10 molar equivalents of aqueous or aqueous alcoholic sodium or potassium hydroxide, preferably under a blanket of inert gas such as nitrogen, cooling and acidifying to pH 2 to 4 with a strong mineral acid such as hydrochloric acid or sulfuric acid gives herbicidally effective 6-(4,4-disubstituted-5-oxo-(or thioxo)-2-imidazolin-2-yl)thieno- and furo[2,3-b]pyridine-5-carboxylic acids, and 5-(4,4-disubstituted-5-oxo-(or thioxo)-2-imidazolin-2-yl)thieno- and furo[3,2-b]pyridine-6-carboxylic acids encompassed by formulas (Ia) and (Ib).

Formula (Ia) and (Ib) 5 or 6-(2-imidazolin-2-yl)thieno- and furopyridine esters, wherein $R_3$ represents a substituent other than hydrogen or a salt-forming cation, and $R_1$, $R_2$, X, Y and Z are as described above can be prepared by reacting a novel thieno- or furoimidazopyrrolopyridinedione, represented by formulas (IIa) and (IIb), hereinbelow, in Flow Diagram (II), with an appropriate alcohol and corresponding alkali metal alkoxide at a temperature ranging between about 20° C. and about 50° C.

Formula (IIa) and (IIb) novel thieno- and furoimidazopyrrolopyridinediones may conveniently be prepared from formula (Ia) and (Ib) acids, where B is H by treatment with one equivalent of dicyclohexylcarbodiimide in an inert solvent such as methylene chloride as illustrated in Flow Diagram (II) below.

FLOW DIAGRAM (I)

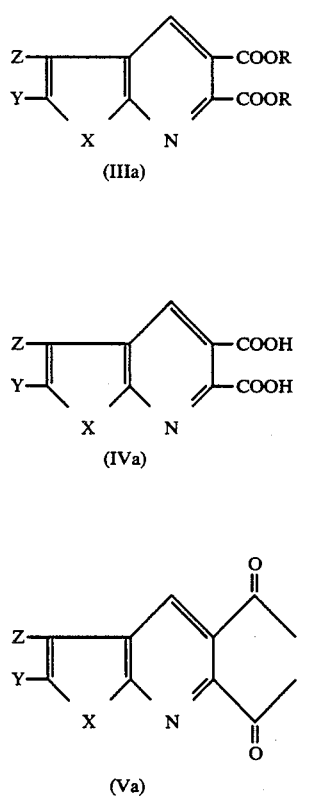
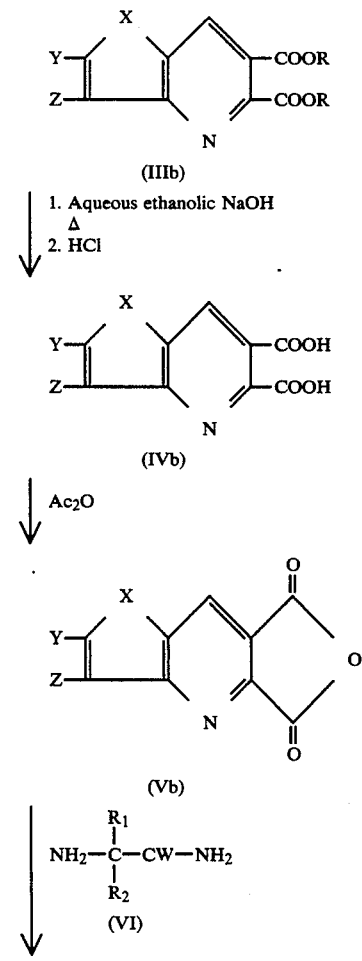

-continued
FLOW DIAGRAM (I)

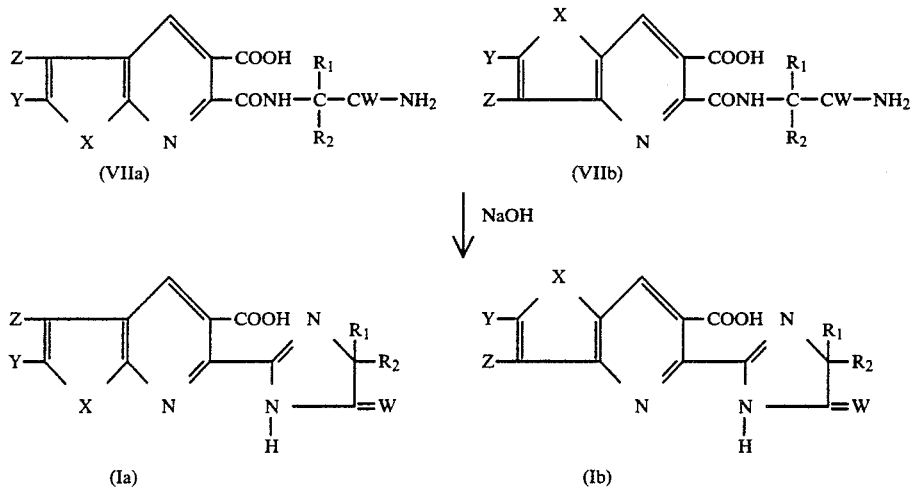

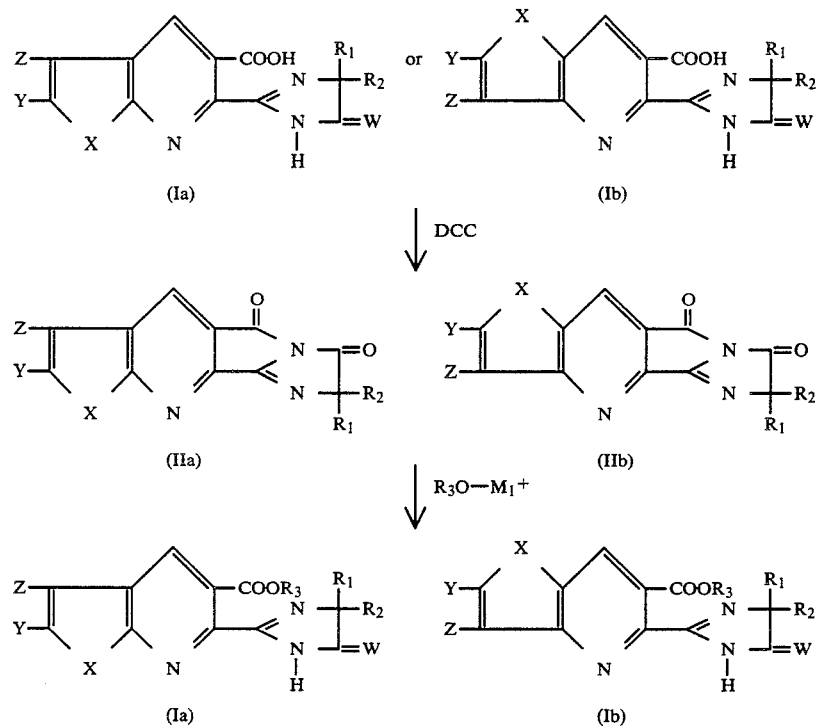

where $M_1$ is an alkali metal, and X, Y, Z, $R_1$, $R_2$ and $R_3$ are as above defined.

Many formula (IIIa) thieno[2,3-b]pyridinedicarboxylic acids and (IIIb) thieno[3,2-b]pyridinedicarboxylic acids may conveniently be prepared by reacting the appropriately substituted 2 or 3-aminothiophene of formula (VIIIa) or (VIIIb), where R is hydrogen or chloro, with a $C_1$-$C_4$ alkyl ester of acetylenedicarboxylic acid of formula (IX) as described by Bleckert et al. Chem. Ber. 1978, 106, 368. The thus-formed β-aminothieno-α,β-unsaturated ester of formula (X) is then reacted with an immonium salt depicted by the formula Cl—CH=N⊕—(R''')$_2$ Cl⊖ wherein R''' is $C_1$-$C_6$ alkyl or Cl—CH=N⊕(CH$_2$)$_n$'Cl⊖ where n' is 4 or 5, in the presence of a low boiling chlorinated hydrocarbon solvent such as methylene chloride or dichloroethane at a temperature between about 40° C. and 90° C., for a period of time sufficient to essentially complete the reaction and yield the formula (IIIa) [2,3-b]thieno- or (IIIb) [3,2-b]thieno-2,3-pyridinedicarboxylic acid as the dialkyl ester as illustrated in Flow Diagram (III) below.

Formula (IIIb) furo[3,2-b]pyridinedicarboxylic acids may be prepared by reacting 3-amino-2-formylfuran of formula (XI) prepared by the method of S. Gronowitz et al., Acta Chemica Scand B29 224(1975) with ethyl oxalacetate to give formula (IIIb) furopyridine compounds directly, as illustrated in Flow Diagram (IV) below while formula (IIIa) furo[2,3-b]pyridine compounds where Y and Z are H are obtained by bromination of the reaction product (XII) of acetoacetamide with the diethyl ester of ethoxymethyleneoxalacetic acid followed by treatment with sodium borohydride and para-toluene sulfonic acid in refluxing xylene as illustrated in Flow Diagram (V) below.

Formula (IIIb) 2,3-dihydrofuro[3,2-b] and thieno[3,2-b]pyridines may be prepared by the reaction of diethylethoxymethylene oxalacetate with a mixture of enamines derived from 3-keto-tetrahydrofuran or 3-keto-tetrahydrothiophene, followed by treatment with ammonia or ammonium, as illustrated in Flow Diagram (VI).

This procedure is described in pending application for U.S. Letters Patent, Ser. No. 676,133 of J. Johnson, filed June 20, 1986.

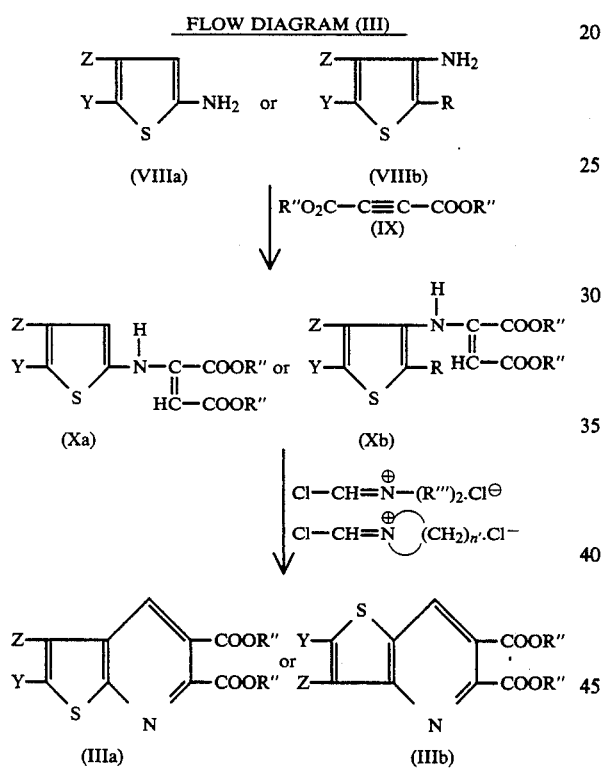

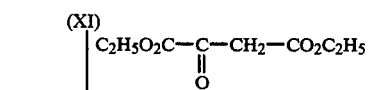

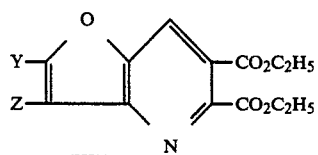

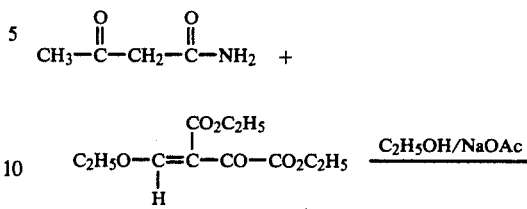

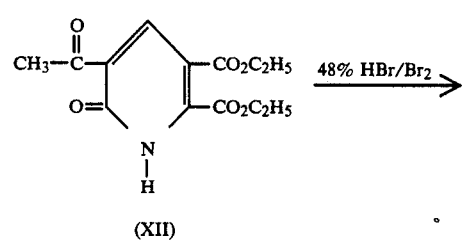

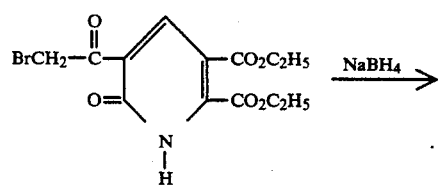

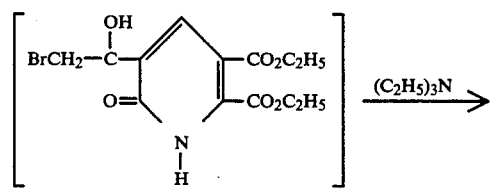

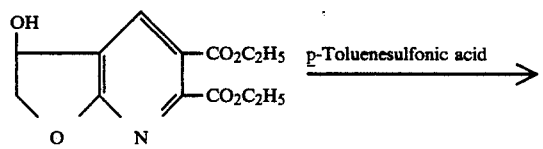

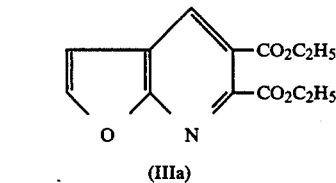

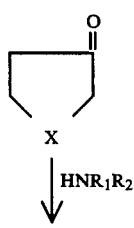

-continued
FLOW DIAGRAM (VI)

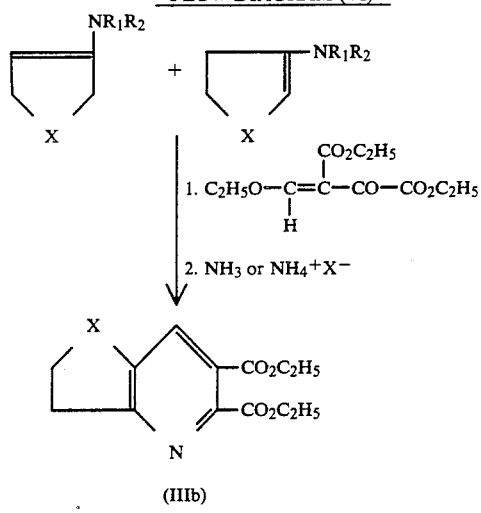

wherein $R_1$ and $R_2$ each represents $C_1$–$C_6$ alkyl or taken together with the nitrogen atom to which they are attached form a 5 or 6 membered saturated heterocyclic ring, optionally containing at most 2 hetero atoms.

Formula (IIIa) furo[2,3-b]pyridine compounds where Z is H and Y is alkyl or optionally substituted phenyl are prepared by reaction of an acetylene compound with the iodopyridine diester (VII) [preparation of this compound VII is described in J. Prakt. Chem., 148; 72(1937)], in the presence of cuprous salts, an amine base, and a palladium (II) catalyst as shown in Flow Diagram (VII).

FLOW DIAGRAM (VII)

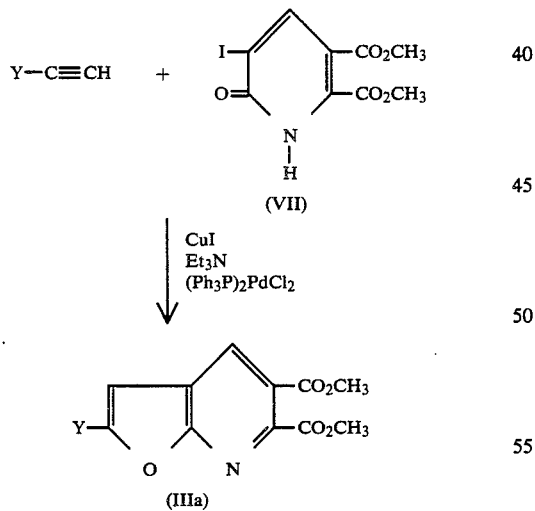

Substituents represented by Y and Z in formula (Ia), (Ib), (IIa) and (IIb) compounds of the present invention may be prepared either by using the appropriately substituted starting material for the preparation of formula (IIIa) and (IIIb) thieno- and furopyridine-5,6-dicarboxylic acid esters or by electrophilic substitution (halogenation, nitration, sulfonation, etc.) directly upon Formula (IIIa) or (IIIb) diesters or Formula (Ia) or (Ib) final products, wherein at least one of Y or Z is hydrogen. These substituted Formula (IIIa), (IIIb), (Ia) and (Ib) compounds then may be used as starting materials for additional Y and Z substitution by displacement, reduction, oxidation, etc. Representative substituted (IIIa) and (IIIb) compounds which may be prepared by these procedures are as illustrated below.

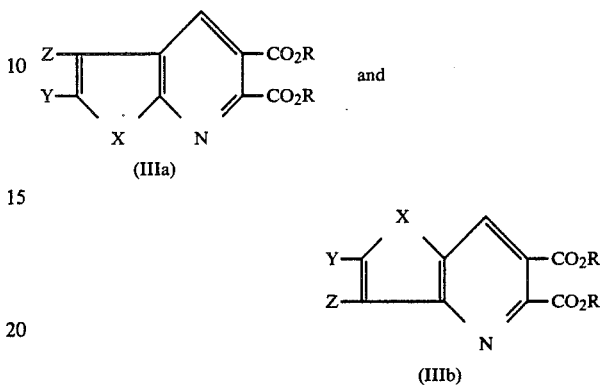

| X | Y | Z | R |
|---|---|---|---|
| S | H | H | $CH_3$ |
| S | H | Br | $CH_3$ |
| S | $CH_3$ | H | $CH_3$ |
| S | H | Cl | $CH_3$ |
| S | Cl | Cl | $CH_3$ |
| S | H | I | $CH_3$ |
| S | H | $NO_2$ | $CH_3$ |
| S | Br | Br | $CH_3$ |
| S | $CH_3$ | Cl | $CH_3$ |
| S | H | $CH_3$ | $CH_3$ |
| S | Cl | H | $CH_3$ |
| S | $CH_3$ | $CH_3$ | $CH_3$ |
| S | H | CN | $CH_3$ |
| S | H | $OCH_3$ | $CH_3$ |
| S | H | $N(CH_3)_2$ | $CH_3$ |
| S | H | $SCH_3$ | $CH_3$ |
| S | H | $OCF_2H$ | $CH_3$ |
| O | H | H | $C_2H_5$ |
| O | H | Br | $CH_3$ |
| O | H | Br | $C_2H_5$ |
| O | H | Cl | $CH_3$ |
| O | H | Cl | $C_2H_5$ |
| O | $CH_3$ | H | $CH_3$ |
| O | $CH_3$ | H | $C_2H_5$ |
| O | H | $CH_3$ | $CH_3$ |
| O | $C_2H_5$ | H | $CH_3$ |
| O | H | $C_2H_5$ | $CH_3$ |
| O | $CH_3$ | $CH_3$ | $CH_3$ |
| S | —$(CH_2)_3$— | | $CH_3$ |
| S | —$(CH_2)_4$— | | $CH_3$ |
| S | —$(CH)_4$— | | $CH_3$ |
| S | $C_6H_5$ | H | $CH_3$ |
| O | $C_6H_5$ | H | $CH_3$ |
| S | H | $SO_2N(CH_3)(CH_3)$ | $CH_3$ |
| S | H | $OC_6H_5$ | $CH_3$ |
| O | H | $OC_6H_5$ | $CH_3$ |
| O | $CF_3$ | H | $CH_3$ |
| O | H | $NO_2$ | $C_2H_5$ |
| O | Br | Br | $C_2H_5$ |
| O | H | $C_6H_5S$ | $C_2H_5$ |
| O | H | $CF_3$ | $C_2H_5$ |

Additionally, novel herbicidal 2,3-dihydrothieno[2,3-b] and [3,2-b]pyridine compounds may be obtained by starting the sequence in Flow Diagram (III) above with a dihydrothiophenimin hydrochloride. Novel herbicidal 2,3-dihydro furo[2,3-b] and [3,2-b]pyridines may be prepared by catalytic reduction of the formula (Ia) or (Ib) (2-imidazolin-2-yl) product, or (IIIa) and (IIIb) furo[2,3-b] and [3,2-b]pyridine-5,6-diesters as for example with hydrogen and palladium on carbon, provided that Y and Z are substituents which are not reduced by such a procedure. Other 2,3-dihydrofuro[2,3-b]pyridines are prepared by the reduction-rearrangement of a bromo ketone with sodium borohydride followed by treatment with triethylamine, and p-toluenesulfonic acid as shown in Flow Diagram (VIII). This then provides novel 2,3-dihydro herbicidal compounds illustrated below.

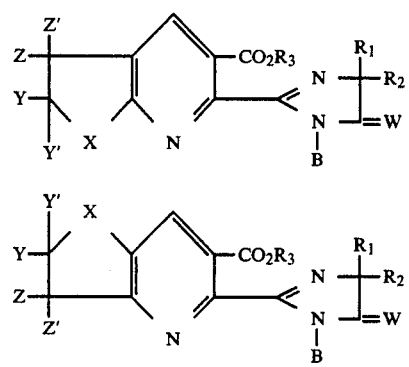

wherein X, Y, Y', Z, Z', W, B, $R_1$ and $R_3$ are as described for (Ia) and (Ib).

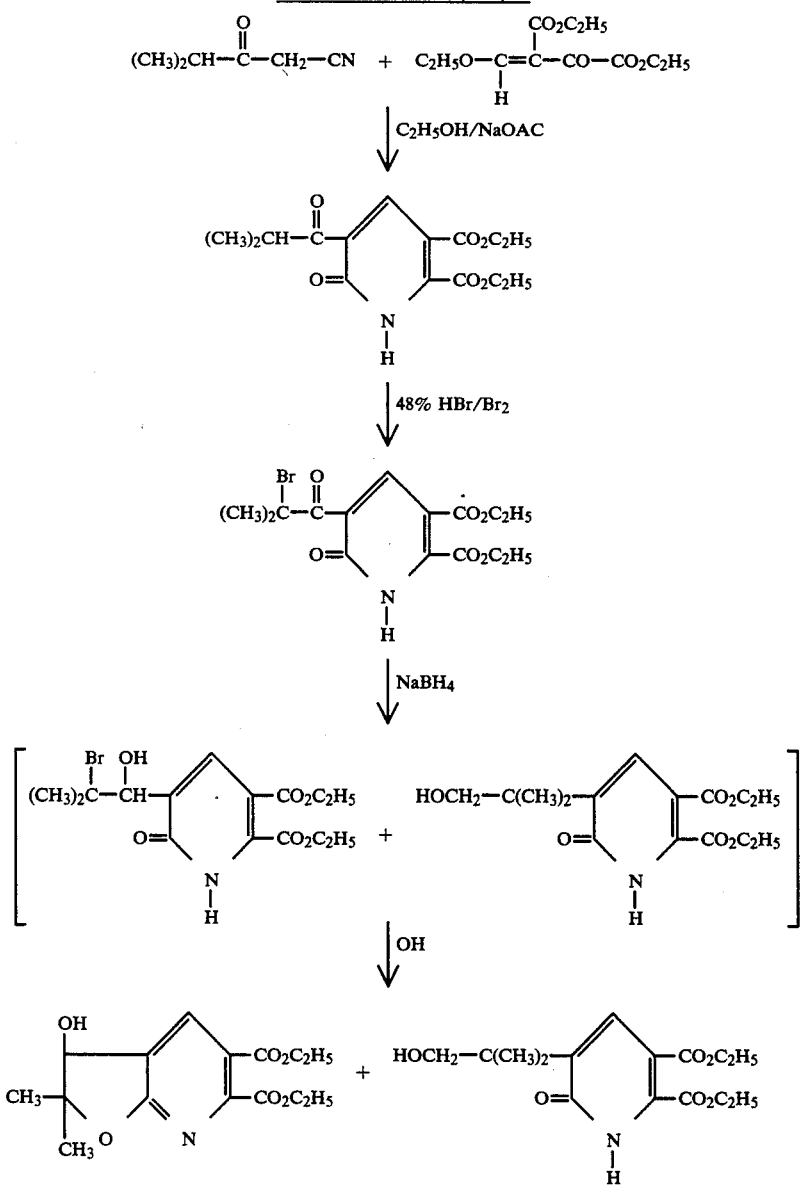

FLOW DIAGRAM (VIII) -continued

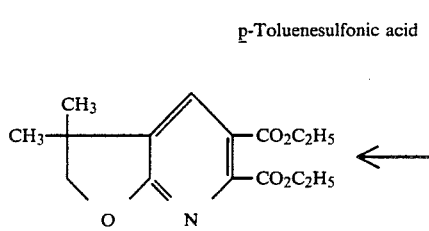

The formula (Ia) and formula (Ib) 6-(2-imidazolin-2-yl)thieno- and furo[2,3-b]pyridines and 5-(2-imidazolin-2-yl)thieno- and furo[3,2-b]pyridines and the formula (IIa) and formula (IIb) imidazopyrrolopyridinediones of the present invention are exceedingly effective herbicidal agents useful for the control of an exceptionally wide variety of herbaceous and woody annual and perennial monocotyledonous and dicotyledonous plants. Moreover, these compounds are herbicidally effective for controlling weeds indigenous to both dry land and wet land areas. They are also useful as aquatic herbicides and are unique in their effectiveness in controlling the above-said plants when applied to the foliage thereof or to soil or water containing seeds or other propagating organs of said plants such as tubers, rhizomes or stolons, at rates of from about 0.016 to 4.0 kg/ha, and preferably at rates from about 0.032 to 2.0 kg/ha.

It is, of course, obvious that rates of application above the 4.0 kg/ha level can also be used to effectively kill undesirable plant species; however, rates of application of toxicant above the level necessary to kill the undesirable plants should be avoided since application of excessive amounts of toxicant is costly and serves no useful function in the environment.

Among the plants which may be controlled with the compounds of this invention are: *Elatine triandra, Sagittaria pygmaea, Scirpus hotarui, Cyperus serotinus, Eclipta alba, Cyperus difformis, Rotala indica, Lindernia pyridoria, Echinochloa crus-galli, Digitaria sanguinalis, Setaria viridis, Cyperus rotundus, Convolvulus arvensis, Argropyron repens, Datura stramonium, Alopercurus myosuroides,* Ipomoea spp., *Sida spinosa, Ambrosia artemisiifolia, Eichhornia crassipes, Xanthium pensylvanicum, Sesbania exaltata, Avena fatua, Abutilon theophrasti, Bromus tectorum, Sorghum halepense,* Lolium spp., *Panicum dichotomiflorum,* Matricaria spp., *Amaranthus retroflexus, Cirsium arvense* and *Rumex iaponicus.*

It has been found that the formula (Ia) and (Ib) (2-imidazolin-2-yl)thieno- and furopyridines are generally selective herbicides, particularly effective for controlling undesirable weeds in the presence of leguminous crops such as soybeans, and cereal crops such as wheat, barley, oats and rye. However, certain of the formula (Ia) and formula (Ib) compounds are less selective than others in this series.

It has also been found that several of the formula (Ia) and formula (Ib) (2-imidazolin-2-yl)-pyridines are effective as antilodging agents in cereal crops when applied at rates of application between about 0.016 to 4.0 kg hectare. At rates of application not exceeding about 0.010 kg per hectare, it has also been found that certain of the formula (Ia) and formula (Ib) thieno- and furopyridines are effective for increasing branching of leguminous crops and tillering of cereal crops.

Since the formula (Ia) and formula (Ib) imidazolinylthieno- and furopyridines and derivatives, wherein $R_3$ is a salt-forming cation, are water soluble, these compounds can simply be dispersed in water and applied as a dilute aqueous spray to the foliage of plants or to soil containing propagating organs thereof. These salts also lend themselves to formulation as flowable concentrates.

The formula (Ia) and formula (Ib) (2-imidazolin-2-yl)thieno- and furopyridines and the formula (IIa) and formula (IIb) imidazopyrrolopyridinediones can also be formulated as wettable powders, flow concentrates, emulsifiable concentrates, granular formulations and the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of dimethyl thieno[3,2-b]pyridine-5,6-dicarboxylate

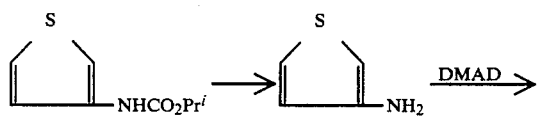

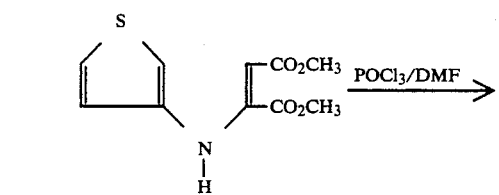

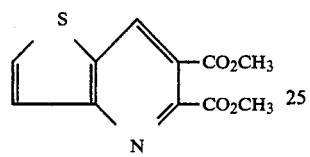

A mixture of isopropyl-3-thiophenecarbamate (177 g; 0.975 mol) in methanol (1.2 l) and water (2.8 l) containing sodium hydroxide (200 g) is heated at reflux for four hours. Methanol is removed under reduced pressure and the cooled reaction extracted with ether (5 l), and these extracts are washed with water, aqueous sodium chloride and dried. Evaporation under reduced pressure affords 3-aminothiophene as an oil in 57% crude yield.

3-Aminothiophene is redissolved in methanol (500 mL) cooled in an ice bath and dimethylacetylenedicarboxylate (80 g; 0.50 mol) is added dropwise. The mixture is stirred at room temperature for 15 hours and 30 minutes, the methanol removed under reduced pressure and 1,2-dichloroethane is added. This solvent is also evaporated off to give dimethyl 3-thienylaminobutenedioate as an oil.

A Vilsmeier reagent is prepared by adding dropwise, with stirring phosphorus oxychloride (86 g, 0.56 mol) to a cooled (5° C.) solution of DMF (41 g, 0.56 mol) in 1,2-dichloroethane (200 mL). This reagent is stirred at room temperature for one hour and 40 minutes, diluted with 1,2-dichloroethane (100 mL), cooled to 5° C., and then the above dimethyl ester dissolved in 1,2-dichloroethane (400 mL) is added to the Vilsmeier reagent at 5° C. dropwise over a 25 minute period. The reaction temperature is raised to room temperature for 15 minutes, then to reflux for a further two hours and 25 minutes. The cooled reaction mixture is chromatographed directly on a silica gel column affording 35.7 g (15%) of dimethyl thieno[3,2-b]pyridine-5,6-dicarboxylate mp 124°–125.5° C. after crystallization from hexane-ethylacetate. A second crop 10.3 g with mp 121°–124° C. is obtained giving an overall yield from isopropyl 3-thiophenecarbamate of 19%.

Utilizing the above procedure and substituting the appropriate substituted aminothiophene for isopropyl 3-aminothiophenecarbamate yields the compounds illustrated below.

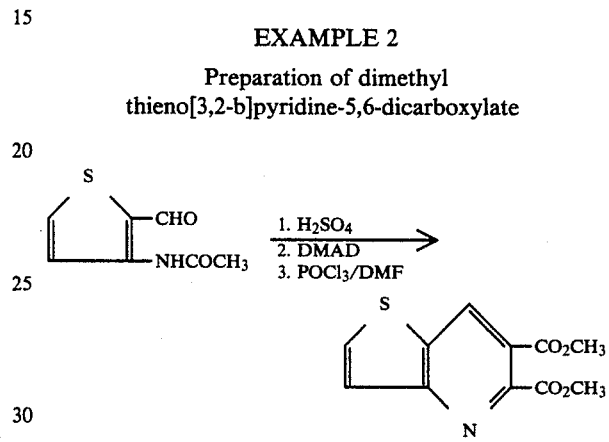

| Y   | Z | R   | mp °C.  |
|-----|---|-----|---------|
| H   | H | CH3 | 126–127 |
| CH3 | H | CH3 | —       |
| Cl  | H | CH3 | 149–151 |

EXAMPLE 2

Preparation of dimethyl thieno[3,2-b]pyridine-5,6-dicarboxylate

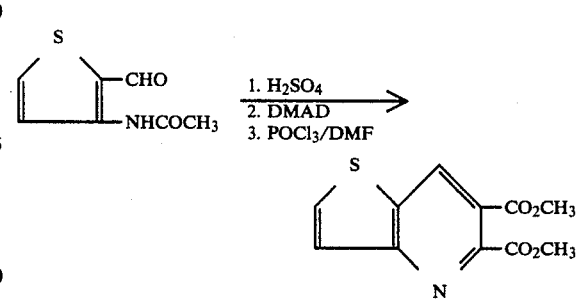

To concentrated sulfuric acid (170 mL), stirred at room temperature is added in portions 3-acetylamino-2-formylthiophene (17.5 g, 0.103 mol). The mixture is heated at 50° C. for 30 minutes, cooled and poured into an ice-water mixture. After neutralizing with an excess of sodium acetate, the mixture is ether (1×2 mL) extracted. The organic layer was dried over anhydrous Na2SO4 and stripped to a dark red gum consisting of 3-amino-2-formylthiophene. Dimethylacetylenedicarboxylate (DMAD) (13 mL) in acetic acid (5 mL), piperidine (5 mL), methylene chloride (100 mL) and toluene (100 mL) is added to the 3-amino-2-formylthiophene and the mixture stirred overnight. Methylene chloride is removed by distillation and then the mixture heated at reflux for 24 hours. After cooling an additional 13 mL of DMAD is added and the reaction heated to reflux again for seven and one-half hours. After standing for 60 hours at room temperature, the solvents are removed and the dimethyl thieno[3,2-b]pyridine-5,6-dicarboxylate product is obtained by chromatography, after eluting with hexane-ethyl acetate, mp 124°–125° C.

EXAMPLE 3

Preparation of dimethyl 3-chloro[3,2-b]pyridine-5,6-dicarboxylate and dimethyl 2,3-dichlorothieno[3,2-b]pyridine-5,6-dicarboxylate

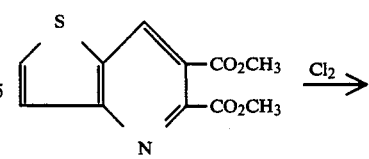

-continued

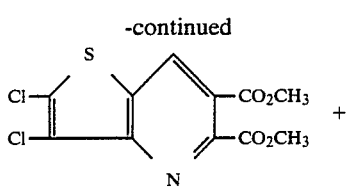

+

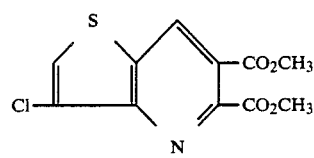

A solution of dimethyl thieno[3,2-b]pyridine-5,6-dicarboxylate (15 g 0.0525 mol) in acetic acid (680 mL) and sodium acetate (86 g, 0.093 mol) is maintained at 58° C. while chlorine is slowly introduced during five hours and 45 minutes. After reaction is complete, the mixture is flushed with nitrogen, ethyl acetate (200 mL) is added and solid sodium chloride filtered off and washed with ethyl acetate. The mother liquors and washes are combined and the solvents removed under reduced pressure. The residue is dissolved in methylene chloride and the solution washed with water, back extracted with methylene chloride and the combined methylene chloride layers washed with aqueous sodium bicarbonate, dried and stripped to give 18 g of solid. Chromatography on silica gel with 15% ethyl acetatehexane, then 20% ethyl acetate-hexane gives the 2,3-dichloro compound, mp 173°-178° C., 1.3 g, followed by the 3-chlorothieno compound mp 166°-173° C. after crystallization from ethyl acetate-hexane.

EXAMPLE 4

Preparation of dimethyl 3-bromothieno[3,2-b]pyridine-5,6-dicarboxylate

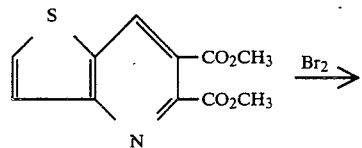

A solution of bromine (20 g, 0.125 mol) in acetic acid (50 mL) is added dropwise over three hours to a solution of dimethyl thieno[3,2-b]pyridine-5,6-dicarboxylate, (26.3 g, 0.104 mol), containing sodium acetate (17.2 g, 0.2 mol) in acetic acid (300 mL) at 85° C. Additional sodium acetate (18 g) and bromine (20 g) in acetic acid (50 mL) is added over an hour and the mixture stirred at 85° C. overnight. Bromine (10 g) is added in one portion then left at 85° C. for four hours. The mixture is cooled and treated with aqueous sodium bisulfite, diluted with ethyl acetate and concentrated. The reaction product is partitioned between water and methylene chloride and the organic layer washed with aqueous sodium chloride and the solvent removed. The residue is washed with ether to give 25 g of crude product, mp 165°-168° C. Recrystallization from methanol gave needles of dimethyl 3-bromothieno[3,2-b]pyridine-5,6-dicarboxylate, mp 168°-169° C.

EXAMPLE 5

Preparation of thieno[3,2-b]pyridine-5,6-dicarboxylic acid

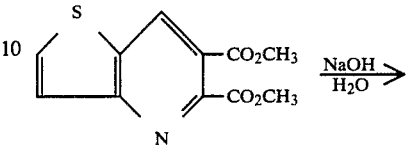

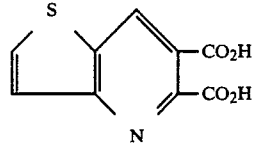

Dimethyl thieno[3,2-b]pyridine-5,6-carboxylate (3.75 g, 0.0149 mol) is added to a solution of sodium hydroxide (1.8 g, 0.045 mol) in water (20 mL) and the mixture is warmed at 60° C. for 20 hours. The reaction mixture is diluted with water, cooled in an ice bath, and acidified by the addition of concentrated hydrochloric acid. A precipitate of thieno[3,2-b]pyridine-5,6-dicarboxylic acid is filtered off and dried overnight to give 3.1 g (93%) mp >380° C.

Utilizing the above procedure and substituting the appropriate substituted thieno[3,2-b]pyridine-5,6-dicarboxylic acid diester yields the compounds illustrated below.

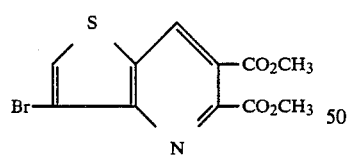

| Y | Z | mp °C. |
|---|---|---|
| H | H | >380 |
| H | Cl | None taken |
| H | Br | >380 |
| H | I | — |
| H | F | — |
| H | CN | — |
| H | OCH₃ | — |
| H | NO₂ | — |
| H | N(CH₃)₂ | — |
| CH₃ | H | — |
| H | CH₃ | — |
| CH₃ | CH₃ | — |
| H | OCHF₂ | — |
| H | SCH₃ | — |
| H | SO₂N(CH₃)₂ | — |
| C₆H₅ | H | — |
|  | —(CH₂)₃— | — |
|  | —(CH₂)₄— | — |
|  | —(CH)₄— | — |
| Cl | Cl | — |
| H | C₆H₅ | — |
| C₆H₅ | H | — |
| H | OC₆H₅ | — |
| CF₃ | H | — |
| C₂H₅ | H | — |
| H | C₂H₅ | — |
| H | SC₆H₅ | — |
| H | CF₃ | — |
| H | CHO | — |

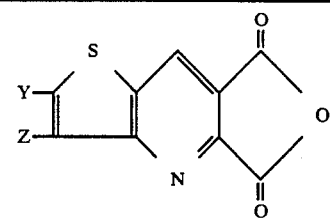

| Y | Z | mp °C. |
|---|---|---|
| H | CH₂Cl | — |

EXAMPLE 6

Preparation of 3-chlorothieno[3,2-b]pyridine 5,6-dicarboxylic acid anhydride

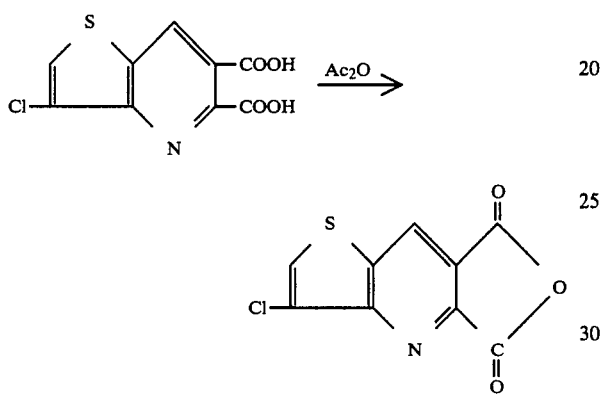

3-Chlorothieno[3,2-b]pyridine-5,6-dicarboxylic acid (1.45 g) is heated at 85° to 90° C. for 30 minutes then 90° to 102° C. for 30 minutes in acetic anhydride (7 mL). The reaction is cooled, the solids filtered off and washed with ether to give 1.2 g of 3-chlorothieno[3,2-b]pyridine-5,6-dicarboxylic acid anhydride. The proton magnetic resonance spectrum is consistant with the structure.

Utilizing the above procedure and substituting the appropriate pyridine-5,6-dicarboxylic acid for 3-chlorothieno[3,2-b]pyridine-5,6-dicarboxylic acid yields the compounds illustrated below.

| Y | Z | mp °C. |
|---|---|---|
| H | H | 266–267 |
| H | Cl | Solid no mp obtained |
| H | Br | >380 |
| Cl | H | — |
| Cl | Cl | — |
| H | NO₂ | — |
| CH₃ | H | — |
| H | N(CH₃)₂ | — |
| H | SCH₃ | — |
| H | OCH₃ | — |
| H | CH₃ | — |
| H | F | — |
| H | I | — |
| CH₃ | CH₃ | — |
| H | CN | — |
| H | OCHF₂ | — |
| H | SO₂N(CH₃)₂ | — |
| —(CH₂)₃— | | — |
| —(CH₂)₄— | | — |
| —(CH)₄— | | — |
| H | C₆H₅ | — |
| C₆H₅ | H | — |
| H | OC₆H₅ | — |
| CF₃ | H | — |
| C₂H₅ | H | — |
| H | C₂H₅ | — |
| H | SC₆H₅ | — |
| H | CF₃ | — |
| H | CHO | — |
| H | CH₂Cl | — |

EXAMPLE 7

Preparation of 5-(1-carbamoyl-1,2-dimethylpropyl)-3-chlorothieno[3,2-b]pyridine-6-carboxylic acid

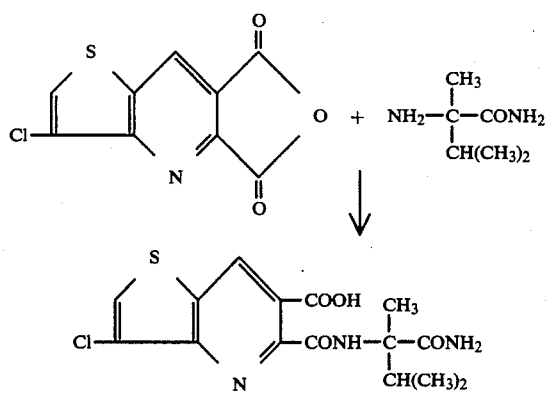

2-Amino-2,3-dimethylbutyramide (0.71 g) all in one portion is added to a stirred solution of 3-chlorothieno[3,2-b]pyridine-5,6-dicarboxylic acid anhydride, (1.2 g) in THF (1.0 mL). After standing for five minutes, the ice bath is removed and the reaction stirred at room temperature for 28 hours. The (5 mL) is added and the mixture heated at reflux for two hours and then set aside overnight. The cooled mixture is filtered and the collected solid washed with ether to give 1.4 g of the desired 5-[(1-carbamoyl-1,2-dimethylpropyl)carbamoyl]-3-chlorothieno[3,2-b]pyridine-6-carboxylic acid.

Utilizing the above procedure and substituting the appropriate pyridine-5,6-dicarboxylic and anhydride for 3-chlorothieno[3,2-b]pyridine-5,6-dicarboxylic acid anhydride and the appropriate aminoamide yields the compounds illustrated below.

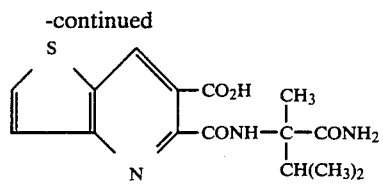

| Y | Z | R₁ | R₂ | mp °C. |
|---|---|---|---|---|
| H | H | CH₃ | i-C₃H₇ | — |
| H | Cl | CH₃ | i-C₃H₇ | not pure |
| Cl | H | CH₃ | i-C₃H₇ | — |
| Cl | Cl | CH₃ | i-C₃H₇ | — |
| H | Br | CH₃ | i-C₃H₇ | — |
| H | CH₃ | CH₃ | i-C₃H₇ | — |
| H | NO₂ | CH₃ | i-C₃H₇ | — |
| H | N(CH₃)₂ | CH₃ | i-C₃H₇ | — |
| H | SCH₃ | CH₃ | i-C₃H₇ | — |
| H | OCH₃ | CH₃ | i-C₃H₇ | — |
| CH₃ | H | CH₃ | i-C₃H₇ | — |
| H | H | CH₃ | C₃H₇ | — |
| H | H | CH₃ | C₂H₅ | — |
| H | OCHF₂ | CH₃ | i-C₃H₇ | — |
| CH₃ | CH₃ | CH₃ | i-C₃H₇ | — |
| H | CN | CH₃ | i-C₃H₇ | — |
| H | F | CH₃ | i-C₃H₇ | — |
| H | I | CH₃ | i-C₃H₇ | — |
| H | SO₂N(CH₃)₂ | CH₃ | i-C₃H₇ | — |
| C₆H₅ | H | CH₃ | i-C₃H₇ | — |
| —(CH₂)₃— | | CH₃ | i-C₃H₇ | — |
| —(CH₂)₄— | | CH₃ | i-C₃H₇ | — |
| —(CH)₄— | | CH₃ | i-C₃H₇ | — |
| H | C₆H₅ | CH₃ | i-C₃H₇ | — |
| C₂H₅ | H | CH₃ | i-C₃H₇ | — |
| H | OC₆H₅ | CH₃ | i-C₃H₇ | — |
| H | CH₂Cl | CH₃ | i-C₃H₇ | — |
| CF₃ | H | CH₃ | i-C₃H₇ | — |
| H | C₂H₅ | CH₃ | i-C₃H₇ | — |
| H | CHO | CH₃ | i-C₃H₇ | — |
| H | CF₃ | CH₃ | i-C₃H₇ | — |
| H | SC₆H₅ | CH₃ | i-C₃H₇ | — |

EXAMPLE 8

Preparation of 5-(5-isopropyl-5-methyl-4-oxo-2-imidazolin-2-yl)thieno[3,2-b]pyridine-6-carboxylic acid

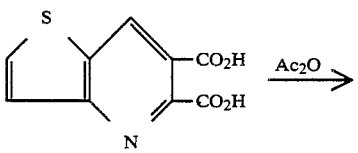

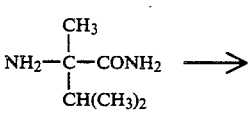

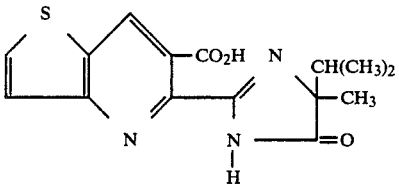

Thieno[3,2-b]pyridine-5,6-dicarboxylic acid (2.5 g, 0.011 mol) is heated slowly to 85° C. for one hour with acetic anhydride (25 mL), then cooled, filtered and washed with diethyl ether to give the anhydride as a solid, mp 266°–267° C. A mixture of the anhydride and 2-amino-2,3-dimethylbutyramide (2.6 g, 0.02 mol) in THF (70 mL) is stirred at room temperature for 15 hours. After heating at reflux for two hours, the mixture is cooled and diluted with THF (50 mL). Solid 5-[(1-carbamoyl-1,2-dimethylpropyl)carbamoyl]thieno[3,2-b]pyridine-6-carboxylic acid is filtered off, washed with ether and dried. The above solid is mixed with an aqueous 60 mL) solution of sodium hydroxide (6 g 0.05 mol) and heated at 85° C. for two hours and 30 minutes, then set aside at room temperature overnight. After cooling in an ice bath, the mixture is acidified to pH 3 with concentrated hydrochloric acid. A solid (3 g) is filtered off and dried. Crystallization from ethyl acetate affords (5-(5-isopropyl-5-methyl-4-oxo-2-imidazolin-2-yl)thieno[3,2-b]pyridine-6-carboxylic acid, mp 242°–244° C. in 46% yield.

Utilizing the above procedure and substituting the appropriate pyridine-5,6-dicarboxylic acid for thieno[3,2-b]pyridine-5,6-dicarboxylic acid yields the compounds illustrated below.

| Y | Z | mp °C. |
|---|---|---|
| H | H | 242–244 |
| H | Cl | 238–239 |
| H | Br | 226–227 |
| Cl | H | 247–248 |
| Cl | Cl | — |
| H | CH₃ | — |
| CH₃ | H | — |
| H | NO₂ | — |
| H | N(CH₃)₂ | — |
| H | SC₆H₅ | — |
| H | SCH₃ | — |
| H | OCH₃ | — |
| H | OCHF₂ | — |
| CH₃ | CH₃ | — |
| H | CH | — |
| H | SO₂N(CH₃)₂ | — |

-continued

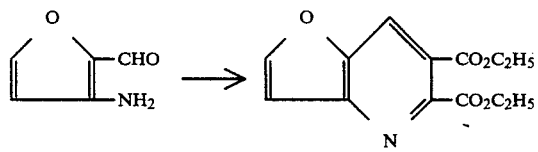

| Y | Z | mp °C. |
|---|---|---|
| C6H5 | H | — |
| —(CH2)3— | | — |
| —(CH2)4— | | — |
| —(CH2)4— | | — |
| H | C6H5 | — |
| H | OC6H5 | — |
| CF3 | H | — |
| C2H5 | H | — |
| H | C2H5 | — |
| H | I | — |
| H | F | — |
| H | CHO | — |
| H | CH2Cl | — |
| H | CF3 | — |

EXAMPLE 9

Preparation of diethyl furo[3,2-b]pyridine-5,6-dicarboxylate

3-Amino-2-formylfuran, prepared from 3-azido-2-formylfuran (8.9 g 0.065 mol) is dissolved in ethanol and to this solution diethyl oxalacetate (12.23 g, 0.065 mol) and ten drops of piperidine are added. In addition pulverized 3 A° molecular sieve is added and the reaction stirred at 65°-60° C. for three hours, then additional diethyl oxalacetate (2.2 g) is added. The reaction is essentially complete after 12 hours at 55°-60° C. On cooling the reaction is filtered, and the filtrate concentrated and then dissolved in ethyl acetate, water washed, then brine washed, dried over anhydrous magnesium sulfate and stripped to dryness. The residue is dissolved in 3:1 hexane:ethyl acetate and passed through a flash chromatographic column in two stages. First it is filtered by vacuum through a four to five inch pad of silica from which the last three fractions containing the required product are collected and combined. These combined fractions are then passed through a six inch column eluting under pressure with ethyl acetate:-hexane 3:1 and 2:1. Diethyl furo[3,2-b]pyridine-5,6-dicarboxylate 4.15 g (24%) is obtained after crystallization from hexane-ether, of mp 60°-64° C., and with a mass spectrum m/e of 264.

Utilizing the above procedure and substituting the appropriate furan for 3-amino-2-formylfuran yields the compounds illustrated below.

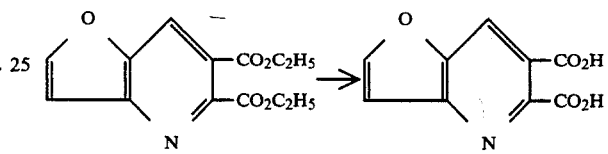

| Y | Z | R | mp °C. |
|---|---|---|---|
| H | H | C2H5 | 60-64 |
| H | Cl | C2H5 | — |
| CH3 | H | C2H5 | — |
| H | CH3 | C2H5 | — |
| C2H5 | H | C2H5 | — |
| H | C2H5 | C2H5 | — |
| CH3 | CH3 | C2H5 | — |

EXAMPLE 10

Preparation of furo[3,2-b]pyridine-5,6-dicarboxylic acid

Furo[3,2-b]pyridine-5,6-dicarboxylic acid, diethyl ester (1.1 g, 0.0042 mol) is dissolved in 95% ethanol (20 mL) containing 10% aqueous sodium hydroxide (20 mL) and set aside at 0° C. for two days. The mixture is cooled, acidified and the solvent removed under reduced pressure. Water 5 mL is added and the hydrated product diacid obtained as a brown solid by filtration, 3.31 g (99%), mp 183° C. (dec). Anal calcd. as $C_9H_5NO_5 \cdot 2\frac{1}{2}H_2O$ C, 42.86; H, 3.99; N, 5.55 found: C, 42.63; H, 2.63; N, 5.46.

Utilizing the above procedure and substituting the appropriate furo[3,2-b]pyridine-5,6-dicarboxylic ester yields the compounds illustrated below.

| Y | Z | R | mp °C. |
|---|---|---|---|
| H | H | H | 183 (dec) |
| H | Cl | C2H5 | — |
| CH3 | H | C2H5 | — |
| H | CH3 | C2H5 | — |
| C2H5 | H | C2H5 | — |
| H | C2H5 | C2H5 | — |
| CH3 | CH3 | C2H5 | — |

EXAMPLE 11

Preparation of furo[3,2-b]pyridine-5,6-dicarboxylic acid anhydride

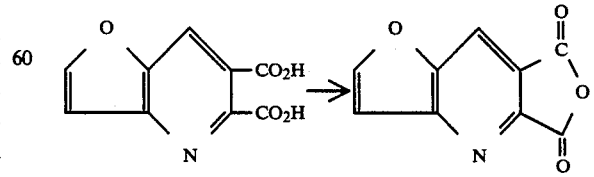

Furo[3,2-b]pyridine-5,6-dicarboxylic acid (3.3 g; 0.0159 mol) in acetic anhydride (100 mL) is heated to 70°-80° C. for six hours. The reaction mixture is cooled, filtered and the solid is washed with ether to give 3.01 (100%) of crude furo[3,2-b]pyridine-5,6-dicarboxylic acid anhydride.

Utilizing the above procedure and substituting the appropriate furo[3,2-b]pyridine-5,6-dicarboxylic acid yields the compounds illustrated below.

| Y | Z | mp °C. |
|---|---|--------|
| H | H | — |
| H | Cl | — |
| CH$_3$ | H | — |
| H | CH$_3$ | — |
| C$_2$H$_5$ | H | — |
| H | C$_2$H$_5$ | — |
| CH$_3$ | CH$_3$ | — |

EXAMPLE 12

Preparation of 5-[(1-carbamoyl-1,2-dimethylpropyl)-carbamoyl]-furo[3,2-b]pyridine-6-carboxylic acid and 5-(5-isopropyl-5-methyl-4-oxo-2-imidazolin-2-yl)furo[3,2-b]pyridine-6-carboxylic acid

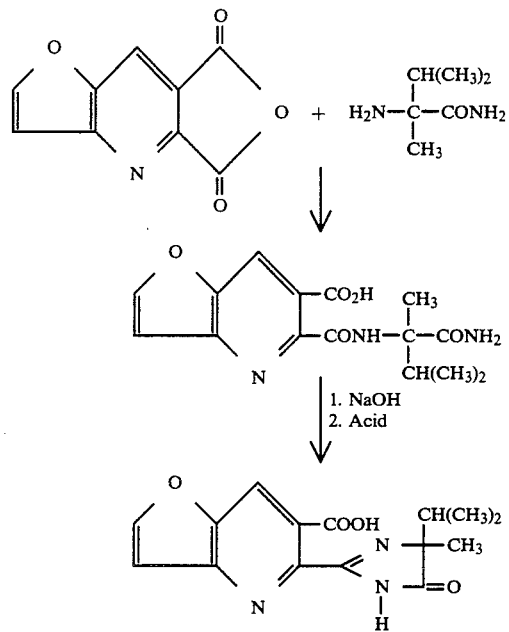

Furo[3,2-b]pyridine-5,6-dicarboxylic acid anhydride (3.01 g, 0.015 mol) is suspended in THF (100 mL) to which 2-amino-2,3-dimethylbutyramide (2.3 g, 0.018 mol) is added. After stirring for 20 hours, the solution is stripped to an oily solid which dissolves in a water/dilute sodium hydroxide solution. The alkaline solution is extracted with methylene chloride, and then acidified and reextracted with methylene chloride but on stirring only minute traces of material is isolated. The water layer is concentrated to an oily solid which is dissolved in ethanol, filtered and concentrated to a purple gum which is predominantly the crude product, 5-[(1-carbamoyl-1,2-dimethylpropyl)carbamoyl]furo[3,2-b]pyridine-6-carboxylic acid and is used without further purification to prepare the final 2-imidazolin-2-yl product by dissolving it in 10% sodium hydroxide solution (40 mL) and warming at 80° C. for three hours. On cooling the reaction is acidified and a small amount of solid precipitated out and was filtered off. Concentration of mother liquors gives a second crop, which is collected and combined with the first crop. Purification is effected by taking half of the material and separating on silica gel preparative glass plates as bands. The slower running band using methylene chloride:ethyl acetate:-chloroform:methanol 1:1:1:1 as eluant, affords the desired 2-imidazolin-2-yl product, mp 214°-223° C.(dec), Esters may then be prepared by the procedures described in Example 20.

Utilizing the above procedure and substituting the appropriate furo[3,2-b]pyridine-5,6-dicarboxylic anhydride yields the compounds illustrated below.

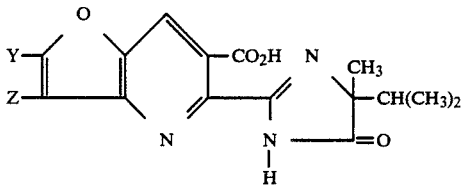

| Y | Z | mp °C. |
|---|---|--------|
| H | H | 214–223 (dec) |
| H | Cl | — |
| CH$_3$ | H | — |
| H | CH$_3$ | — |
| C$_2$H$_5$ | H | — |
| H | C$_2$H$_5$ | — |
| CH$_3$ | CH$_3$ | — |

EXAMPLE 13

Preparation of dimethyl thieno[2,3-b]pyridine-5,6-dicarboxylate

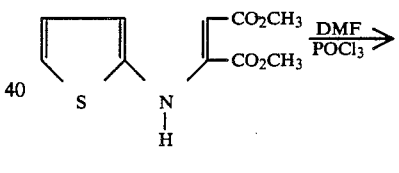

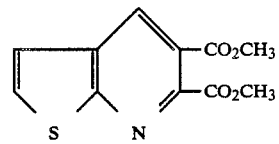

A Vilsmeier reagent is prepared by adding dropwise, with stirring, phosphorous oxychloride (40.29 g, 0.26 mol) to a cooled (10° C.) solution of DMF (19.0 g, 0.26 mol) in 1,2-dichloroethane (40 mL) in an N$_2$ atmosphere. This reagent is stirred at room temperature for one hour and 45 minutes. Dimethyl-2-thienylaminobutenedioate (63.4 g, 0.26 mol) dissolved in 1,2-dichloroethane (300 mL) is added dropwise to the Vilsmeier reagent at 7°–10° C. The reaction temperature is raised to room temperature for 15 minutes, then to reflux for 12 hours. The cooled reaction mixture is concentrated and the residue chromatographed on a silica gel column with ethyl acetate-hexane, affording dimethyl-thieno[2,3-b]pyridine-5,6-dicarboxylate (29 g, 45%) as a solid.

Utilizing the above procedure and substituting the appropriate dimethyl-2-thienylaminobutenedioate yields the compounds illustrated below.

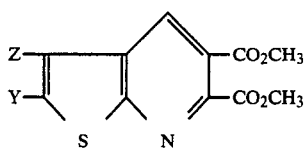

| Y | Z | mp °C. |
|---|---|---|
| CH₃ | H | 80–82 |
| H | H | 80–81 |
| H | CH₃ | — |
| CH₃ | CH₃ | — |
| H | C₆H₅ | — |
| C₆H₅ | H | — |
| CF₃ | H | — |
| —(CH₂)₄— | | 118–121.5 |

EXAMPLE 14

Preparation of dimethyl 3-bromothieno[2,3-b]pyridine-5,6-dicarboxylate

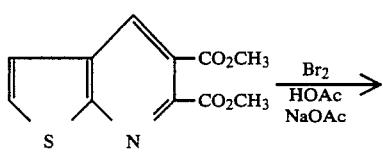

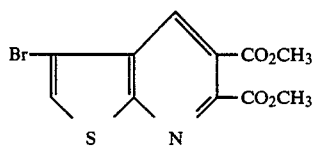

Bromine (0.33, 0.00206 mol) in acetic acid (8 mL) is added to a stirred solution of dimethylthieno[2,3-b]pyridine-5,6-dicarboxylate (0.5 g, 0.00187 mol) in acetic acid containing sodium acetate (0.31 g, 0.00377 mol) at 40° C. The reaction mixture is heated at 75° C. for 18 hours. Evaluation of the mixture by tlc (silica gel) indicated incomplete reaction. Additional bromine (0.33 g) in acetic acid and sodium acetate (0.31 g) is added and heating at 75° C. continued for six hours. The reaction mixture is diluted with water and extracted into ethyl acetate. The separated organic layer is dried over anhydrous MgSO₄, filtered, and the filtrate concentrated to an oil which solidifies on standing. Crystallization of the crude product from ethyl acetate-hexanes yields the dimethyl 3-bromothieno[2,3-b]pyridine-5,6-dicarboxylate as white needles mp 86°–87.5° C.

This compound may be readily converted to a variety of substituted-thieno[2,3-b]pyridine compounds as illustrated below, while electrophilic substitution such as nitration or halogenation yields additional compounds listed below.

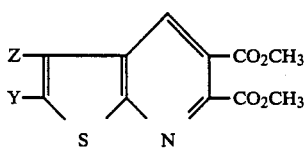

| Y | Z | mp °C. |
|---|---|---|
| H | H | — |
| H | Cl | 104–110 |
| H | Br | 86–87.5 |
| H | I | — |
| H | F | — |
| H | CN | — |
| H | SCH₃ | — |
| H | OCH₃ | — |
| H | N(CH₃)₂ | — |
| H | OCHF₂ | — |
| H | NO₂ | — |
| H | CHO | — |
| H | CH₂Cl | — |
| CH₃ | H | 80–82 |
| H | CH₃ | oil |
| Cl | H | — |
| Cl | Cl | 84–89 |
| CH₃ | CH₃ | — |
| H | SO₂N(CH₃)₂ | — |
| —(CH₂)₄— | | 118.5–121.5 |
| —(CH)₄— | | — |
| —(CH₂)₃— | | — |
| C₆H₅ | H | — |
| H | C₆H₅ | — |
| H | OC₆H₅ | — |
| CF₃ | H | — |
| H | SC₆H₅ | — |
| H | CF₃ | — |
| C₂H₅ | H | — |
| H | C₂H₅ | — |

EXAMPLE 15

Preparation of thieno[2,3-b]pyridine-5,6-dicarboxylic acid

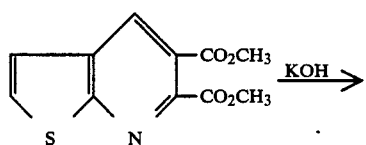

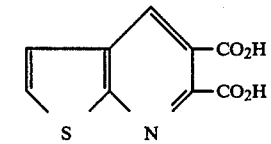

A solution containing dimethyl thieno[2,3-b]pyridine-5,6-dicarboxylate (27.75 g, 0.11 mol) and potassium hydroxide (30.98 g, 0.55 mol) in methanol (200 mL) under a N₂ atmosphere is heated at reflux for two hours. The reaction mixture is cooled and sufficient water added to dissolve any solids present before evaporating the mixture to dryness. The resulting solid is dissolved in a minimum volume of water, cooled in an ice bath and acidified with concentrated H₂SO₄ to pH ~ 1. Thieno[2,3-b]pyridine-5,6-dicarboxylic acid is filtered off and dried overnight to give 23.36 g mp 272°–275° C.

Utilizing the above procedure and substituting the appropriate substituted dialkylthieno[2,3-b]pyridine-5,6-dicarboxylate yields the compounds illustrated below.

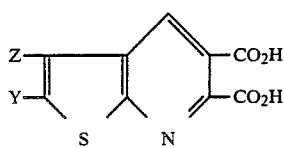

| Y | Z | mp °C. |
|---|---|---|
| H | H | 272–275 |
| H | Cl | >300 |
| H | Br | >315 |
| H | I | — |
| H | F | — |
| H | CN | — |
| H | SCH₃ | — |
| H | OCH₃ | — |
| H | N(CH₃)₂ | — |
| H | OCHF₂ | — |
| H | NO₂ | — |
| H | CHO | — |
| H | CH₂Cl | — |
| H | CH₃ | 180–183 (dec) |
| CH₃ | H | — |
| Cl | H | — |
| Cl | Cl | — |
| CH₃ | CH₃ | — |
| C₆H₅ | H | — |
| H | SO₂N(CH₃)₂ | — |
| —(CH₂)₃— | | — |
| —(CH₂)₄— | | 280–290 |
| —(CH)₄— | | — |
| H | OC₆H₅ | — |
| H | C₆H₅ | — |
| CF₃ | H | — |
| H | CF₃ | — |
| H | SC₆H₅ | — |
| C₂H₅ | H | — |
| H | C₂H₅ | — |

EXAMPLE 16

Preparation of thieno[2,3-b]pyridine-5,6-dicarboxylic anhydride

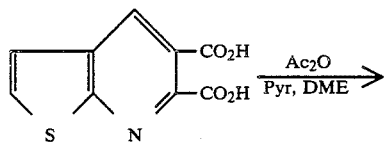

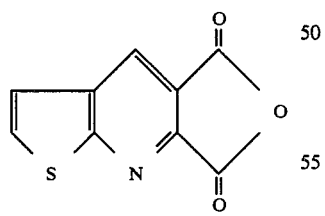

Acetic anhydride (37.4 g, 0.366 mol) is added to a stirred suspension of thieno[2,3-b]pyridine-5,6-dicarboxylic acid (21.52 g, 0.096 mol) in dimethoxyethane (175 mL) in an inert N₂ atmosphere. Upon addition of pyridine (16.78 g, 0.21 mol) at room temperature an exotherm to 45° C. is observed and a homogeneous solution results. The reaction mixture is then stirred at room temperature and the resulting solid filtered off, washed with ether and air dried to give 14.8 g (75%) of thieno[2,3-b]pyridine-5,6-dicarboxylic acid anhydride.

Utilizing the above procedure and substituting the appropriate substituted thieno[2,3-b]pyridine-5,6-dicarboxylic acid yields the compounds illustrated below.

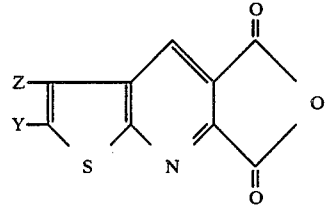

| Y | Z | mp °C. |
|---|---|---|
| CH₃ | H | 176–180 |
| H | Br | 228.5–231 |
| H | Cl | 230–300 (slow dec) |
| H | H | 210–213 |
| H | I | — |
| H | F | — |
| H | CN | — |
| H | SCH₃ | — |
| H | N(CH₃)₂ | — |
| H | NO₂ | — |
| H | CHO | — |
| H | CH₂Cl | — |
| H | CH₃ | — |
| Cl | H | — |
| Cl | Cl | — |
| CH₃ | CH₃ | — |
| C₆H₅ | H | — |
| H | SO₂N(CH₃)₂ | — |
| —(CH₂)₃— | | — |
| —(CH₂)₄— | | 220–222 |
| —(CH)₄— | | — |
| H | C₆H₅ | — |
| H | OC₆H₅ | — |
| CF₃ | H | — |
| H | CF₃ | — |
| H | OCHF₂ | — |
| H | SC₆H₅ | — |
| H | OCH₃ | — |
| C₂H₅ | H | — |
| H | C₂H₅ | — |

EXAMPLE 17

Preparation of 6-[(1-carbamoyl-1,2-dimethylpropyl)carbamoyl]-thieno[2,3-b]pyridine-5-carboxylic acid

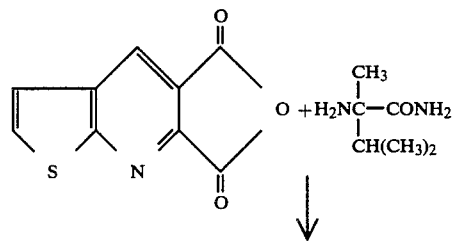

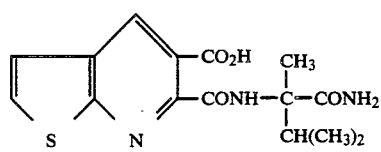

2-Amino-2,3-dimethylbutyramide (9.84 g, 0.076 mol) is added to a stirred suspension of thieno[2,3-b]pyridine-5,6-dicarboxylic acid anhydride (14.8 g, 0.072 mol) in THF under an inert atmosphere of N₂ at room temperature. The dark solution is stirred at room temperature overnight and the resulting solid filtered off, washed with THF and air dried to give 17.35 g (72%) of 6-[(1-carbamoyl-1,2-dimethylpropyl)carbamoyl]thieno[2,3-b]pyridine-5-carboxylic acid.

Utilizing the above procedure and substituting the appropriate substituted thieno[2,3-b]pyridine-5,6-dicarboxylic acid anhydride yields the compounds illustrated below.

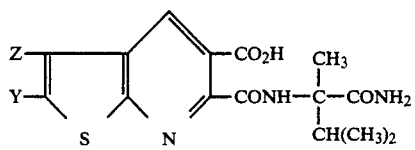

| Y | Z | mp °C. |
|---|---|---|
| CH₃ | H | 207–208 |
| H | Br | 176–178 |
| H | Cl | 156–158 |
| H | H | — |
| H | I | — |
| H | F | — |
| H | CN | — |
| H | SCH₃ | — |
| H | OCH₃ | — |
| H | N(CH₃)₂ | — |
| H | NO₂ | — |
| H | CHO | — |
| H | CH₂Cl | — |
| H | CH₃ | — |
| Cl | H | — |
| Cl | Cl | — |
| CH₃ | CH₃ | — |
| C₆H₅ | H | — |
| H | SO₂N(CH₃)₂ | — |
| —(CH₂)₃— | | — |
| —(CH₂)₄— | | solid |
| —(CH)₄— | | — |
| H | C₆H₅ | — |
| H | OC₆H₅ | — |
| CF₃ | H | — |
| H | OCHF₂ | — |
| H | CF₃ | — |
| H | SC₆H₅ | — |
| C₂H₅ | H | — |
| H | C₂H₅ | — |

EXAMPLE 18

Preparation of 6-(5-isopropyl-5-methyl-4-oxo-2-imidazolin-2-yl)thieno[2,3-b]pyridine-5-carboxylic acid

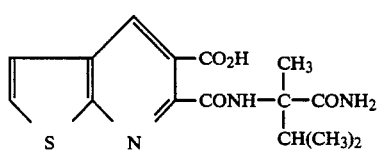

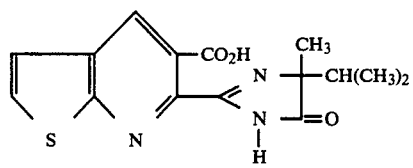

6-[(1-Carbamoyl-1,2-dimethylpropyl)carbamoyl]-thieno[2,3-b]pyridine-5-carboxylic acid (17.35 g, 0.052 mol) is added to water (225 mL) containing sodium hydroxide (10.35 g, 0.26 mol). The resulting basic solution is heated at 80° C. for two hours and 45 minutes, cooled in an ice-water bath and acidified with 6N H₂SO₄. The product 6-(5-isopropyl-5-methyl-4-oxo-2-imidazolin-2-yl)thieno[2,3-b]pyridine-5-carboxylic acid is filtered off, washed with water and air dried yielding 1.54 g, 70.3%, mp 221°–223° C.

EXAMPLE 19

Preparation of 5H-Imidazo[1',2':1,2]pyrrolo[3,4-b]thieno[3,2-e]pyridine-3(2H),5-dione, 2-isopropyl-2-methyl

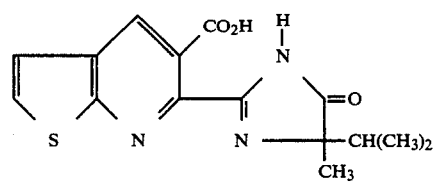

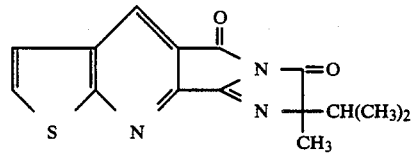

Dicyclohexylcarbodiimide (1.07 g, 0.005 mol) in methylene chloride (20 mL) is added dropwise to a stirred methylene chloride (30 mL) suspension of 6-(5-isopropyl-5-methyl-4-oxo-2-imidazolin-2-yl)thieno[2,3-b]-5-carboxylic acid (1.5 g, 0.0047 mol) under an N₂ atmosphere. After stirring the reaction mixture for 16 hours, it was clarified by filtration, concentrated to dryness and the resulting material purified by column chromatography on silica gel eluting with acetonitrile/methylene chloride (½). The solid product was crystallized from toluene to give the pure 3,5-dione as white crystals mp 214.5°–216.5° C.

EXAMPLE 20

Preparation of 2-propynyl 6-(5-isopropyl-5-methyl-4-oxo-2-imidazolin-2-yl)thieno[2,3-b]pyridine-5-carboxylate

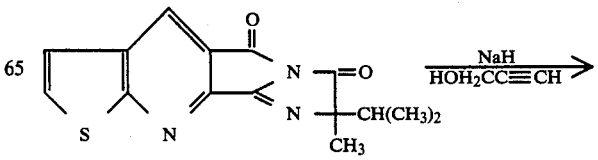

-continued

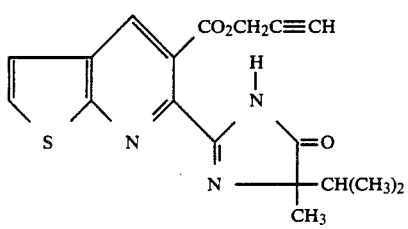

Sodium hydride (2.4 g, 60%, 0.126 mol) is added to the 3,5-dione (0.9 g, 0.003 mol) in propargyl alcohol (25 mL) at 10° C. under an inert N₂ atmosphere. The reaction mixture is stirred at room temperature for 60 hours and then neutralized with a saturated ammonium chloride solution. The resulting mixture is concentrated on a rotary evaporator, diluted with water and extracted with ethyl acetate. The organic layer is separated, dried over anhydrous MgSO₄ and concentrated to dryness.

Purification of the product by column chromatography on silica gel with methylene chloride/acetonitrile (85/15) yields 2-propynyl 6-(5-isopropyl-5-methyl-4-oxo-2-imidazolin-2-yl)pyridine-5-carboxylate, which after crystallization from toluene has a mp 188°–189.5° C.

Utilizing the procedures of Examples 18, 19 and 20 and substituting the appropriate thieno[3,2-b]pyridine or thieno[2,3-b]pyridine compounds, yields the compounds illustrated below.

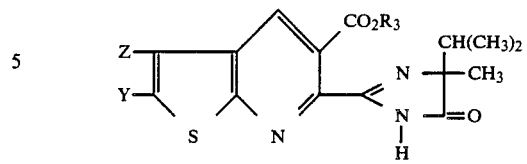

| Y | Z | R₃ | mp °C. |
|---|---|---|---|
| H | H | CH₃ | 215–217 |
| H | H | H | 220–223.5 (dec) |
| H | H | —CH₂C≡CH | 188–189.5 |
| H | H | —CH₂—[furanyl] | 140–142 |
| H | H | —CH₂C(CH₃)=CH₂ | 108–110 |
| CH₃ | H | H | 225.5–227.5 |
| H | Br | H | 274–276 |
| H | Cl | H | 266–267 |
| H | NO₂ | —CH₃ | 201–202.5° C. |
| H | NO₂ | H | 260 (dec) |
| Cl | H | H | — |
| Cl | Cl | H | — |
| H | CH₃ | H | — |
| H | N(CH₃)₂ | H | — |
| H | SCH₃ | H | — |
| H | OCH₃ | H | — |
| H | OCHF₂ | H | — |
| CH₃ | CH₃ | H | — |
| H | CN | H | — |
| H | SO₂N(CH₃)₂ | H | — |
| C₆H₅ | H | H | — |
| H | C₆H₅ | H | — |
| —(CH₂)₃— | | H | — |
| —(CH₂)₄— | | H | — |
| —(CH₂)₄— | | H | — |
| H | OC₆H₅ | H | — |
| CF₃ | H | H | — |
| C₂H₅ | H | H | — |
| H | C₂H₅ | H | — |
| H | I | H | — |
| H | F | H | — |
| H | CHO | H | — |
| H | CH₂Cl | H | — |
| H | CF₃ | H | — |
| H | SC₅H₆ | H | — |

| Y | Z | R₃ | mp °C. |
|---|---|---|---|
| H | H | H | 242–244 |
| H | Cl | H | 238–239 |
| H | Br | H | 226–227 |
| H | H | —CH₂—[furanyl] | 156–157 |
| Cl | H | H | 266–267 |
| Cl | I | H | — |
| H | CH₃ | H | — |
| H | F | H | — |
| CH₃ | H | H | — |
| Cl | Cl | H | — |
| H | NO₂ | H | — |
| H | N(CH₃)₂ | H | — |
| H | SCH₃ | H | — |
| H | OCH₃ | H | — |
| CH₃ | CH₃ | H | — |
| H | CHO | H | — |
| H | OCHF₂ | H | — |
| H | CN | H | — |
| H | SO₂N(CH₃)₂ | H | — |
| C₆H₅ | H | H | — |
| H | C₆H₅ | H | — |
| —(CH₂)₃— | | H | — |
| —(CH₂)₄— | | H | — |
| —(CH₂)₄— | | H | — |
| H | OC₆H₅ | H | — |
| CF₃ | H | H | — |
| H | CF₃ | H | — |
| C₂H₅ | H | H | — |
| H | C₂H₅ | H | — |
| H | CH₂Cl | H | — |
| H | SC₆H₅ | H | — |

EXAMPLE 21

Preparation of methyl 6-(4-isopropyl-4-methyl-5-oxo-2-imidazolin-2-yl)-3-nitrothieno[2,3-b]pyridine-5-carboxylate

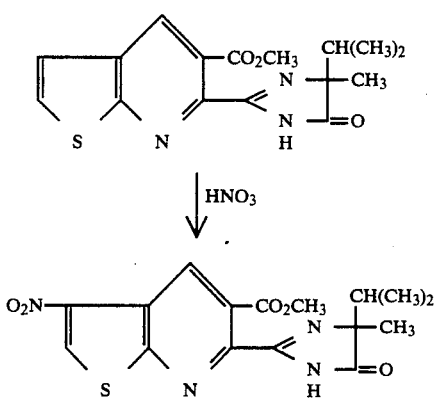

Methyl 6-(4-isopropyl-4-methyl-5-oxo-2-imidazolin-2-yl)thieno[2,3-b]pyridine-5-carboxylate (3.94 g, 0.0119 mol) is dissolved in 200 mL concentrated $H_2SO_4$ at room temperature. While cooling to 3° C. in an ice bath, 1.5 mL (0.024 mol) concentrated $HNO_3$ is added, then the mixture is allowed to warm to room temperature. After three hours, the reaction mixture is poured onto ice, neutralized with solid $NaHCO_3$ to pH 6 and is extracted with methylene chloride. The extract is filtered, then dried over sodium sulfate, refiltered and concentrated to a yield solid weighing 4.33 g (97%), which upon crystallization from methanol water has mp 201°–202.5° C.

EXAMPLE 22

Preparation of 6-(4-isopropyl-4-methyl-5-oxo-2-imidazolin-2-yl)-3-nitrothieno[2,3-b]pyridine-5-carboxylic acid

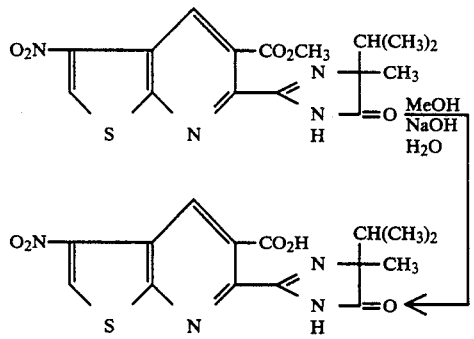

The ester (1.0 g, 0.00266 mol) from Example 21 is stirred in 100 mL methanol and 10 mL 10% sodium hydroxide solution for 24 hours. Water (25 mL) is added and the methanol removed in vacuo. Acidification of the aqueous layer gives a brown precipitate which upon filtration and crystallization from methanol-water has mp 260° C.

EXAMPLE 23

Preparation of diethyl 5-acetyl-1,6-dihydro-6-oxo-2,3-pyridinedicarboxylate

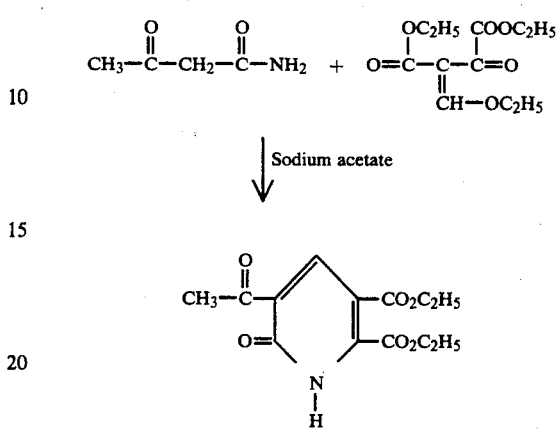

Sodium acetate (30 g, 0.37 mol) is added to a stirred mixture of diethyl(ethoxymethylene)oxalacetate (87 g, 0.36 mol) and acetoacetamide (36 g, 0.36 mol) in absolute ethanol (300 mL). After stirring the reaction mixture for 30 minutes, the ethanol is distilled off under reduced pressure, the residue acidified to pH 2 with dilute aqueous hydrochloric acid and the resulting solid filtered off. Crystallization from an ethanol-water mixture affords diethyl 5-acetyl-1,6-dihydro-6-oxo-2,3-pyridinedicarboxylate as crystals mp 101°–110° C.

EXAMPLE 24

Preparation of isobutyryl acetonitrile

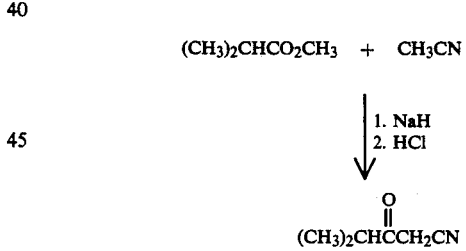

NaH (61.55 g of 60% dispersion, 1.54 mol) is added to 650 mL anhydrous THF under $N_2$. The suspension is heated to reflux. Methyl isobutyrate (100 g, 98 mol) and acetonitrile (63.16 g, 1.54 mol) are mixed in 140 mLs anhydrous THF and added dropwise over one hour to the refluxing suspension. The resulting solution is refluxed for 16 hours. Enough water is added to the reaction mixture to dissolve the salt that is formed. The THF is removed in vacuo, and the basic aqueous solution is extracted with ether, then acidified to pH 4 with concentrated HCl. The solution is extracted with ether. The extracts are washed with brine and dried over anhydrous $MgSO_4$, filtered and the solvent is removed in vacuo, giving 97.25 g, (89.4%) of the title product an orange oil.

EXAMPLE 25

Preparation of diethyl-5-(2-methylpropionyl)-1,6-dihydro-6-oxo-2,3-pyridinedicarboxylate

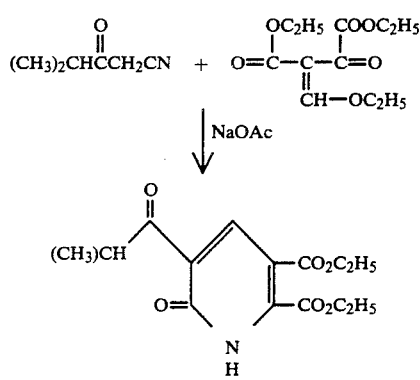

Isobutyl acetonitrile (50 g, 0.45) 24 and diethyl(ethoxymethylene)oxalacetate (110 g, 0.45 mol) are dissolved in absolute ethanol and then is added sodium acetate (36.9 g, 0.45 mol) and one drop of piperidine. After 12 hours, the mixture is concentrated, acidified with dilute hydrochloric acid then extracted with methylene chloride. The extracts are concentrated and recrystallized to give the title product as a white solid 21.7 g (19.5%) mp 116°–118° C.

EXAMPLE 26

Preparation of diethyl 5-(bromoacetyl)-1,6-dihydro-6-oxo-2,3-pyridinedicarboxylate

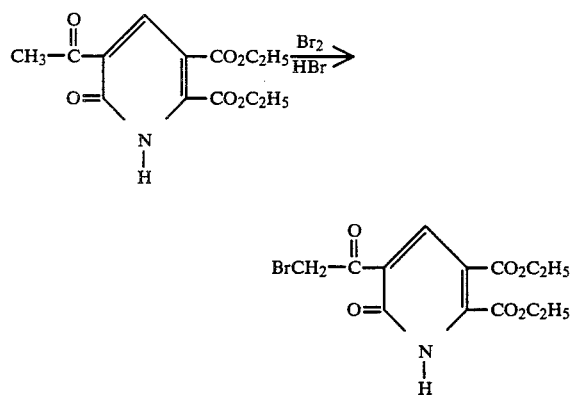

Bromine (8.0 g, 0.050 mol) in 48% HBr is added dropwise to a stirred solution of diethyl-5-acetyl-1,6-dihydro-6-oxo-2,3-pyridinedicarboxylate (14.05 g, 0.05 mol) in 48% HBr (200 mL). Upon completion of this bromine addition the reaction mixture is poured onto ice (200 g) and the mixture is stirred until the ice has melted. The crude product is collected by filtration and crystallized twice from an ethyl acetate-hexane mixture (½) affording diethyl 5-(bromoacetyl)-1,6-dihydro-6-oxo-2,3-pyridinedicarboxylate with mp 141°–142° C.

Utilizing the the above procedure using diethyl 2-methylpropionyl-2-pyridone-dicarboxylate yields diethyl 5-(2-bromo-2-methylpropionyl)-1,6-dihydro-6-oxo-2,3-pyridinedicarboxylate, mp 124°–126° C.

EXAMPLE 27

Preparation of diethyl 5-(2-bromo-1-hydroxyethyl)-1,6-dihydro-6-oxo-2,3-pyridinedicarboxylate and diethyl 2,3-dihydro-3-hydroxy-furo[2,3-b]pyridine-5,6-dicarboxylate

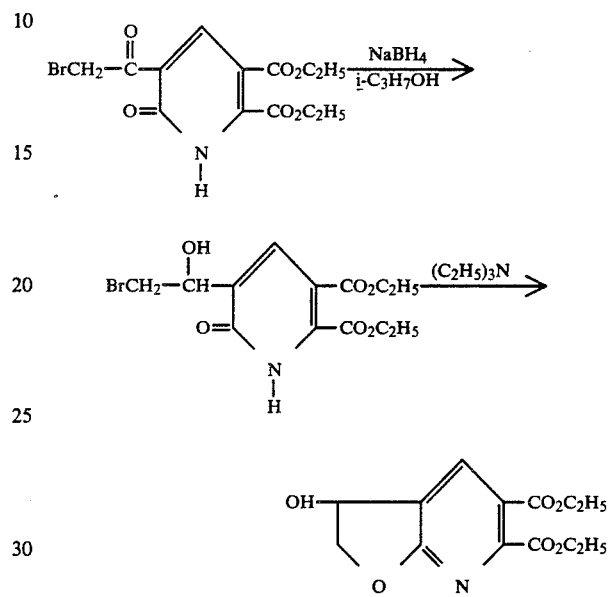

Sodium borohydride (2.54 g, 0.066 mol) is added in portions over a 30 minute period to a stirred suspension of diethyl 5-(bromoacetyl)-1,6-dihydro-6-oxo-2,3-pyridinedicarboxylate (57.2 g, 0.159 mol) at 10°–20° C. Upon completion of the sodium borohydride addition, the reaction mixture is stirred while attaining room temperature. Ice (100 g) is added and the mixture stirred until the ice has melted. The mixture is then concentrated in vacuo and the residue crystallized twice from an ethyl acetate-hexane mixture to give pure diethyl 5-(2-bromo-1-hydroxyethyl)-1,6-dihydro-6-oxo-2,3-pyridinedicarboxylate mp 134°–138° C. Stirring this compound with triethylamine (1.0 mL/g of solid) in methylene chloride for one hour, followed by washing the organic solution with dilute hydrochloric acid, water, brine and drying over anhydrous $MgSO_4$ yields the crude furo[2,3-b]pyridine as an oil upon removing the solvent in vacuo. Crystallization from a cyclohexane-toluene mixture affords pure diethyl 2,3-dihydro-3-hydroxy-furo[2,3-b]pyridine-5,6-dicarboxylate mp 73°–77° C.

EXAMPLE 28

Preparation of diethyl 2,3-dihydro-3-methoxyfuro[2,3-b]pyridine-5,6-dicarboxylate

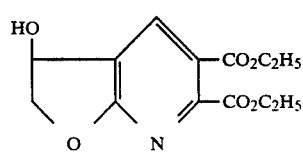

EXAMPLE 30

Preparation of dimethyl 2-methyl-furo[2,3-b]pyridine-5,6-dicarboxylate

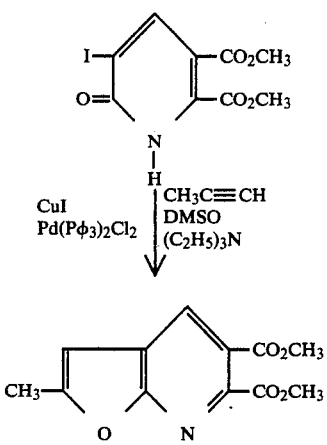

Propyne (3.0 mLs, 0.045 mol) is condensed in a graduated cylinder in a dry ice/acetone bath and added to a stirred suspension of dimethyl 1,6-dihydro-5-iodo-6-oxo-2,3-pyridinedicarboxylate (13.48 g, 0.04 mol), cuprous iodide (0.38 g, 0.002 mol) and bis(triphenylphosphine)palladium II) chloride (2.81 g, 0.004 mol) in 150 mLs DMSO and 50 mLs triethylamine at 10° C. After addition of the propyne the reaction mixture is stirred at room temperature for 60 hours. Water is added and the mixture is extracted with ethyl acetate. The ethyl acetate solution is washed with water and dried over anhydrous MgSO$_4$, then concentrated in vacuo to give a mixture of materials. The crude product is isolated by flash column chromatography using 9:1 methylene chloride:ethyl acetate. The fractions containing the title product are concentrated in vacuo and the residue is recrystallized from cyclohexane to give the pure compound mp 115°–118° C.

Utilizing the above procedure and substituting the appropriate substituted acetylene yields the compounds illustrated below.

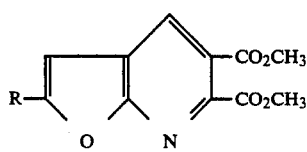

| R | mp °C. |
|---|---|
| $C_2H_5$ | 147–149 |
| Phenyl | 152–153 |

---

-continued

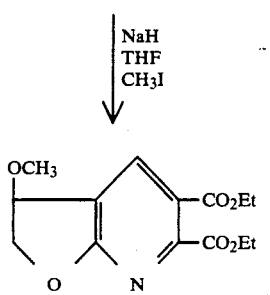

Sodium hydride, 60% dispersion in mineral oil (2.05 g, 0.0512 mol) and iodomethane (7.9 mL, 0.128 mol) are added to a solution of the hydroxy diester of Example 27 (12.00 g, 0.0427 mol) in tetrahydrofuran (400 mL) under N$_2$. After stirring overnight at room temperature, the reaction is heated to 50° C. under a stream of N$_2$ to remove excess iodomethane. The reaction is then cooled, filtered, stripped and chromatographed over silica gel. Eluting with hexane/ethyl acetate (4:1) gives the product as a yellow oil in 57.3% yield. Calcd. for $C_{14}H_{17}NO_6$; C, 56.94; 4,5.80, N, 4.74. Found: C, 56.93; H, 5.59; N, 4.83.

EXAMPLE 29

Preparation of diethyl furo[2,3-b]pyridine-5,6-dicarboxylate

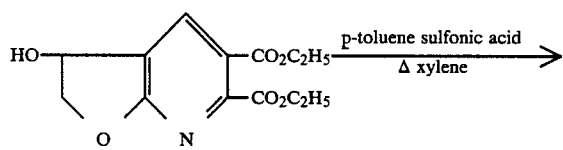

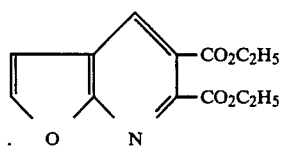

A xylene solution of the hydroxy-furo compound obtained in Example 23, (3.7 g) containing para-toluene sulfonic acid (0.01 g) is heated at reflux for two hours. The solution is cooled and the xylene solution decanted off. The residue is extracted with ether and the extracts combined with the xylene. Distillation of the solvents gives a yellow solid which is crystallized from a cyclohexane-toluene mixture to give pure diethyl furo[2,3-b]pyridine-5,6-dicarboxylate mp 66°–77° C.

EXAMPLE 31

Preparation of diethyl 2,3-dihydro-3,3-dimethylfuro[2,3-b]pyridine-5,6-dicarboxylate

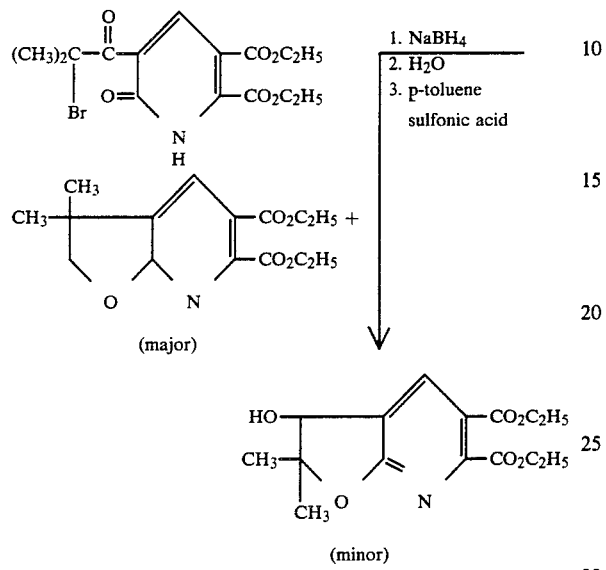

The 5-(2-bromo-2-methylpropy ketone diester of Example 26 (20 g, 0.052 mol) is dissolved in 200 mL absolute ethanol and 3.0 g sodium borohydride (0.078 mol) is added at 0° C., the temperature is then allowed to rise gradually to 15° C. After the mixture is stirred for one additional hour, the ethanol is removed in vacuo. The solidified mass is treated with water and extracted with methylene chloride. The organic extract is then washed with water and a saturated sodium chloride solution, dried and concentrated. The residue, weighing 12 g is redissolved in xylene and 1.0 g p-toluenesulfonic acid is added. The solution is refluxed for 12 hours then cooled. The xylene solution is decanted and the residue washed with several portions of ether. The combined organic solutions are concentrated then chromatographed with 9:1 methylene chloride/ethyl acetate to obtain 3.2 g of the oily diester (21%); mass spectrum M+1/e=294.

From a later chromatographic fraction is obtained 1.4 g of 2,2-dimethyl-3-hydroxyfuro[2,3-b]pyridine-5,6-dicarboxylate (11.5%).

EXAMPLE 32

Preparation of diethyl 3-bromofuro[2,3-b]pyridine-5,6-dicarboxylate

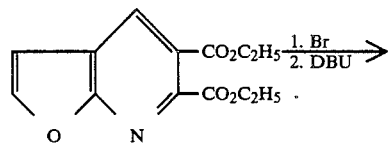

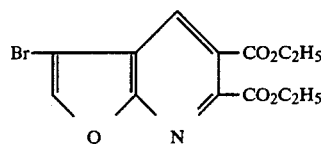

The diester of Example 29 (6.0 g, 0.0228 mol) is dissolved in 200 mL methylene chloride containing 4.6 g sodium acetate, and bromine is added (7.3 g, 0.0556 mol) at reflux. Following the addition, the mixture was stirred for 15 minutes at reflux, then cooled, washed with aqueous sodium bisulfite, dried with sodium sulfate and filtered. The filtrate was stripped to 8.8 g of the crude dibromo compound which was redissolved in methylene chloride and treated with 3.16 g DBU (0.021 mol) at room temperature for 30 minutes. The mixture was then concentrated in vacuo, and chromatographed over silica gel with hexaneethylacetate to give 7.1 g (90%) of the diethyl 3-bromofuro[2,3-b]pyridine-5,6-dicarboxylate mono bromo diester mp 49.5°–52° C.

EXAMPLE 33

Preparation of diethyl 2,3-dibromofuro[2,3-b]pyridine-5,6-dicarboxylate

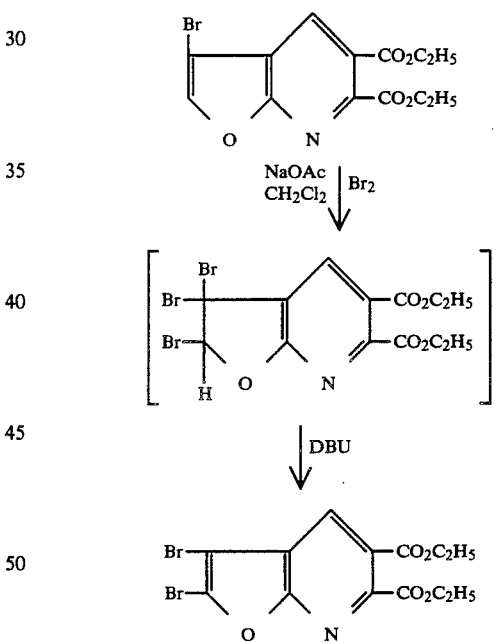

Sodium acetate (2.40 g, 0.0292 mol) and bromine (7.5 mL, 0.146 mol) are added to a solution of diethyl 3-bromofuro[2,3-b]pyridine-5,6-dicarboxylate (5.00 g, 0.0146 mol) in methylene chloride (150 mL). The mixture is stirred at room temperature for four days then washed with aqueous sodium bisulfate to remove unreacted bromine. The aqueous solution is then back extracted with methylene chloride. The organic solution is combined, dried over sodium sulfate and filtered. To the filtrate is added 1,8-diazabicyclo[5.4.0]undec-7-ene(4.4 mL, 0.032 mol), and the mixture is stirred at room temperature for one hour. The solution is then concentrated in vacuo. The residue is chromatographed over silica gel eluting with 20% ethyl acetate in hexane, yielding the crude 2,3-dibromofuro[2,3-b]pyridine as a white solid in 95% yields recrystallization from a methylene chloride-hexane mixture affords diethyl 2,3-dibromofuro[2,3-b]pyridine-5,6-dicarboxylate mp 96°–98° C. in 75.9% recrystallized yield.

EXAMPLE 34

Preparation of diethyl 3-trifluoromethylfuro[2,3-b]pyridine-5,6-dicarboxylate

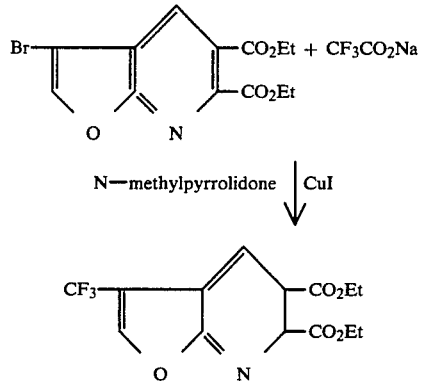

To a solution of sodium trifluoroacetate (0.0234 mol) in N-methylpyrrolidone (50 mL) is added 3-bromofuropyridine of Example 32 (2.02, 0.00585 mol) and cuprous iodide (2.2 g, 0.0119 mol). The mixture is heated to 160° C. for three hours under $N_2$, cooled to room temperature, treated with EtOAc (100 mL) and hexene (100 mL), and filtered. The filtrate is washed with $H_2O$ (4×200 mL), dried over $Na_2SO_4$ and stripped to an oil which is chromatographed over silica gel with hexane-ETOAc (7:3) elution. The product is collected as a pale yellow solid; mp 50°–55° C.

EXAMPLE 35

Preparation of furo[2,3-b]pyridine-5,6-dicarboxylic acid

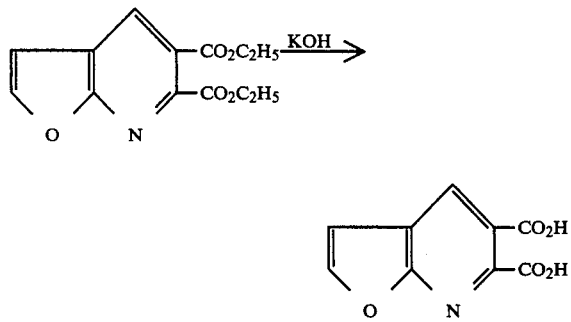

Potassium hydroxide (5.60 g, 85%, 0.087 mol) in water (5 mL) is added to a stirred suspension of diethyl furo[2,3-b]pyridine-5,6-dicarboxylate (9.3 g, 0.035 mol) in absolute ethanol (100 mL). The reaction mixture is heated at 60° C. for one hour, then cooled and anhydrous acetone added. The precipitate is filtered off, dried, suspended in dry acetone and treated with hydrogen chloride to adjust to a pH of 2. Crystallization of the isolated solids from an ethyl acetateacetone mixture affords furo[2,3-b]pyridine-5,6-dicarboxylic acid mp 189°–192° C.

EXAMPLE 36

Preparation of furo[2,3-b]pyridine-5,6-dicarboxylic anhydride

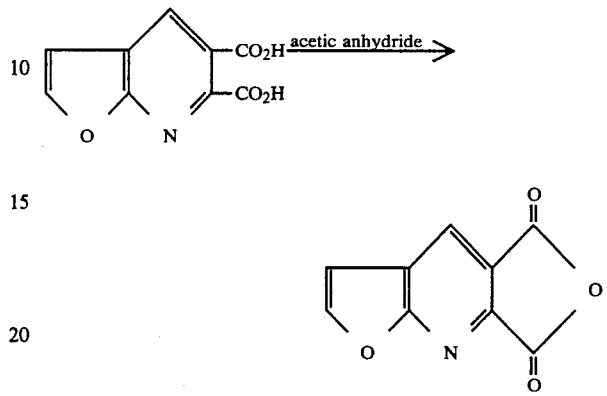

Furo[2,3-b]pyridine-5,6-dicarboxylic acid (6.7 g, 0.032 mol) is heated at 60° C. for 30 minutes in acetic anhydride (150 mL). The reaction mixture is cooled to room temperature and concentrated in vacuo and the residue triturated with cyclohexane-ether(5:1), filtered off and dried to give 5.35 g furo[2,3-b]pyridine-5,6-dicarboxylic acid anhydride.

EXAMPLE 37

Preparation of 6-[(1-carbamoyl-1,2-dimethylpropyl)carbamoyl]-furo[2,3-b]pyridine-5-carboxylic acid

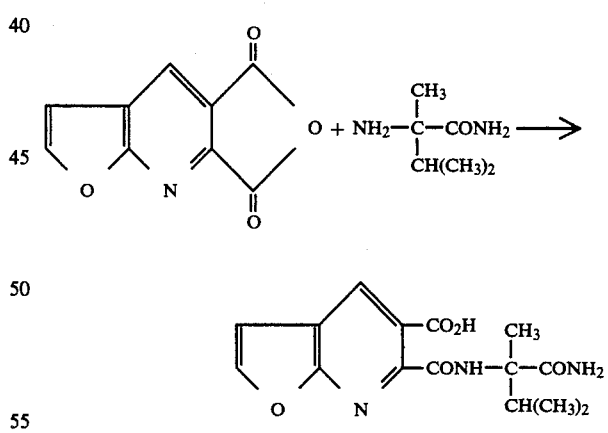

2-Amino-2,3-dimethylbutyramide (2.1 g, 0.016 mol) is added to a stirred suspension of furo[2,3-b]pyridine-5,6-dicarboxylic acid anhydride (3.0 g, 0.016 mol) in tetrahydrofuran (7.5 mL) and the mixture allowed to stirr at room temperature for 16 hours. The reaction mixture is then stirred at 60° C. for one hour, cooled to room temperature, ether added, and the solid filtered off and dried to give 5 g of 6-[(1-carbamoyl-1,2-dimethylpropyl)carbamoyl]furo[2,3-b]pyridine-5-carboxylic acid mp 192°–196° C. (dec).

EXAMPLE 38

Preparation of
6-(4-isopropyl-4-methyl-5-oxo-2-imidazolin-2-yl)furo[2,3-b]pyridine-5-carboxylic acid

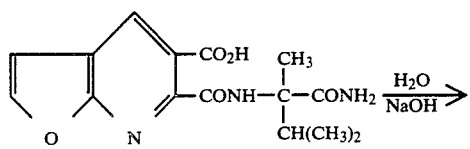

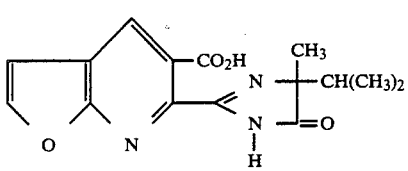

A solution containing 6-[(1-carbamoyl-1,2-dimethylpropyl)carbamoyl]furo[2,3-b]pyridine-5-carboxylic acid (3.8 g, 0.012 mol) in aqueous sodium hydroxide 2.4 g, 0.06 mol) in water (40 mL) is stirred at 65° C. for three hours. The reaction mixture is then heated at 75° C. for one hour, allowed to cool, poured into ice, acidified to pH 2–3 and the resulting solid filtered off and dried. Crystallization from an acetone-methanol mixture affords pure 6-(4-isopropyl-4-methyl-5-oxo-2-imidazolin-2-yl)furo[2,3-b]pyridine-5-carboxylic acid mp 237°–244° C.

EXAMPLE 39

Preparation of
6-(4-isopropyl-4-methyl-5-oxo-2-imidazolin-2-yl)-3-nitrofuro[2,3-b]pyridine-5-carboxylic acid

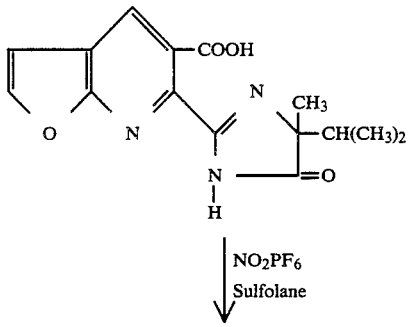

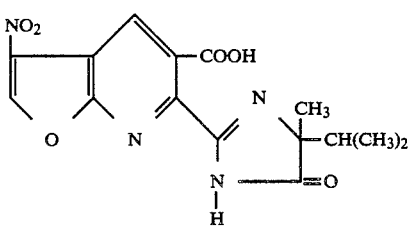

Nitryl hexafluorophosphate (0.75 g, 0.00391 mol) is added to a suspension of 6-(4-isopropyl-4-methyl-5-oxo-2-imidazolin-2-yl)-furo[2,3-b]pyridine-5-carboxylic acid (1.07 g, 0.00355 mol) in sulfolane (63 mL) under nitrogen. The temperature of the reaction is maintained between 64° C. and 85° C. for three days during which time the solids dissolve. The mixture is cooled to 30° C. and chromatographed over silica gel. Elution with 1:1 hexane to ethyl acetate removes the sulfolane. Elution with 1% to 10% methanol in methylene chloride followed by recrystallization from acetone-hexane yields 6-(4-isopropyl-4-methyl-5-oxo-2-imidazolin-2-yl)-3-nitro-furo[2,3-b]pyridine-5-carboxylic acid, mp 220°–237° C.

EXAMPLE 40

Preparation of
2-isopropyl-2-methyl-5H-furo[2,3-b]imidazo[2',1':5,1-]pyrrolo[3,4-e]pyridine-3(2H),5-dione

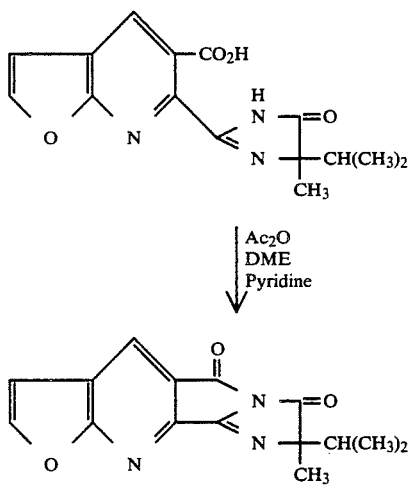

To a suspension of 6-(4-isopropyl-4-methyl-5-oxo-2-imidazolin-2-yl)-furo[2,3-b]-pyridine-5-carboxylic acid (11.7 g, 0.039 mol) in 100 mL dimethoxyethane (DME) is added 7.3 mL acetic anhydride and 3.9 mL pyridine. After stirring 24 hours at room temperature, the solids are filtered and washed with ether and the mother liquor is concentrated by adding xylene to aid removal of pyridine. The residue is triturated with ether to obtain solids which are combined with the first crop to give 11.1 g (100%) of product. Recrystallization from 2:1 ethyl acetate-hexane gives an analytical sample mp 193°–205° C.

EXAMPLE 41

Preparation of methyl
6-(4-isopropyl-4-methyl-5-oxo-2-imidazolin-2-yl)-furo[2,3-b]pyridine-5-carboxylate

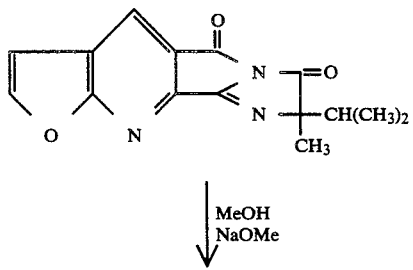

-continued

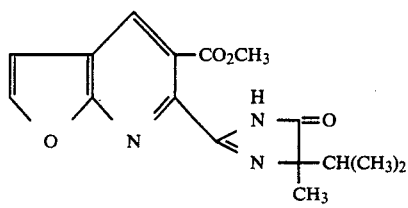

The compound prepared in Example 40 (10.5 g, 0.037 mol) is suspended in 150 mL absolute methanol and 4.0 g sodium methoxide is added. After stirring for 72 hours at room temperature the mixture is poured onto ice containing acetic acid to maintain the pH at 3–4. A white solid forms and is filtered yielding 9.8 g (84%) of the title compound with mp 134°–137° C.

EXAMPLE 42

Preparation of methyl 3-chloro-6-(4-isopropyl-4-methyl-5-oxo-2-imidazolin-2-yl)-furo[2,3-b]pyridine-5-carboxylate

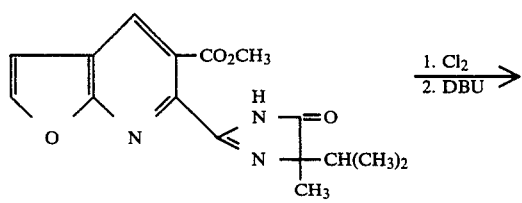

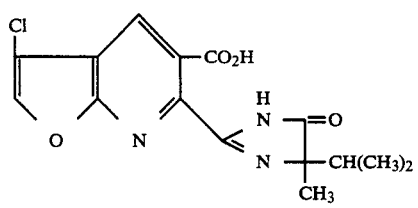

The methyl ester described in Example 40 is dissolved (1.4 g, 4.4 mmol) in 20 mL acetic acid and sodium acetate (1.0 g, 12.2 mmol) is added. Gaseous chlorine is passed into the stirred solution for two hours during which time the temperature reaches 40° C. After cooling and pouring onto 50 g ice, the mixture is extracted with ethyl acetate, washed with distilled water then with saturated sodium carbonate solution. The organic layer is then concentrated to a foam, redissolved in 20 mL methylene chloride and treated with 10 mL diazabicyclo-[5.4.0]undec-5-ene (DBU). After ten minutes, the mixture is treated with 20 mL cold dilute hydrochloric acid. The methylene chloride layer is removed, dried over anhydrous magnesium sulfate. The solution is then passed through a one-quarter inch pad of silica gel and concentrated in vacuo. Recrystallization from hexane-ethyl acetate gives 0.85 g (57%) of the 3-chloro compound mp 150°–156° C.

EXAMPLE 43

Preparation of 3-chloro-6-(4-isopropyl-4-methyl-5-oxo-2-imidazolin-2-yl)-furo[2,3-b]pyridine-5-carboxylic acid

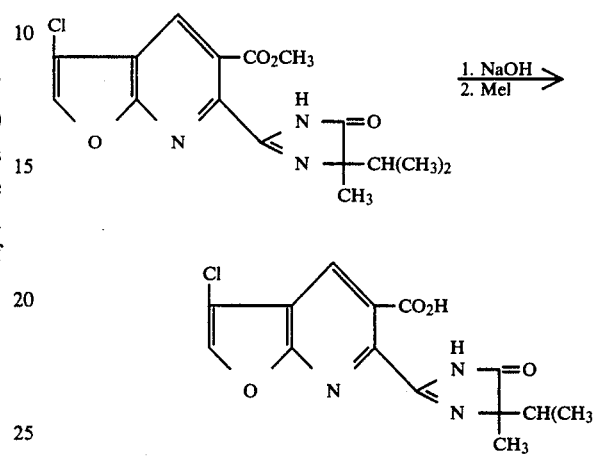

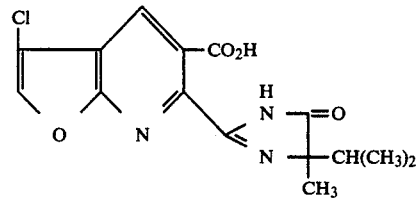

The ester from Example 42 (0.55 g, 1.157 mmol) is dissolved in 10 mL 95% ethanol and 0.28 g 50% sodium hydroxide solution is added. After one hour the mixture is treated with 10% hydrochloric acid to pH 2, and the product separates as a solid, which is filtered, dried and recrystallized from acetone to give 0.35 g (67.3%) mp 239°–240° C.

EXAMPLE 44

Preparation of (+)-6-(4-isopropyl-4-methyl-5-oxo-2-imidazolin-2-yl)-furo[2,3-b]pyridine-5-carboxylic acid

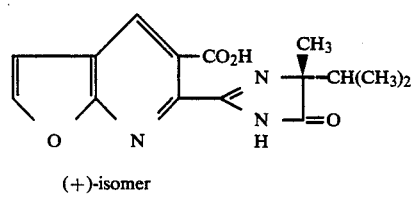

(+)-isomer

Furo[2,3-b]pyridine-5,6-Dicarboxylic anhydride (2.50 g, 0.013 mol) is suspended in 40 mLs anhydrous THF and (+)-2-amino-2,3-dimethylbutyramide (1.72 g, 0.013 mol) is added. The mixture is stirred under $N_2$ at room temperature for 16 hours. The solution is poured into 150 mLs anhydrous ether, and the resulting solid is collected in 88.6% crude yield. The unpurified adduct is converted to the indicated product in the manner described in Example 38 for the racemic mixture. The (+)-isomer is recrystallized from absolute ethanol, and is isolated in 27.0% yield from the adduct., mp 244°–245° C. $[\alpha]_D^{25}=44.5°$.

EXAMPLE 45

Preparation of sodium 6-(4-isopropyl-4-methyl-5-oxo-2-imidazolin-2-yl)furo[2,3-b]pyridine-5-carboxylate

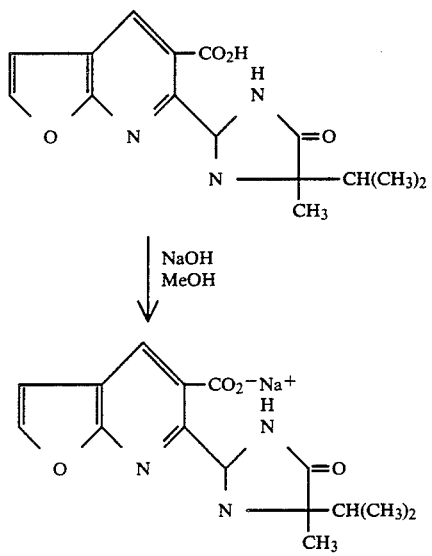

NaOH (0.13 g, 0.0033 mol) is dissolved in 50 mLs anhydrous methanol under $N_2$. The free carboxylic acid (1.00 g, 0.0033 mol) is added, dissolving to give a yellow solution. The solvent is removed in vacuo to give a yellow oil. The oil is dissolved in anhydrous ethanol and the solvent removed in vacuo to give a solid. The solid is dissolved in anhydrous ethanol and reprecipitated with anhydrous ether, giving 0.60 g (56.1%) of the title sodium salt as a yellow solid, mp 240°->250° C.

EXAMPLE 46

Preparation of 6-(4-isopropyl-4-methyl-5-oxo-2-imidazolin-2-yl)furo[2,3-b]pyridine-5-carboxylate, compound with isopropylamine (1:1)

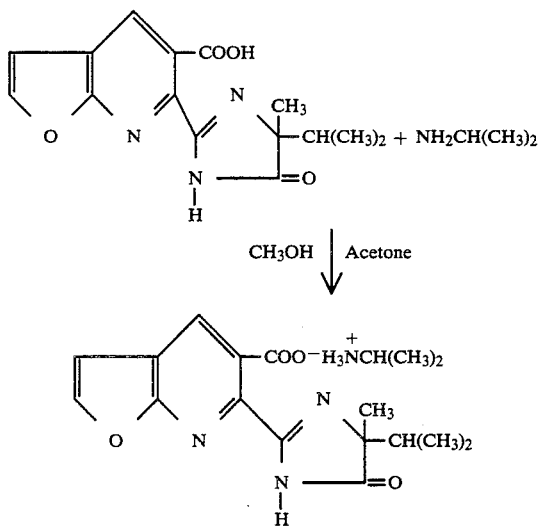

Isopropylamine (0.25 mL, 0.00266 mol) is added to a suspension of the carboxylic acid (0.80 g, 0.00266 mL) and methanol (50 mL). The reaction is stirred at room temperature for one-half hour, during which time all the solids dissolve. The solvent is removed in vacuo, and the residue is slurried in ether and filtered, yielding the isopropyl amine salt in 78.1% yield, mp 100°-220° C. with slow decomposition.

EXAMPLE 47

Preparation of imidazolin-2-yl thieno- and furo-pyridines

Utilizing the procedures of the preceeding examples and substituting the appropriate thieno or furo[3,2-b]pyridine or thieno or furo[2,3-b]pyridine compounds, yields the compounds illustrated below.

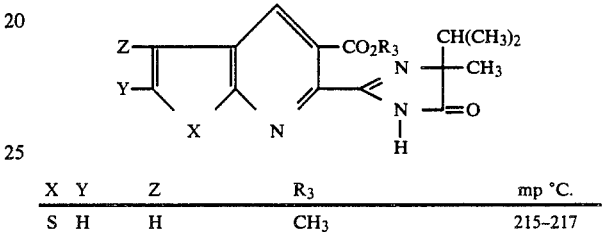

| X | Y | Z | $R_3$ | mp °C. |
|---|---|---|---|---|
| S | H | H | $CH_3$ | 215-217 |
| S | H | H | H | 220-223.5 (dec) |
| S | H | H | $-CH_2C\equiv CH$ | 188-189.5 |
| S | H | H | $-CH_2-\underset{O}{\bigcirc}$ | |
| S | H | H | $\underset{-CH_2\overset{|}{C}=CH_2}{CH_3}$ | 108-110 |
| S | $CH_3$ | H | H | 225.5-227.5 |
| S | H | Br | H | 274-276 |
| S | H | Cl | H | 266-267 |
| O | H | H | H | 237-244 |
| S | H | $NO_2$ | $CH_3$ | 201-202.5 |
| S | H | $NO_2$ | H | 260 (dec) |
| S | Cl | Cl | H | — |
| S | H | $N(CH_3)_2$ | H | — |
| S | H | $SC_6H_5$ | — | |
| S | H | $SCH_3$ | H | — |
| S | H | $OCH_3$ | H | — |
| S | H | $OCHF_2$ | H | — |
| S | $CH_3$ | $CH_3$ | H | — |
| S | H | CN | H | — |
| O | H | Cl | H | 239-240 |
| O | H | H | $CH_3$ | 134-137 |
| O | H | Br | H | 239-245 |
| O | $CH_3$ | H | H | 174-177 |
| O | $C_2H_5$ | H | H | 170-172 |
| O | $C_6H_5$ | H | H | 244-245 |
| S | Cl | H | H | 268 (dec) |
| O | H | Cl | $CH_3$ | 137-141 |
| S | H | $CH_3$ | H | 255-257 |
| S | $-(CH_2)_4-$ | | H | 234-237 |
| O | H | $CF_3$ | H | — |
| O | H | $SC_6H_5$ | H | — |
| O | H | H | $-CH_2-\underset{O}{\bigcirc}$ | 137-141 |
| O | H | H | $-CH_2C\equiv CH$ | 150-156 |
| S | Cl | H | $+NH_3-CH(CH_3)_2$ | Anal: ok for |

-continued

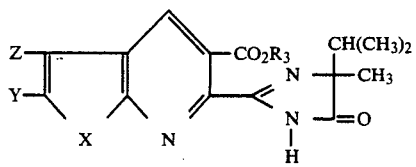

| X | Y | Z | R3 | mp °C. |
|---|---|---|---|---|
| S | H | SO2N(CH3)2 | H | S and Cl — |
| S | C6H5 | H | H | — |
| S |  | —(CH2)3— | H | — |
| S |  | —(CH)4— | H | — |
| S | H | C6H5 | H | — |
| S | H | OC6H5 | H | — |
| S | CF3 | H | H | — |
| S | C2H5 | H | H | — |
| S | H | C2H5 | H | — |
| S | H | I | H | — |
| S | H | F | H | — |
| S | H | CHO | H | — |
| S | H | CH2Cl | H | — |
| S | H | CF3 | H | — |
| O | H | NO2 | H | 220–237 (dec) |
| O | H | N(CH3)2 | H | — |
| O | H | SCH3 | H | — |
| O | H | OCH3 | H | — |
| O | Cl | H | H | — |
| O | Cl | Cl | H | — |
| O | H | CH3 | H | — |
| O | CH3 | CH3 | H | — |
| O | H | OCHF2 | H | — |
| O | H | CN | H | — |
| O | H | SO2N(CH3)2 | H | — |
| O |  | —(CH2)4— | H | — |
| O |  | —(CH2)3— | H | — |
| O |  | —(CH)4— | H | — |
| O | H | C6H5 | H | — |
| O | H | OC6H5 | H | — |
| O | CF3 | H | H | — |
| O | H | C2H5 | H | — |
| O | H | I | H | — |
| O | H | F | H | — |
| O | H | CHO | H | — |
| O | H | CH2Cl | H | — |

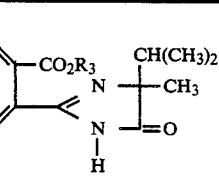

| X | Y | Z | R3 | mp °C. |
|---|---|---|---|---|
| S | H | H | H | 242–244 |
| S | H | Cl | H | 238–239 |
| S | H | Br | H | 226–227 |
| S | H | H | —CH2—(furan) | 156–157 |
| O | H | H | H | 214–223 |
| S | Cl | H | H | 266–267 |
| O | H | Cl | H | — |
| O | H | CH3 | H | — |
| O | CH3 | H | H | — |
| O | C2H5 | H | H | — |
| O | H | C2H5 | H | — |
| O | CH3 | CH3 | H | — |
| S | H | CN | H | — |

-continued

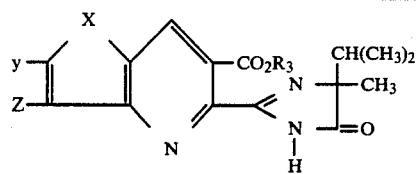

| X | Y | Z | R3 | mp °C. |
|---|---|---|---|---|
| S | H | CH3 | H | — |
| S | CH3 | H | H | — |
| S | CH3 | CH3 | H | — |
| S | H | NO2 | H | — |
| S | H | N(CH3)2 | H | — |
| S | H | SCH3 | H | — |
| S | H | OCH3 | H | — |
| S | H | OCHF2 | H | — |
| S | Cl | Cl | H | — |
| S | H | SO2N(CH3)2 | H | — |
| S | C6H5 | H | H | — |
| S | H | C6H5 | H | — |
| S |  | —(CH2)3— | H | — |
| S |  | —(CH2)4— | H | — |
| S |  | —(CH)4— | H | — |
| S | H | OC6H5 | H | — |
| S | CF3 | H | H | — |
| S | C2H5 | H | H | — |
| S | H | C2H5 | H | — |
| S | H | I | H | — |
| S | H | F | H | — |
| S | H | CHO | H | — |
| S | H | CH2Cl | H | — |
| S | H | CF3 | H | — |
| S | H | SC6H5 | H | — |

EXAMPLE 48

Preparation of 6-(4-isopropyl-4-methyl-5-thioxo-2-imidazolin-2-yl)-furo[2,3-b]pyridine-5-carboxylic acid

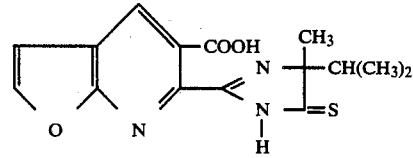

5,6-Dicarboxylic anhydride-furo[2,3-b]pyridine (1.35 g, 0.0071 mol) is suspended in 25 mLs anhydrous THF and 2-amino-2,3-dimethylthiobutyramide (1.04 g, 0.0071 mol) is added. The mixture is stirred under $N_2$ at room temperature for three hours. The suspended solid is collected and the filtrate is stripped to a solid. The combined yield is 2.30 g (96.2%). Both solids are added together to KOH (1.91 g, 0.034 mol) in 20 mLs water. The solution is warmed to 60° C. for four hours, then stirred at room temperature for 16 hours. The slightly cloudy solution is filtered to give a clear filtrate, which is acidified to pH 4 with 10% HCl. The resulting yellow solid is collected and refluxed in 100 mLs xylene for 16 hours. The indicated product crystallized from the xylene solution in 28.0% yield, mp 231°–232° C. dec.

In the same manner as described above for the furo[2,3-b]pyridine compound, 6-(B 4-isopropyl-4-methyl-5-thioxo-2-imidazolin-2-yl)-thieno[2,3-b]pyridine-5-carboxylic acid is prepared in 37% yield having a mp 242° C.

EXAMPLE 49

Preparation of 2,3-dihydro-6-(4-isopropyl-4-methyl-5-oxo-2-imidazolin-2-yl)furo[2,3-b]pyridine-5-carboxylic acid

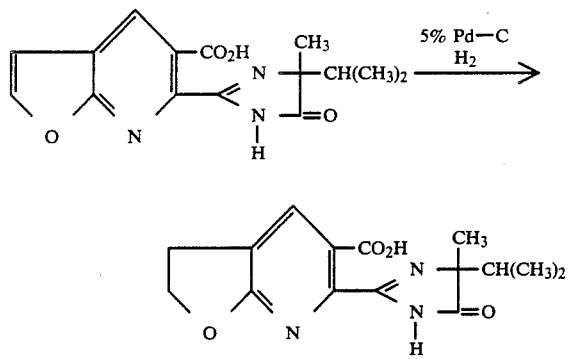

A solution of 6-(4-isopropyl-4-methyl-5-oxo-2-imidazolin-2-yl)furo[2,3-b]pyridine-5-carboxylic acid (1.7 g 0.056 mol) and 1.0 g (0.0072 mol) potassium carbonate in 200 mL 9:1 ethanol:water is added to 100 mg 5% palladium on carbon catalyst in a 500 mL pressure bottle. The bottle is fitted to a Parr hydrogenation apparatus, pressurized to 30 psi, with hydrogen, then shaken at room temperature for 10 hours. The catalyst is removed by filtration through a sintered glass funnel, and the filtrate concentrated in vacuo to 10 mL. Acidification of the residue to pH 2 gives a white precipitate which is removed by filtration, washed with water and air dried to give 1.0 g (63%) of 2,3-dihydro-6-(4-isopropyl-4-methyl-5-oxo-2-imidazolin-2-yl)furo-[2,3-b]pyridine-5-carboxylic acid as an off-white solid, mp 189°–192° C.

By the above procedure, a solution of 5-(4-isopropyl-4-methyl-5-oxo-2-imidazolin-2-yl)furo[3,2-b]pyridine (400 mg) may be converted to 2,3-dihydro-5-(4-isopropyl-4-methyl-5-oxo-2-imidazolin-2-yl)furo[3,2-b]pyridine-6-carboxylic acid, mp 205°–206° C.

EXAMPLE 50

Preparation of 4-mercaptoacetyl butyronitrile

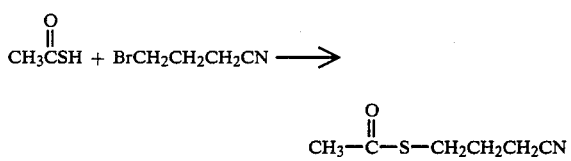

Thiolacetic acid (49 mL, 0.69 mol) is added to potassium carbonate (93.4 g, 0.68 mol) dissolved in water (150 mL). Ethanol (260 mL) is added and then 4-bromobutyronitrile is added at 15° to 28° C. and the reaction mixture stirred at room temperature for 16 hours. The resulting inorganic solids are filtered off and the filtrate extracted with toluene. The organic layer is separated, dried over anhydrous $Na_2SO_4$ and concentrated to give the desired 4-mercaptoacetyl butyronitrile as a yellow oil.

EXAMPLE 51

Preparation of dihydrothiophenimine hydrochloride

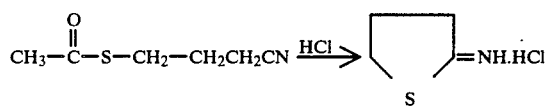

Hydrogen chloride is introduced to a cooled solution of the nitrile in methanol (220 mL) for one hour and the mixture then stirred at room temperature for 16 hours. The resulting product is filtered off, washed with ether and dried to give 55.38 g of dihydrothiophenimine hydrochloride, mp 189°–195° C.

EXAMPLE 52

Preparation of dimethyl[(tetrahydro-2-thienylidene)amino]fumarate (and maleate) acid

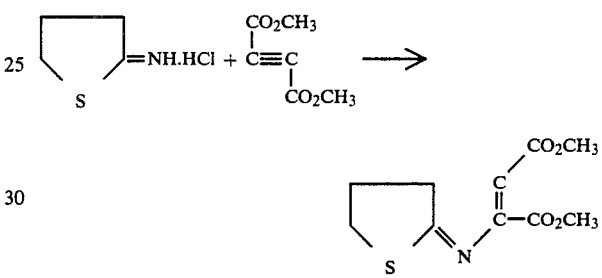

Dimethylacetylenedicarboxylate (0.45 mL, 0.037 mol) is added to a stirred solution of dihydrothiophenimine hydrochloride (0.5 g, 0.0036 mol) in methanol (60 mL) containing sodium acetate (0.3 g, 0.0036 mol) under an inert $N_2$ atmosphere at −15° C. After stirring for 16 hours at room temperature, the solvent is removed on a rotary evaporator and the resulting mixture separated by column chromatography on silica gel eluting with a methylene chloride-acetonitrile mixture (19:1) yielding 0.68 g (78% yield) of the desired mixed isomeric acid esters as a yellow oil.

EXAMPLE 53

Preparation of dimethyl 2,3-dihydrothieno[2,3-b]pyridine-5,6-dicarboxylate

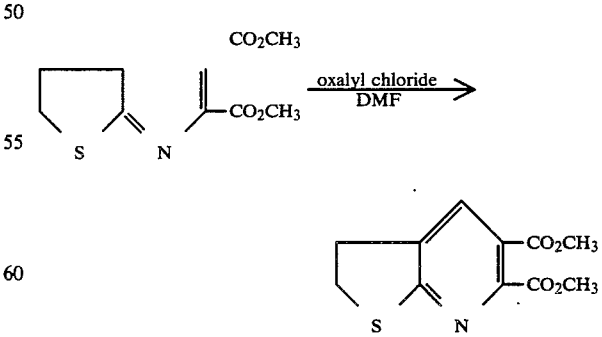

A Vilsmeier reagent is prepared by adding oxalyl chloride (0.25 mL, 0.0028 mol) to a stirred solution of DMF (0.22 mL, 0.0028 mol) in 1,2-dichloroethane (50 mL) at room temperature in an inert $N_2$ atmosphere. A 1,2-dichloroethane (50 mL) solution of dimethyl[(tetrahydro-2-thienylidine)amino]fumarate (and maleate) (0.0028 mol) is added to the Vilsmeier reagent and the reaction mixture heated at reflux for four hours. The reaction mixture is quenched with water, made basic with sodium bicarbonate and the organic layer separated and dried over anhydrous Na2SO4.

The solvent is removed in vacuo and the residue purified by column chromatography on silica gel, eluting with a methylene chloride-acetonitrile mixture (19:1). Crystallization from toluene-hexane affords dimethyl 2,3-dihydrothieno[2,3-b]pyridine-5,6-dicarboxylate as a white solid with mp 102°–103.5° C.

EXAMPLE 54

Preparation of 2,3-dihydro-6-(5-isopropyl-5-methyl-4-oxo-2-imidazolin-2-yl)thieno[2,3-b]pyridine-5-carboxylic acid, 1-oxide

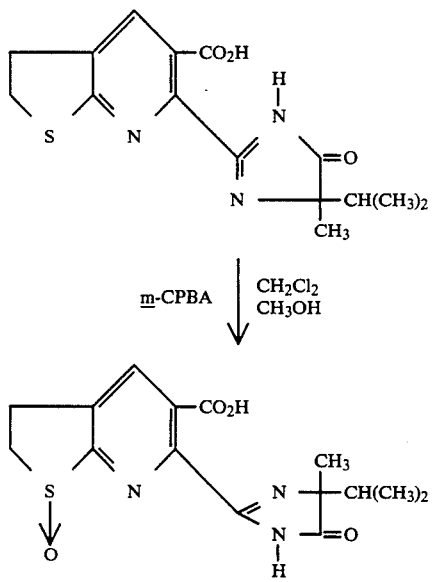

m-Chloroperbenzoic acid (2.0 g, 0.0094 mol) is added to a solution of the dihydro thieno pyridine in methylene chloride (400 mL) and methanol (40 mL) at 0° C. under a nitrogen atmosphere. After stirring for 16 hours while attaining 18° C., water 100 mL is added, followed by the addition of 100 mL of a saturated NaHCO3 solution. The aqueous layer is separated off and washed with methylene chloride. Acidification with concentrated HCl, precipitates m-chlorobenzoic acid which is removed by filtration prior to adjusting the pH of the aqueous layer to pH 1. Extraction of this acidified layer with methylene chloride and removal of the solvent yields the title product as a white solid, mp 216°–218° C. dec.

EXAMPLE 55

Preparation of diethyl dihydrothieno[3,2-b]pyridine-5,6-dicarboxylate

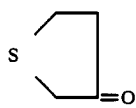

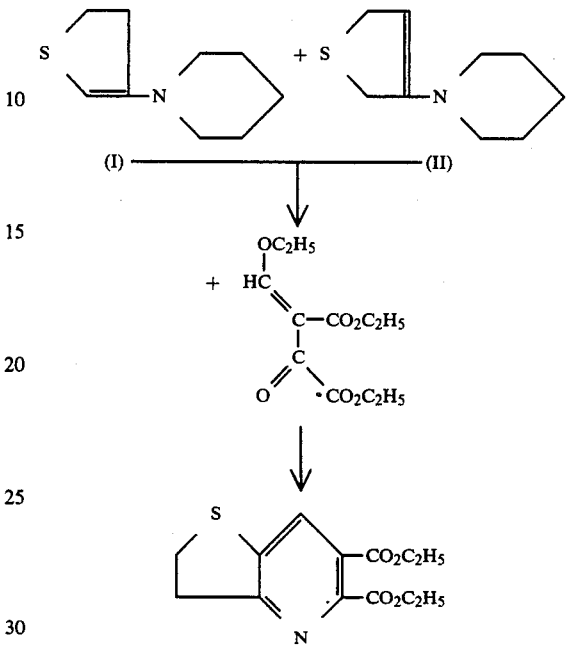

To a solution of tetrahydrothiophene-3-one (Maybridge Chem. Co; 20.0 g, 0.196 mol) in benzene (100 mL), stirred at room temperature, is added piperidine (16.7 g, 0.196 mol) and p-toluenesulfonic acid monohydrate (0.20 g, 0.001 mol). The mixture is heated at reflux under a Dean-Stark trap for four hours, cooled and stripped to a dark brown oil consisting of a 1:1 mixture of 2,3- and 2,5-dihydrothiophene enamines (I and II; Recl. Trav. Chim., 92, 865(1973).

To the above enamine mixture is added ethanol (100 mL) and diethyl ethoxymethylene oxalacetic carboxylate (72.1 g, 0.294 mol) and the mixture is stirred for 45 minutes. Ammonium acetate (45.3 g, 0.588 mol) is added in one portion and the mixture is heated at reflux for 45 minutes. After cooling, the solvents are stripped and the yellow oily diethyl dihydrothieno[3,2-b]pyridine-5,6-dicarboxylate product is obtained by chromatography after eluting with hexane-ethyl acetate. The mass spectrum shows the parent peak (m+1/e) at 282.

EXAMPLE 56

Preparation of diethyl 5,7-dihydrothieno[3,4-b]pyridine-2,3-dicarboxylate and diethyl-2,3-dihydrofuro[3,2-b]pyridine-5,6-dicarboxylate

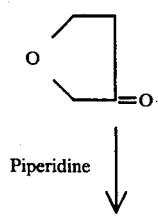

Piperidine

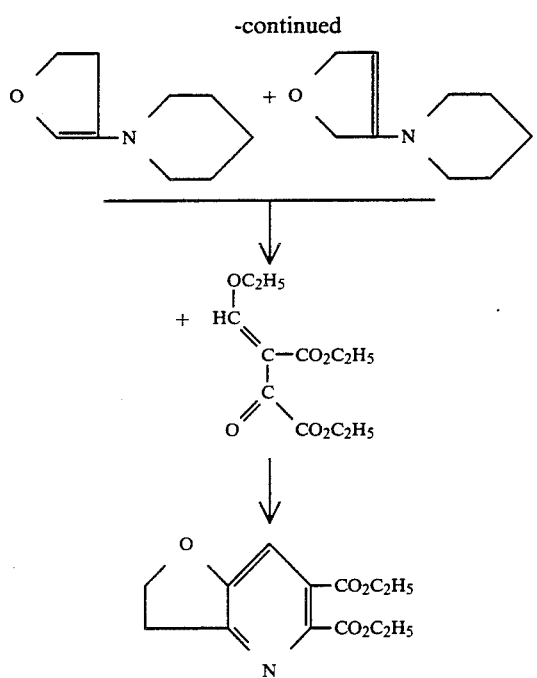

To a solution of tetrahydrofuran-3-one (J. Pharm. Sci, 59, 1678(1970); 46.55 g, 0.540 mol) in benzene (250 mL), stirred at room temperature, is added piperidine (45.98 g, 0.540 mol) and p-toluenesulfonic acid monohydrate (0.46 g, 0.002 mol). The mixture is heated at reflux under a Dean-Stark trap for four hours, cooled and stripped to a dark brown oil consisting of a 1:1 mixture of 2,3- and 2,5-dihydrothiophene enamines. Then ethanol (500 mL) and diethyl ethoxymethylene oxalacetic carboxylate (178.79 g, 1.35 mol) is added and stirring continued for 45 minutes. Ammonium acetate (124.87 g (1.62 mol) is added and the mixture is heated at reflux for 45 minutes. After cooling, the solvents are removed and the yellow oily diethyl dihydrofuro[3,2-b]pyridine-5,6-carboxylate is purified by chromatography on silica gel, eluting with hexane-ethyl acetate. The mass spectrum shows the parent peak (m+1/e) at 266.

EXAMPLE 57

Preparation of 2,3-dihydro-5 and 6-(4-isopropyl-4-methyl-5-oxo-2-imidazolin-2-yl)furo and thieno-[2,3-b] and [3,2-b]pyridines Utilizing the procedures of Examples 8, 10, 12, 15, 18, 27, 35, 36, 37, 38, 49, 53, 54, 55 an 56 yields the dihydro compounds illustrated below.

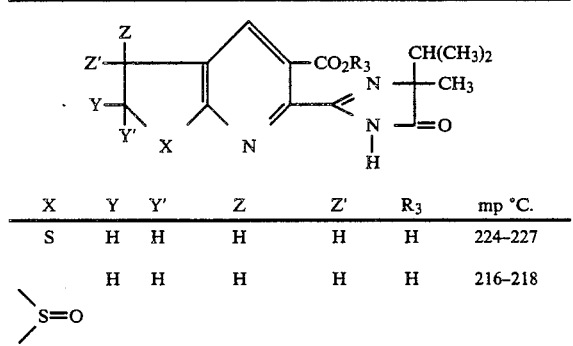

| X | Y | Y' | Z | Z' | $R_3$ | mp °C. |
|---|---|----|---|----|-------|--------|
| S | H | H  | H | H  | H     | 224-227 |
| \S=O/ | H | H | H | H | H | 216-218 |

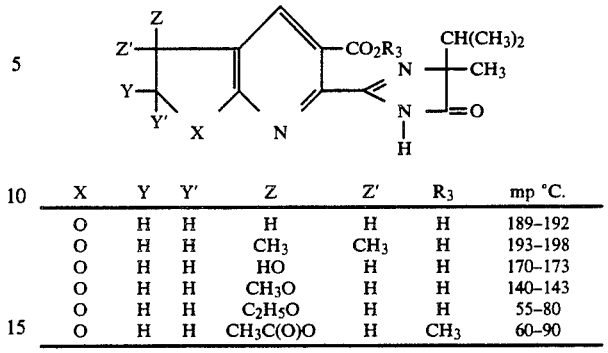

| X | Y | Y' | Z      | Z'    | $R_3$ | mp °C. |
|---|---|----|--------|-------|-------|--------|
| O | H | H  | H      | H     | H     | 189-192 |
| O | H | H  | $CH_3$ | $CH_3$| H     | 193-198 |
| O | H | H  | HO     | H     | H     | 170-173 |
| O | H | H  | $CH_3O$| H     | H     | 140-143 |
| O | H | H  | $C_2H_5O$| H   | H     | 55-80 |
| O | H | H  | $CH_3C(O)O$ | H | $CH_3$ | 60-90 |

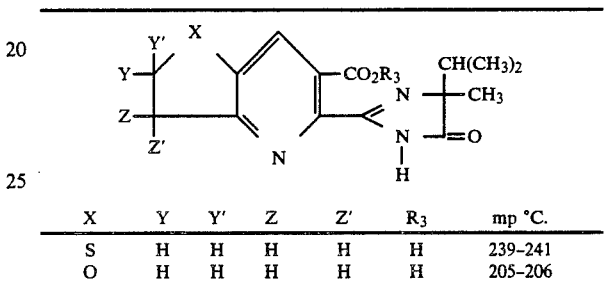

| X | Y | Y' | Z | Z' | $R_3$ | mp °C. |
|---|---|----|---|----|-------|--------|
| S | H | H  | H | H  | H     | 239-241 |
| O | H | H  | H | H  | H     | 205-206 |

EXAMPLE 58

Postemergence herbicidal evaluation of test compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ® 20, a polyoxyethylene sorbitan monolaurate surfactant of Atlas Chemical Industries, in sufficient quantities to provide the equivalent of about 0.16 kg to 10 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table I below.

| Rating System | | % Difference in Growth from the Check* |
|---|---|---|
| 0 | No Effect | 0 |
| 1 | Possible effect | 1-10 |
| 2 | Slight effect | 11-25 |
| 3 | Moderate effect | 26-40 |
| 5 | Definite injury | 41-60 |
| 6 | Herbicidal effect | 61-75 |
| 7 | Good herbicidal effect | 76-90 |
| 8 | Approaching complete kill | 91-99 |
| 9 | Complete kill | 100 |
| 4 | Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (*Echinochloa crusgalli*) |
| Green foxtail | (*Setaria viridis*) |
| Purple Nutsedge | (*Cyperus rotundus L.*) |
| Wild Oats | (*Avena fatua*) |
| Quackgrass | (*Agropyron repens*) |

-continued

| Plant Species Used | |
|---|---|
| Field Bindweed | (*Convolvulus arvensis L.*) |
| Cocklebur | (*Xanthium pensylvanicum*) |
| Morningglory | (*Ipomoea purpurea*) |
| Ragweed | (*Ambrosia artemisiifolia*) |
| Velvetleaf | (*Abutilon theophrasti*) |
| Barley | (*Hordeum vulgare*) |
| Corn | (*Zea mays*) |
| Rice | (*Oryza sativa*) |
| Soybean | (*Glycine max*) |
| Sunflower | (*Helianthus annus*) |
| Wheat | (*Triticum aestivum*) |

TABLE I

POST-EMERGENCE TESTS - RATES IN KG/HA

| COMPOUND | RATE | BARNY ARDGR | FOXTA IL SP | P NUT SEDGE | WILD OATS | QUACK GRASS | FLD B INDWD | MATRI CARIA | MRNGL RY SP | RAGWE ED | VELVE TLEAF | H BAR LY MA | CORN FIELD | COTTO N | RICE, NATO | SOYBE AN BR | S WHE AT ER |
|---|---|---|---|---|---|---|---|---|---|---|---|---|---|---|---|---|---|
| 5-(4-Isopropyl-4-methyl-5-oxo-2-imidazolin-2-yl)-furo[3,2-b]pyridine-6-carboxylic acid | .125 | 6.0 | 8.0 | 8.0 | 9.0 | 8.0 | 9.0 | 6.0 | 2.0 | 3.0 | 5.0 | | 4.0 | 8.0 | 7.0 | 0.0 | 3.0 |
| Methyl 6-(4-isopropyl-4-methyl-5-oxo-2-imidazolin-2-yl)-thieno[2,3-b]pyridine-5-carboxylate | 1.000 | 7.0 | 3.5 | 2.5 | 9.0 | 1.5 | 5.5 | 0.0 | 1.5 | 3.0 | 2.0 | | 3.5 | 3.0 | 3.5 | 0.5 | 0.5 |
| | .500 | 2.0 | 2.0 | 0.0 | 7.5 | 1.0 | 5.0 | 0.0 | 1.5 | 0.5 | 0.5 | | 1.5 | 2.0 | 3.0 | 0.0 | 0.0 |
| | .250 | 0.5 | 0.5 | 0.0 | 7.5 | 0.0 | 0.5 | 0.0 | 0.5 | 0.0 | 0.0 | | 0.0 | 0.0 | 1.5 | 0.0 | 0.0 |
| | .125 | 0.0 | 0.0 | 0.0 | 4.0 | 0.0 | 0.0 | 0.0 | 0.5 | 0.0 | 0.0 | | 0.0 | 0.0 | 1.5 | 0.0 | 0.0 |
| | .063 | 0.0 | 0.0 | 0.0 | 3.5 | 0.0 | 0.0 | 0.0 | 0.0 | 0.0 | 0.0 | | 0.0 | 0.0 | 1.0 | 0.0 | 0.0 |
| | .032 | 0.0 | 0.0 | 0.0 | 1.5 | 0.0 | 0.0 | 0.0 | 0.0 | 0.0 | 0.0 | | 0.0 | 0.0 | 1.0 | 0.0 | 0.0 |
| 6-(4-Isopropyl-4-methyl-5-oxo-2-imidazolin-2-yl)-thieno[2,3-b]pyridine-5-carboxylic acid | 1.000 | 9.0 | 9.0 | 9.0 | 9.0 | 9.0 | 9.0 | 9.0 | 6.5 | 9.0 | 9.0 | | 9.0 | 9.0 | 8.5 | 4.5 | 8.0 |
| | .500 | 9.0 | 9.0 | 7.5 | 9.0 | 9.0 | 9.0 | 9.0 | 6.5 | 9.0 | 9.0 | | 9.0 | 9.0 | 8.5 | 4.5 | 6.0 |
| | .250 | 8.5 | 8.0 | 7.0 | 9.0 | 9.0 | 8.5 | 8.0 | 4.5 | 9.0 | 8.0 | | 9.0 | 9.0 | 6.5 | 3.0 | 4.5 |
| | .125 | 7.5 | 5.5 | 7.5 | 9.0 | 8.0 | 8.5 | 5.5 | 3.5 | 7.5 | 4.0 | | 8.5 | 8.5 | 5.5 | 1.5 | 4.0 |
| | .063 | 5.0 | 3.0 | 5.5 | 4.5 | 8.0 | 8.0 | 4.5 | 1.5 | 6.0 | 2.0 | | 8.0 | 8.0 | 4.0 | 1.5 | 3.0 |
| | .032 | 4.5 | 1.5 | 3.0 | 3.5 | 4.0 | 7.0 | 3.5 | 0.5 | 4.5 | 1.0 | | 7.0 | 6.0 | 3.0 | 1.0 | 1.5 |
| 2-Isopropyl-2-methyl-5H—imidazol[1',2':1,2]-pyrrolo[3,4-b]thieno[3,2-e]pyridine-3(2H),—5-dione | 1.000 | 9.0 | 7.0 | 8.0 | 9.0 | 8.0 | 9.0 | 9.0 | 4.0 | 9.0 | 9.0 | | 9.0 | 9.0 | 9.0 | 2.0 | 2.0 |
| | .500 | 9.0 | 4.0 | 7.0 | 9.0 | 9.0 | 9.0 | 1.0 | 2.0 | 9.0 | 7.0 | | 9.0 | 9.0 | 8.0 | 3.0 | 2.0 |
| | .250 | 8.0 | 4.0 | 4.0 | 6.0 | 9.0 | 9.0 | 0.0 | 0.0 | 7.0 | 3.0 | | 9.0 | 9.0 | 6.0 | 2.0 | 2.0 |
| | .125 | 9.0 | 2.0 | 4.0 | 2.0 | 8.0 | 9.0 | 0.0 | 0.0 | 7.0 | 1.0 | | 9.0 | 8.0 | 6.0 | 1.0 | 1.0 |
| | .063 | 7.0 | 2.0 | 2.0 | 1.0 | 8.0 | 3.0 | 0.0 | 0.0 | 4.0 | 0.0 | | 9.0 | 6.0 | 4.0 | 1.0 | 1.0 |
| | .032 | 2.0 | 0.0 | 0.0 | 0.0 | 4.0 | 0.0 | 0.0 | 0.0 | 1.0 | 0.0 | | 6.0 | 3.0 | 2.0 | 0.0 | 0.0 |
| 5-(4-Isopropyl-4-methyl-5-oxo-2-imidazolin-2-yl)-thieno[3,2-b]pyridine-6-carboxylic acid | 1.000 | 9.0 | 8.0 | 8.0 | 9.0 | 9.0 | 9.0 | 6.0 | 4.0 | 9.0 | 9.0 | | 9.0 | 7.0 | 9.0 | 3.0 | 4.0 |
| | .500 | 9.0 | 7.0 | 8.0 | 9.0 | 9.0 | 9.0 | 2.0 | 4.0 | 7.0 | 6.0 | | 9.0 | 6.0 | 8.0 | 2.0 | 3.0 |
| | .250 | 9.0 | 4.0 | 7.0 | 8.0 | 9.0 | 9.0 | 0.0 | 4.0 | 7.0 | 4.0 | | 9.0 | 6.0 | 6.0 | 2.0 | 2.0 |
| | .125 | 8.0 | 2.0 | 4.0 | 8.0 | 8.0 | 3.0 | 0.0 | 2.0 | 4.0 | 1.0 | | 9.0 | 5.0 | 8.0 | 1.0 | 1.0 |
| | .063 | 6.0 | 2.0 | 4.0 | 4.0 | 8.0 | 3.0 | 0.0 | 0.0 | 4.0 | 1.0 | | 9.0 | 2.0 | 6.0 | 1.0 | 0.0 |
| | .032 | 4.0 | 0.0 | 0.0 | 2.0 | 6.0 | 0.0 | 0.0 | 0.0 | 1.0 | 0.0 | | 6.0 | 1.0 | 2.0 | 0.0 | 0.0 |
| 2-Propynyl 6-(4-isopropyl-4-methyl-5-oxo-2-imidazolin-2-yl)-thieno[2,3-b]pyridine-5-carboxylate | 1.000 | 9.0 | 7.0 | 8.0 | 8.0 | 8.0 | 9.0 | 8.0 | 4.0 | 9.0 | 8.0 | | 9.0 | 8.0 | 9.0 | 3.0 | 3.0 |
| | .500 | 9.0 | 4.0 | 6.0 | 8.0 | 8.0 | 9.0 | 6.0 | 2.0 | 8.0 | 6.0 | | 9.0 | 7.0 | 6.0 | 2.0 | 1.0 |
| | .250 | 9.0 | 2.0 | 6.0 | 3.0 | 3.0 | 9.0 | 3.0 | 1.0 | 0.0 | 4.0 | | 9.0 | 7.0 | 4.0 | 1.0 | 1.0 |
| | .125 | 6.0 | 2.0 | 2.0 | 1.0 | 1.0 | 9.0 | 1.0 | 0.0 | 0.0 | 1.0 | | 6.0 | 2.0 | 2.0 | 0.0 | 0.0 |
| | .063 | 2.0 | 1.0 | 1.0 | 2.0 | 0.0 | 6.0 | 0.0 | 0.0 | 0.0 | 0.0 | | 6.0 | 1.0 | 1.0 | 0.0 | 0.0 |
| | .032 | 1.0 | 0.0 | 0.0 | 1.0 | 0.0 | 0.0 | 0.0 | 0.0 | 0.0 | 0.0 | | 3.0 | 1.0 | 1.0 | 0.0 | 0.0 |
| Furfuryl 6-(4-isopropyl-4-methyl-5-oxo-2-imidazolin-2-yl)-thieno[2,3-b]pyridine-5-carboxylate | 1.000 | 9.0 | 9.0 | 9.0 | 9.0 | 9.0 | 9.0 | 9.0 | 4.0 | 9.0 | 6.0 | | 9.0 | 8.0 | 9.0 | 2.0 | 2.0 |
| | .500 | 8.0 | 6.0 | 8.0 | 9.0 | 9.0 | 9.0 | 3.0 | 2.0 | 9.0 | 8.0 | | 9.0 | 7.0 | 8.0 | 2.0 | 2.0 |
| | .250 | 6.0 | 4.0 | 7.0 | 8.0 | 8.0 | 8.0 | 1.0 | 1.0 | 9.0 | 6.0 | | 9.0 | 7.0 | 6.0 | 1.0 | 1.0 |
| | .125 | 2.0 | 2.0 | 4.0 | 7.0 | 2.0 | 7.0 | 0.0 | 0.0 | 2.0 | 3.0 | | 8.0 | 6.0 | 4.0 | | 1.0 |
| | .063 | 2.0 | 1.0 | 0.0 | 2.0 | 1.0 | 4.0 | 0.0 | 0.0 | 0.0 | 0.0 | | 2.0 | 2.0 | 2.0 | | |
| | .032 | 0.0 | 0.0 | 0.0 | 1.0 | 0.0 | 0.0 | 0.0 | 0.0 | 0.0 | 0.0 | | 1.0 | 1.0 | 1.0 | 0.0 | 0.0 |
| 2-Methylallyl 6-(4-isopropyl-4-methyl-5-oxo-2-imidazolin-2-yl)-thieno[2,3-b]pyridine-5-carboxylate | 1.000 | 9.0 | 7.0 | 8.0 | 8.0 | 8.0 | 8.0 | 6.0 | 0.0 | 9.0 | 8.0 | | 9.0 | 8.0 | 9.0 | 2.0 | 2.0 |
| | .500 | 7.0 | 6.0 | 6.0 | 6.0 | 6.0 | 7.0 | 3.0 | 0.0 | 9.0 | 8.0 | | 8.0 | 7.0 | 5.0 | 2.0 | 2.0 |
| | .250 | 7.0 | 4.0 | 2.0 | 5.0 | 4.0 | 8.0 | 2.0 | 0.0 | 7.0 | 3.0 | | 6.0 | 7.0 | 4.0 | 1.0 | 1.0 |
| | .125 | 4.0 | 2.0 | 0.0 | 3.0 | 2.0 | 4.0 | 0.0 | 0.0 | 2.0 | 2.0 | | 4.0 | 7.0 | 4.0 | 0.0 | 0.0 |
| | .063 | 2.0 | 0.0 | 0.0 | 2.0 | 1.0 | 2.0 | 0.0 | 0.0 | 0.0 | 1.0 | | 3.0 | 6.0 | 3.0 | 0.0 | 0.0 |
| | .032 | 0.0 | 0.0 | 0.0 | 1.0 | 0.0 | 0.0 | 0.0 | 0.0 | 0.0 | 0.0 | | 2.0 | 4.0 | 2.0 | 0.0 | 0.0 |
| 3-Chloro-5-(4-isopropyl-4-methyl-5-oxo-2-imidazolin-2-yl)-thieno[3,2-b]- | 1.000 | 3.0 | 6.0 | 0.0 | 7.0 | 6.0 | 6.0 | 0.0 | 6.0 | 6.0 | 0.0 | 6.0 | 7.0 | 4.0 | 3.0 | 2.0 | 2.0 |
| | .500 | 2.0 | 2.0 | 0.0 | 6.0 | 2.0 | 2.0 | 0.0 | 2.0 | 0.0 | 0.0 | | 7.0 | 4.0 | 2.0 | 0.0 | 0.0 |
| | .250 | 1.0 | 0.0 | 0.0 | 2.0 | 0.0 | 2.0 | 1.0 | 3.0 | 0.0 | 0.0 | | 2.0 | 2.0 | 0.0 | 0.0 | 0.0 |
| | .125 | 0.0 | 0.0 | 0.0 | 0.0 | 0.0 | 0.0 | 0.0 | 0.0 | 2.0 | 0.0 | | 3.0 | 1.0 | 1.0 | 0.0 | 0.0 |

TABLE I-continued

POST-EMERGENCE TESTS - RATES IN KG/HA

| COMPOUND | RATE | BARNY ARDGR | FOXTAIL SP | P NUT SEDGE | WILD OATS | QUACK GRASS | FLD B INDWD | MATRI CARIA | MRNGL RY SP | RAGWE ED | VELVE TLEAF | H BAR LY MA | CORN FIELD | COTTON | RICE, NATO | SOYBE AN BR | S WHE AT ER |
|---|---|---|---|---|---|---|---|---|---|---|---|---|---|---|---|---|---|
| pyridine-6-carbo- xylic acid | .063 | 0.0 | 0.0 | 0.0 | 0.0 | 0.0 | 0.0 | 0.0 | 0.0 | 0.0 | 0.0 | | 2.0 | 0.0 | 1.0 | 0.0 | 0.0 |
| | .032 | 0.0 | 0.0 | 0.0 | 0.0 | 0.0 | 0.0 | 0.0 | 0.0 | 0.0 | 0.0 | | 1.0 | 0.0 | 1.0 | 0.0 | 0.0 |
| 3-Bromo-5-(4-iso- propyl-4-methyl-5- oxo-2-imidazolin-2- yl)-thieno[3,2-b]- pyridine-6-carbo- xylic acid | 1.000 | 0.0 | 2.0 | 2.0 | 0.0 | 2.0 | 2.0 | 2.0 | 6.0 | 2.0 | 0.0 | | 6.0 | 2.0 | | 0.0 | 2.0 |
| | .500 | 0.0 | 1.0 | 0.0 | 0.0 | 0.0 | 1.0 | 1.0 | 6.0 | 8.0 | 0.0 | | 6.0 | 1.0 | | 0.0 | 2.0 |
| | .250 | 0.0 | 0.0 | 0.0 | 0.0 | 0.0 | 0.0 | 0.0 | 0.0 | 0.0 | 0.0 | | 4.0 | 0.0 | | 0.0 | 2.0 |
| | .125 | 0.0 | 0.0 | 0.0 | 0.0 | 0.0 | 0.0 | 0.0 | 0.0 | 0.0 | 0.0 | | 2.0 | 0.0 | | 0.0 | 2.0 |
| | .063 | 0.0 | 0.0 | 0.0 | 0.0 | 0.0 | 0.0 | 0.0 | 0.0 | 0.0 | 0.0 | | 2.0 | 0.0 | | 0.0 | 1.0 |
| | .032 | 0.0 | 0.0 | 0.0 | 0.0 | 0.0 | 0.0 | 0.0 | 0.0 | 0.0 | 0.0 | | 2.0 | 0.0 | | 0.0 | 0.0 |
| 3-Bromo-6-(4-iso- propyl-4-methyl-5- oxo-2-imidazolin-2- yl)-thieno[2,3-b]- pyridine-5-carbo- xylic acid | 1.000 | 9.0 | 7.0 | 2.0 | 9.0 | 7.0 | 9.0 | 9.0 | 6.0 | 8.0 | 3.0 | | 9.0 | 9.0 | 6.0 | 2.0 | 6.0 |
| | .500 | 8.0 | 7.0 | 1.0 | 8.0 | 7.0 | 4.0 | 8.0 | 2.0 | 8.0 | 1.0 | | 9.0 | 9.0 | 6.0 | 0.0 | 5.0 |
| | .250 | 4.0 | 5.0 | 0.0 | 7.0 | 4.0 | 4.0 | 9.0 | 0.0 | 8.0 | 0.0 | | 9.0 | 9.0 | 3.0 | 0.0 | 5.0 |
| | .125 | 2.0 | 3.0 | 0.0 | 7.0 | 4.0 | 4.0 | 9.0 | 0.0 | 8.0 | 0.0 | | 8.0 | 9.0 | 2.0 | 0.0 | 2.0 |
| | .063 | 0.0 | 0.0 | 0.0 | 3.0 | 0.0 | 0.0 | 9.0 | 0.0 | 6.0 | 0.0 | | 7.0 | 9.0 | 2.0 | 0.0 | 2.0 |
| | .032 | 0.0 | 0.0 | 0.0 | 0.0 | 0.0 | 0.0 | 9.0 | 0.0 | 4.0 | 0.0 | | 3.0 | 9.0 | 2.0 | 0.0 | 2.0 |
| 6-(4-Isopropyl-4- methyl-5-oxo-2-imida- zolin-2-yl)-2-methyl- thieno[2,3-b]pyridine 5-carboxylic acid | 1.000 | 9.0 | 9.0 | 5.0 | 9.0 | 9.0 | 9.0 | 9.0 | 9.0 | 8.0 | 9.0 | | 9.0 | 9.0 | 7.0 | 5.0 | 8.0 |
| | .500 | 9.0 | 9.0 | 5.0 | 8.0 | 9.0 | 8.0 | 8.0 | 9.0 | 6.0 | 8.0 | | 9.0 | 9.0 | 8.0 | 5.0 | 8.0 |
| | .250 | 9.0 | 9.0 | 5.0 | 8.0 | 5.0 | 8.0 | 8.0 | 8.0 | 3.0 | 8.0 | | 9.0 | 9.0 | 8.0 | 4.0 | 7.0 |
| | .125 | 8.0 | 8.0 | 2.0 | 5.0 | 7.0 | 2.0 | 8.0 | 8.0 | 0.0 | 6.0 | | 9.0 | 9.0 | 7.0 | 2.0 | 7.0 |
| | .063 | 3.0 | 3.0 | 1.0 | 5.0 | 3.0 | 4.0 | 4.0 | 7.0 | 0.0 | 2.0 | | 9.0 | 9.0 | 6.0 | 2.0 | 3.0 |
| | .032 | 0.0 | 0.0 | 0.0 | 2.0 | 2.0 | 4.0 | 0.0 | 4.0 | 8.0 | 0.0 | | 3.0 | 9.0 | 6.0 | 2.0 | 2.0 |
| Furfuryl 5-(4-iso- propyl-4-methyl-5- oxo-2-imidazolin- 2-yl)-thieno[3,2-b]- pyridine-6-carbo- xylate | 1.000 | 9.0 | 9.0 | 8.0 | 8.0 | 8.0 | 9.0 | 8.0 | 8.0 | 8.0 | 7.0 | | 9.0 | 9.0 | 6.0 | 3.0 | 2.0 |
| | .500 | 9.0 | 7.0 | 8.0 | 8.0 | 8.0 | 8.0 | 5.0 | 8.0 | 6.0 | 5.0 | | 9.0 | 9.0 | 6.0 | 2.0 | 1.0 |
| | .250 | 9.0 | 7.0 | 7.0 | 8.0 | 7.0 | 7.0 | 2.0 | 7.0 | 8.0 | 5.0 | | 9.0 | 8.0 | 5.0 | 3.0 | 1.0 |
| | .125 | 9.0 | 4.0 | 6.0 | 6.0 | 8.0 | 7.0 | 0.0 | 7.0 | 7.0 | 2.0 | | 9.0 | 9.0 | 5.0 | 2.0 | 0.0 |
| | .063 | 7.0 | 0.0 | 2.0 | 4.0 | 4.0 | 4.0 | 0.0 | 4.0 | 2.0 | 0.0 | | 7.0 | 2.0 | 4.0 | 2.0 | 0.0 |
| | .032 | 0.0 | 0.0 | 0.0 | 0.0 | 2.0 | 0.0 | 0.0 | 2.0 | 0.0 | 0.0 | | 2.0 | 9.0 | 3.0 | 1.0 | 0.0 |
| 3-Chloro-6-(4-iso- propyl-4-methyl-5- oxo-2-imidazolin- 2-yl)-thieno[2,3-b]- pyridine-5-carbo- xylic acid | 1.000 | 9.0 | 9.0 | 8.0 | 9.0 | 9.0 | 8.0 | 9.0 | 9.0 | 8.0 | 4.0 | | 9.0 | 9.0 | 6.0 | 2.0 | 9.0 |
| | .500 | 9.0 | 8.0 | 6.0 | 8.0 | 9.0 | 8.0 | 9.0 | 9.0 | 9.0 | 3.0 | | 9.0 | 9.0 | 6.0 | 1.0 | 8.0 |
| | .250 | 8.0 | 7.0 | 2.0 | 9.0 | 8.0 | 8.0 | 8.0 | 8.0 | 9.0 | 0.0 | | 9.0 | 9.0 | 6.0 | 0.0 | 6.0 |
| | .125 | 6.0 | 6.0 | 0.0 | 9.0 | 6.0 | 6.0 | 2.0 | 8.0 | 8.0 | 0.0 | | 9.0 | 9.0 | 5.0 | 2.0 | 6.0 |
| | .063 | 4.0 | 4.0 | 0.0 | 4.0 | 3.0 | 0.0 | 0.0 | 2.0 | 0.0 | 0.0 | | 8.0 | 2.0 | 4.0 | 1.0 | 4.0 |
| | .032 | 0.0 | 0.0 | 0.0 | 4.0 | 2.0 | 0.0 | 0.0 | 0.0 | 0.0 | 0.0 | | 2.0 | 9.0 | 9.0 | 0.0 | 2.0 |
| 6-(4-Isopropyl-4- methyl-5-oxo-2-imida- zolin-2-yl)furo- [2,3-b]pyridine-5- carboxylic acid | 1.000 | 9.0 | 9.0 | 9.0 | 9.0 | 9.0 | 9.0 | 9.0 | 9.0 | 9.0 | 9.0 | | 9.0 | 9.0 | 9.0 | 6.0 | 9.0 |
| | .500 | 9.0 | 9.0 | 9.0 | 9.0 | 9.0 | 8.0 | 9.0 | 9.0 | 9.0 | 9.0 | | 9.0 | 9.0 | 8.0 | 6.0 | 9.0 |
| | .250 | 9.0 | 9.0 | 9.0 | 9.0 | 9.0 | 6.0 | 9.0 | 9.0 | 9.0 | 9.0 | | 9.0 | 9.0 | 8.0 | 6.0 | 8.0 |
| | .125 | 9.0 | 9.0 | 8.0 | 9.0 | 8.0 | 6.0 | 9.0 | 9.0 | 9.0 | 8.0 | | 9.0 | 9.0 | 8.0 | 3.0 | 8.0 |
| | .063 | 9.0 | 9.0 | 9.0 | 9.0 | 8.0 | 7.0 | 4.0 | 9.0 | 9.0 | 7.0 | | 9.0 | 9.0 | 7.0 | 2.0 | 7.0 |
| | .032 | 9.0 | 9.0 | 9.0 | 9.0 | 8.0 | 7.0 | 4.0 | 8.0 | 9.0 | 0.0 | | 9.0 | 9.0 | 7.0 | 2.0 | 7.0 |
| 2,3-Dihydro-6-(4- isopropyl-4-methyl- 5-oxo-2-imidazolin- 2-yl)-furo[2,3-b]- pyridine-5-carbo- xylic acid | 1.000 | 9.0 | 9.0 | 9.0 | 9.0 | 9.0 | 9.0 | 9.0 | 9.0 | 9.0 | 9.0 | | 9.0 | 9.0 | 9.0 | 7.0 | 9.0 |
| | .500 | 9.0 | 9.0 | 9.0 | 9.0 | 9.0 | 8.0 | 9.0 | 9.0 | 9.0 | 9.0 | | 9.0 | 9.0 | 8.0 | 6.0 | 9.0 |
| | .250 | 9.0 | 9.0 | 9.0 | 9.0 | 9.0 | 8.0 | 6.0 | 9.0 | 9.0 | 9.0 | | 9.0 | 9.0 | 8.0 | 3.0 | 9.0 |
| | .125 | 9.0 | 9.0 | 8.0 | 8.0 | 8.0 | 8.0 | 2.0 | 7.0 | 8.0 | 6.0 | | 9.0 | 0.0 | 0.0 | 1.0 | 1.0 |
| | .063 | 9.0 | 8.0 | 8.0 | 8.0 | 8.0 | 8.0 | 0.0 | 7.0 | 8.0 | 6.0 | | 6.0 | 9.0 | 8.0 | 1.0 | 1.0 |
| | .032 | 9.0 | 6.0 | 8.0 | 8.0 | 7.0 | 8.0 | 0.0 | 4.0 | 7.0 | 2.0 | | 8.0 | 9.0 | 7.0 | 1.0 | 2.0 |

EXAMPLE 59

Preemergence Herbicidal Evaluation of Test Compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table II below. When more than one test is involved for a given compound, the data are averaged.

TABLE II

PRE-EMERGENCE TESTS - RATES IN KG/HA

| Compound | RATE | BARNY ARDGR | FOXTA IL SP | P NUT SEDGE | WILD OATS | QUACK GRASS | FLD B INDWD | MATRI CARIA | MRNGL RY SP | RAGWE ED | VELVE TLEAF | H BAR LY MA | CORN FIELD | COTTO N | RICE, NATO | SOYBE AN BR | S WHE AT ER |
|---|---|---|---|---|---|---|---|---|---|---|---|---|---|---|---|---|---|
| Methyl 6-(4-isopropyl-4-methyl-5-oxo-2-imidazolin-2-yl)-thieno[2,3-b]pyridine-5-carboxylate | .500 | 8.5 | 8.5 | 7.5 | 8.5 | 8.0 | 9.0 | 6.5 | 9.0 | 9.0 | 7.5 | 5.0 | 5.0 | 7.5 | 6.5 | 1.5 | 1.5 |
|  | .250 | 7.0 | 5.5 | 7.0 | 8.0 | 3.0 | 9.0 | 4.5 | 6.0 | 6.5 | 6.0 | 2.0 | 3.5 | 7.0 | 5.5 | 1.0 | 0.5 |
|  | .125 | 5.0 | 3.0 | 4.0 | 7.0 | 1.5 | 7.0 | 2.5 | 5.5 | 5.5 | 4.5 | 0.0 | 3.0 | 5.5 | 4.5 | 0.5 | 0.5 |
|  | .063 | 1.5 | 1.0 | 2.5 | 5.0 | 0.5 | 2.0 | 0.5 | 5.0 | 1.0 | 2.0 | 0.0 | 1.5 | 2.5 | 2.0 | 0.0 | 0.0 |
|  | .032 | 0.5 | 0.5 | 1.0 | 2.0 | 0.0 | 1.0 | 0.0 | 2.0 | 0.0 | 2.0 | 0.0 | 1.5 | 1.5 | 0.5 | 0.0 | 0.0 |
|  | .016 | 0.0 | 0.0 | 0.5 | 1.0 | 0.0 | 0.0 | 0.0 | 1.0 | 1.0 | 1.0 | 0.0 | 1.0 | 1.5 | 0.5 | 0.0 | 0.0 |
| 6-(4-Isopropyl-4-methyl-5-oxo-2-imidazolin-2-yl)-thieno[2,3-b]pyridine-5-carboxylic acid | .500 | 9.0 | 9.0 | 9.0 | 9.0 | 9.0 | 9.0 | 8.5 | 5.5 | 8.5 | 9.0 | 9.0 | 9.0 | 9.0 | 9.0 | 5.0 | 5.5 |
|  | .250 | 6.5 | 8.5 | 9.0 | 9.0 | 9.0 | 9.0 | 8.0 | 4.5 | 8.0 | 7.0 | 8.0 | 8.0 | 9.0 | 8.0 | 3.0 | 5.0 |
|  | .125 | 5.5 | 8.0 | 9.0 | 7.5 | 9.0 | 9.0 | 8.0 | 4.5 | 8.5 | 7.0 | 8.0 | 9.0 | 9.0 | 8.0 | 2.5 | 4.0 |
|  | .063 | 3.0 | 4.0 | 8.5 | 7.5 | 8.0 | 9.0 | 7.0 | 3.5 | 6.0 | 4.5 | 8.0 | 9.0 | 7.5 | 6.0 | 0.5 | 2.0 |
|  | .032 | 1.5 | 2.5 | 8.0 | 5.0 | 7.5 | 7.0 | 5.5 | 4.0 | 2.0 | 2.5 | 5.0 | 6.0 | 5.0 | 5.5 | 0.5 | 1.5 |
|  | .016 | 0.0 | 0.0 | 6.0 | 2.0 | 6.5 | 5.0 | 3.5 | 1.0 | 0.0 | 1.0 | 3.0 | 3.0 | 3.0 | 2.5 | 0.0 | 0.5 |
| 2-Isopropyl-2-methyl-5H—imidazol[1',2':1,2]pyrrolo[3,4-b]thieno[3,2-e]pyridine-3(2H), 5-dione | .500 | 9.0 | 9.0 | 9.0 | 9.0 | 9.0 | 9.0 | 9.0 | 6.0 | 9.0 | 8.0 | 9.0 | 9.0 | 9.0 | 9.0 | 4.0 | 7.0 |
|  | .250 | 9.0 | 8.0 | 9.0 | 9.0 | 9.0 | 9.0 | 0.0 | 4.0 | 9.0 | 7.0 | 8.0 | 9.0 | 8.0 | 7.0 | 3.0 | 2.0 |
|  | .125 | 9.0 | 7.0 | 9.0 | 8.0 | 9.0 | 9.0 | 8.0 | 4.0 | 7.0 | 5.0 | 8.0 | 9.0 | 8.0 | 6.0 | 1.0 | 2.0 |
|  | .063 | 3.0 | 2.0 | 8.0 | 7.0 | 9.0 | 9.0 | 6.0 | 3.0 | 7.0 | 3.0 | 7.0 | 6.0 | 6.0 | 4.0 | 1.0 | 2.0 |
|  | .032 | 0.0 | 0.0 | 8.0 | 3.0 | 4.0 | 9.0 | 3.0 | 1.0 | 0.0 | 2.0 | 5.0 | 4.0 | 4.0 | 2.0 | 1.0 | 1.0 |
|  | .016 | 0.0 | 0.0 | 6.0 | 1.0 | 0.0 | 7.0 | 1.0 | 0.0 | 0.0 | 0.0 | 3.0 | 2.0 | 2.0 | 1.0 | 1.0 | 0.0 |
| 5-(4-isopropyl-4-methyl-5-oxo-2-imidazolin-2-yl)-thieno[3,2-b]pyridine-6-carboxylic acid | .500 | 9.0 | 9.0 | 9.0 | 9.0 | 8.0 | 9.0 | 9.0 | 7.0 | 9.0 | 8.0 | 9.0 | 9.0 | 9.0 | 9.0 | 4.0 | 9.0 |
|  | .250 | 9.0 | 9.0 | 9.0 | 9.0 | 8.0 | 9.0 | 0.0 | 6.0 | 6.0 | 7.0 | 9.0 | 9.0 | 9.0 | 9.0 | 2.0 | 3.0 |
|  | .125 | 9.0 | 7.0 | 9.0 | 8.0 | 7.0 | 9.0 | 8.0 | 5.0 | 0.0 | 5.0 | 8.0 | 9.0 | 9.0 | 9.0 | 1.0 | 3.0 |
|  | .063 | 2.0 | 4.0 | 8.0 | 3.0 | 3.0 | 9.0 | 6.0 | 3.0 | 7.0 | 3.0 | 6.0 | 9.0 | 8.0 | 8.0 | 0.0 | 3.0 |
|  | .032 | 0.0 | 2.0 | 6.0 | 2.0 | 1.0 | 9.0 | 5.0 | 1.0 | 4.0 | 3.0 | 2.0 | 5.0 | 7.0 | 5.0 | 0.0 | 1.0 |
|  | .016 | 0.0 | 0.0 | 4.0 | 0.0 | 0.0 | 7.0 | 4.0 | 0.0 | 0.0 | 0.0 | 0.0 | 3.0 | 5.0 | 3.0 | 0.0 | 0.0 |
| 2-Propynyl 6-(4-isopropyl-4-methyl-5-oxo-2-imidazolin-2-yl)-thieno[2,3-b]pyridine-5-carboxylate | .500 | 9.0 | 9.0 | 9.0 | 9.0 | 9.0 | 9.0 | 9.0 | 6.0 | 9.0 | 9.0 | 8.0 | 9.0 | 9.0 | 9.0 | 1.0 | 5.0 |
|  | .250 | 9.0 | 9.0 | 9.0 | 8.0 | 9.0 | 9.0 | 9.0 | 2.0 | 9.0 | 7.0 | 8.0 | 3.0 | 9.0 | 7.0 | 0.0 | 3.0 |
|  | .125 | 9.0 | 6.0 | 9.0 | 6.0 | 9.0 | 9.0 | 8.0 | 1.0 | 8.0 | 7.0 | 4.0 | 3.0 | 7.0 | 7.0 | 0.0 | 2.0 |
|  | .063 | 7.0 | 5.0 | 6.0 | 6.0 | 8.0 | 9.0 | 8.0 | 0.0 | 7.0 | 3.0 | 3.0 | 3.0 | 6.0 | 5.0 | 0.0 | 2.0 |
|  | .032 | 0.0 | 0.0 | 7.0 | 3.0 | 7.0 | 9.0 | 7.0 | 0.0 | 5.0 | 1.0 | 3.0 | 3.0 | 5.0 | 4.0 | 0.0 | 2.0 |
|  | .016 | 0.0 | 0.0 | 6.0 | 2.0 | 5.0 | 7.0 | 6.0 | 0.0 | 0.0 | 0.0 | 0.0 | 2.0 | 3.0 | 2.0 | 0.0 | 2.0 |
| Furfuryl 6-(4-isopropyl-4-methyl-5-oxo-2-imidazolin-2-yl)-thieno[2,3-b]pyridine-5-carboxylate | .500 | 9.0 | 9.0 | 9.0 | 9.0 | 9.0 | 9.0 | 9.0 | 3.0 | 9.0 | 9.0 | 8.0 | 9.0 | 9.0 | 9.0 | 3.0 | 4.0 |
|  | .250 | 9.0 | 8.0 | 9.0 | 8.0 | 8.0 | 9.0 | 8.0 | 1.0 | 9.0 | 6.0 | 8.0 | 9.0 | 9.0 | 9.0 | 1.0 | 2.0 |
|  | .125 | 8.0 | 8.0 | 9.0 | 0.0 | 7.0 | 8.0 | 8.0 | 0.0 | 7.0 | 6.0 | 2.0 | 9.0 | 8.0 | 7.0 | 1.0 | 2.0 |
|  | .063 | 2.0 | 3.0 | 6.0 | 3.0 | 5.0 | 9.0 | 6.0 | 0.0 | 5.0 | 3.0 | 0.0 | 2.0 | 8.0 | 5.0 | 0.0 | 1.0 |
|  | .032 | 0.0 | 0.0 | 0.0 | 2.0 | 3.0 | 8.0 | 5.0 | 0.0 | 0.0 | 0.0 | 0.0 | 2.0 | 6.0 | 3.0 | 0.0 | 1.0 |
|  | .016 | 0.0 | 0.0 | 2.0 | 1.0 | 0.0 | 3.0 | 4.0 | 0.0 | 0.0 | 0.0 | 0.0 | 2.0 | 5.0 | 1.0 | 0.0 | 0.0 |
| 2-Methylallyl 6-(4-isopropyl-4-methyl-5-oxo-2-imidazolin-2-yl)-thieno[2,3-b]pyridine-5-carboxylate | .500 | 9.0 | 9.0 | 6.0 | 8.0 | 9.0 | 9.0 | 9.0 | 0.0 | 9.0 | 8.0 | 5.0 | 4.0 | 7.0 | 7.0 | 0.0 | 1.0 |
|  | .250 | 2.0 | 3.0 | 6.0 | 0.0 | 6.0 | 3.0 | 4.0 | 3.0 | 3.0 | 6.0 | 0.0 | 2.0 | 7.0 | 3.0 | 0.0 | 0.0 |
|  | .125 | 0.0 | 0.0 | 3.0 | 0.0 | 4.0 | 9.0 | 0.0 | 1.0 | 0.0 | 0.0 | 0.0 | 2.0 | 0.0 | 0.0 | 0.0 | 0.0 |
|  | .063 | 0.0 | 0.0 | 1.0 | 0.0 | 3.0 | 7.0 | 0.0 | 0.0 | 0.0 | 0.0 | 0.0 | 1.0 | 0.0 | 0.0 | 0.0 | 0.0 |
|  | .032 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | .016 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 3-Chloro-5-(4-isopropyl-4-methyl-5-oxo-2-imidazolin-2-yl)-thieno[3,2-b]pyridine-6-carboxylic acid | .500 | 2.0 | 4.0 | 7.0 | 8.0 | 7.0 | 9.0 | 7.0 | 8.0 | 8.0 | 8.0 | 5.0 | 8.0 | 8.0 | 9.0 | 3.0 | 3.0 |
|  | .250 | 2.0 | 4.0 | 2.0 | 6.0 | 7.0 | 9.0 | 3.0 | 8.0 | 8.0 | 7.0 | 0.0 | 7.0 | 8.0 | 9.0 | 3.0 | 3.0 |
|  | .125 | 1.0 | 0.0 | 2.0 | 2.0 | 6.0 | 2.0 | 0.0 | 7.0 | 6.0 | 2.0 | 0.0 | 7.0 | 6.0 | 2.0 | 1.0 | 1.0 |
|  | .063 | 0.0 | 0.0 | 0.0 | 2.0 | 2.0 | 1.0 | 0.0 | 0.0 | 2.0 | 0.0 | 0.0 | 4.0 | 4.0 | 1.0 | 0.0 | 0.0 |
|  | .032 | 0.0 | 0.0 | 2.0 | 1.0 | 0.0 | 0.0 | 0.0 | 0.0 | 0.0 | 0.0 |  | 2.0 | 0.0 | 0.0 | 0.0 | 0.0 |
|  | .016 | 0.0 | 0.0 | 0.0 | 0.0 | 0.0 | 0.0 | 0.0 | 0.0 |  | 0.0 |  | 9.0 | 0.0 | 0.0 | 0.0 | 0.0 |
| 3-Bromo-5-(4-isopropyl-4-methyl-5-oxo- | .500 | 6.0 | 6.0 | 5.0 | 6.0 | 0.0 | 0.0 | 2.0 | 8.0 | 8.0 | 4.0 |  | 9.0 | 4.0 | 4.0 | 2.0 | 0.0 |
|  | .250 | 5.0 | 5.0 | 4.0 | 2.0 | 0.0 | 4.0 | 2.0 | 7.0 | 8.0 | 4.0 |  | 5.0 | 4.0 | 4.0 | 2.0 | 0.0 |

TABLE II-continued
PRE-EMERGENCE TESTS - RATES IN KG/HA

| Compound | RATE | BARNY ARDGR | FOXTAIL SP | P NUT SEDGE | WILD OATS | QUACK GRASS | FLD B INDWD | MATRI CARIA | MRNGL RY SP | RAGWE ED | VELVE TLEAF | H BAR LY MA | CORN FIELD | COTTO N | RICE, NATO | SOYBE AN BR | S WHE AT ER |
|---|---|---|---|---|---|---|---|---|---|---|---|---|---|---|---|---|---|
| 2-imidazolin-2-yl)-thieno[3,2-b]pyridine-6-carboxylic acid | .125 | 4.0 | 2.0 | 2.0 | 1.0 | 0.0 | 0.0 | 1.0 | 6.0 | 6.0 | 2.0 | | 6.0 | 3.0 | 3.0 | 2.0 | 0.0 |
| | .063 | 2.0 | 0.0 | 1.0 | 0.0 | 0.0 | 0.0 | 0.0 | 5.0 | 0.0 | 0.0 | | 0.0 | 2.0 | 2.0 | 0.0 | 0.0 |
| | .032 | 0.0 | 0.0 | 0.0 | 0.0 | 0.0 | 0.0 | 0.0 | 0.0 | 0.0 | 0.0 | | 0.0 | 2.0 | 2.0 | 0.0 | 0.0 |
| | .016 | 0.0 | 0.0 | 0.0 | 0.0 | 0.0 | 0.0 | 0.0 | 0.0 | 0.0 | 0.0 | | 0.0 | 2.0 | 2.0 | 0.0 | 0.0 |
| 3-Bromo-6-(4-isopropyl-4-methyl-5-oxo-2-imidazolin-2-yl)-thieno[2,3-b]pyridine-5-carboxylic acid | .500 | 9.0 | 9.0 | 8.0 | 9.0 | 9.0 | 9.0 | 9.0 | 0.0 | 9.0 | 9.0 | | 9.0 | 9.0 | 9.0 | 2.0 | 9.0 |
| | .250 | 9.0 | 9.0 | 7.0 | 9.0 | 7.0 | 9.0 | 9.0 | 0.0 | 8.0 | 8.0 | | 9.0 | 9.0 | 9.0 | 3.0 | 6.0 |
| | .125 | 8.0 | 7.0 | 7.0 | 9.0 | 8.0 | 9.0 | 8.0 | 0.0 | 8.0 | 7.0 | | 9.0 | 9.0 | 6.0 | | 8.0 |
| | .063 | 7.0 | 2.0 | 4.0 | 8.0 | 0.0 | 9.0 | 8.0 | 0.0 | 8.0 | 3.0 | | 8.0 | 9.0 | 6.0 | 2.0 | 8.0 |
| | .032 | 7.0 | 2.0 | 0.0 | 8.0 | 0.0 | 9.0 | 6.0 | 7.0 | 8.0 | 4.0 | | 7.0 | 7.0 | 4.0 | 2.0 | 6.0 |
| | .016 | 2.0 | 0.0 | 0.0 | 6.0 | 0.0 | 9.0 | | 2.0 | 4.0 | 0.0 | | 6.0 | | 3.0 | 2.0 | 4.0 |
| 6-(4-isopropyl-4-methyl-5-oxo-2-imidazolin-2-yl)-2-methyl-thieno[2,3-b]pyridine-5-carboxylic acid | .500 | 9.0 | 9.0 | 8.0 | 9.0 | 9.0 | 9.0 | 8.0 | 9.0 | 8.0 | 9.0 | | 9.0 | 9.0 | 8.0 | 4.0 | 9.0 |
| | .250 | 9.0 | 9.0 | 8.0 | 9.0 | 9.0 | 9.0 | 8.0 | 9.0 | 8.0 | 8.0 | | 9.0 | 9.0 | 8.0 | | 6.0 |
| | .125 | 8.0 | 6.0 | 8.0 | 7.0 | 9.0 | 9.0 | 8.0 | 9.0 | 8.0 | 8.0 | | 9.0 | 9.0 | 9.0 | | 7.0 |
| | .063 | 6.0 | | 4.0 | 3.0 | 9.0 | 4.0 | 8.0 | 9.0 | 2.0 | 4.0 | | 8.0 | 9.0 | 8.0 | | 6.0 |
| | .032 | 3.0 | 2.0 | 4.0 | 2.0 | 9.0 | 4.0 | 3.0 | 6.0 | 2.0 | 4.0 | | 7.0 | 7.0 | 6.0 | 4.0 | 3.0 |
| | .016 | 4.0 | 6.0 | 3.0 | 2.0 | 6.0 | 2.0 | 2.0 | | 0.0 | 4.0 | | 5.0 | | 3.0 | 2.0 | 3.0 |
| Furfuryl 5-(4-isopropyl-4-methyl-5-oxo-2-imidazolin-2-yl)-thieno[3,2-b]pyridine-6-carboxylate | .500 | 9.0 | 9.0 | 8.0 | 9.0 | 9.0 | 9.0 | 8.0 | 9.0 | 9.0 | 9.0 | | 9.0 | 9.0 | 9.0 | 2.0 | 7.0 |
| | .250 | 9.0 | 9.0 | 9.0 | 9.0 | 9.0 | 7.0 | 8.0 | 9.0 | 9.0 | 7.0 | | 7.0 | 9.0 | 9.0 | 2.0 | 7.0 |
| | .125 | 8.0 | 9.0 | 9.0 | 9.0 | 7.0 | | 7.0 | 7.0 | 9.0 | 7.0 | | 7.0 | 9.0 | 8.0 | 2.0 | 3.0 |
| | .063 | 8.0 | 6.0 | 8.0 | 8.0 | 6.0 | 2.0 | 7.0 | | 8.0 | 7.0 | | 7.0 | 9.0 | 8.0 | | 2.0 |
| | .032 | 7.0 | 6.0 | 8.0 | 6.0 | 6.0 | 2.0 | 6.0 | | 8.0 | 6.0 | | 4.0 | 9.0 | 6.0 | | 2.0 |
| | .016 | 5.0 | 5.0 | 2.0 | 2.0 | 3.0 | 0.0 | 2.0 | | 2.0 | 4.0 | | 2.0 | 9.0 | 6.0 | | 2.0 |
| 3-Chloro-6-(4-isopropyl-4-methyl-5-oxo-2-imidazolin-2-yl)-thieno[2,3-b]pyridine-5-carboxylic acid | .500 | 9.0 | 9.0 | 8.0 | 9.0 | 9.0 | 9.0 | 9.0 | 9.0 | 9.0 | 9.0 | | 9.0 | 9.0 | 9.0 | 2.0 | 8.0 |
| | .250 | 9.0 | 9.0 | 6.0 | 9.0 | 9.0 | 9.0 | 8.0 | 9.0 | 9.0 | 7.0 | | 9.0 | 9.0 | 9.0 | 4.0 | 8.0 |
| | .125 | 8.0 | 7.0 | 5.0 | 9.0 | 7.0 | 9.0 | 8.0 | 9.0 | 9.0 | 7.0 | | 8.0 | 9.0 | 9.0 | 3.0 | 7.0 |
| | .063 | 7.0 | 7.0 | 4.0 | 9.0 | 4.0 | 7.0 | 8.0 | 6.0 | 8.0 | 3.0 | | 8.0 | 9.0 | 9.0 | 2.0 | 7.0 |
| | .032 | 6.0 | 7.0 | 3.0 | 9.0 | 3.0 | 6.0 | 6.0 | 0.0 | 8.0 | 3.0 | | 8.0 | 9.0 | 6.0 | | 6.0 |
| | .016 | 5.0 | 2.0 | 0.0 | 9.0 | 2.0 | 3.0 | 4.0 | | 8.0 | 2.0 | | 5.0 | 9.0 | 7.0 | 2.0 | 2.0 |
| 6-(4-isopropyl-4-methyl-5-oxo-2-imidazolin-2-yl)-furo[2,3-b]pyridine-5-carboxylic acid | .250 | 9.0 | 9.0 | 9.0 | 9.0 | 9.0 | 9.0 | 9.0 | 9.0 | 9.0 | 9.0 | | 9.0 | 9.0 | 9.0 | 0.0 | 9.0 |
| | .125 | 9.0 | 9.0 | 9.0 | 9.0 | 9.0 | 9.0 | 9.0 | | 9.0 | 9.0 | | 9.0 | 9.0 | 9.0 | 7.0 | 9.0 |
| | .063 | 9.0 | 9.0 | 9.0 | 8.0 | 9.0 | 9.0 | 9.0 | 9.0 | 8.0 | 9.0 | | 9.0 | 9.0 | 9.0 | 6.0 | 8.0 |
| | .032 | 9.0 | 9.0 | 9.0 | 9.0 | 9.0 | 9.0 | 9.0 | 8.0 | 8.0 | 9.0 | | 9.0 | 9.0 | 9.0 | 7.0 | 8.0 |
| | .016 | 9.0 | 9.0 | 9.0 | 8.0 | 7.0 | 9.0 | 7.0 | 8.0 | 8.0 | 9.0 | | 9.0 | 9.0 | 6.0 | 7.0 | 7.0 |
| 2,3-dihydro-6-(4-isopropyl-4-methyl-5-oxo-2-imidazolin-2-yl)-furo[2,3-b]pyridine-5-carboxylic acid | .500 | 9.0 | 9.0 | 9.0 | 9.0 | 9.0 | 9.0 | 9.0 | 9.0 | 9.0 | 9.0 | | 9.0 | 9.0 | 9.0 | 7.0 | 9.0 |
| | .250 | 9.0 | 9.0 | 9.0 | 9.0 | 9.0 | 9.0 | 9.0 | 9.0 | 9.0 | 8.0 | | 9.0 | 9.0 | 9.0 | 5.0 | 8.0 |
| | .125 | 9.0 | 9.0 | 9.0 | 9.0 | 9.0 | 9.0 | 6.0 | 8.0 | 7.0 | 8.0 | | 8.0 | 9.0 | 9.0 | 4.0 | 8.0 |
| | .063 | 9.0 | 9.0 | 9.0 | 8.0 | 9.0 | 9.0 | 0.0 | 5.0 | 8.0 | 8.0 | | 8.0 | 9.0 | 8.0 | 3.0 | 7.0 |
| | .032 | 6.0 | 6.0 | 9.0 | 9.0 | 8.0 | 9.0 | 0.0 | 5.0 | 0.0 | 8.0 | | 8.0 | 9.0 | 8.0 | | 6.0 |
| | .016 | 9.0 | 4.0 | 9.0 | 7.0 | 5.0 | 7.0 | 0.0 | | 0.0 | 6.0 | | 5.0 | 9.0 | 6.0 | | 0.0 |

EXAMPLE 60

Plant Growth Regulant Evaluation of the Compounds

The plant growth regulant activity of the compounds of the present invention is demonstrated by the following test, wherein barley (*Hordeum vulgare*) is treated with a test compound dissolved in aqueous acetone. In the test, the compound dissolved acetone/water mixtures 50/50 containing 0.25% by volume of Colloidal Multi-film X-77 surfactant (alkylarylpolyoxy ethyleneglycols, free fatty acids and isopropanol) of Colloidal Products Corporation (Petaluma, Calif.) in sufficient quantities to provide the equivalent of about 0.00625 kg to 0.10 kg per hectare of active compound when applied to the plants when the first node is detectable (Zadok 30). After spraying, the plants are placed on greenhouse benches and are cared for in the usual manner, commensurate with conventional greenhouse practices. From 11 to 12 weeks after treatment the plants are measured and harvested. The heads are removed and dried for 48 hours at 85° to 90° C. and weights recorded. The data obtained are recorded in Table III below.

TABLE III

Plant growth regulant activity test

| Compound | Rate kg/ha | Replicate | Total Head Dry wt/g | % Increase Head wt |
|---|---|---|---|---|
| Untreated control | — | 1 | 56.7 | — |
|  | — | 2 | 55.9 |  |
|  | — | 3 | 60.6 |  |
|  |  | Average | 57.7 |  |
| Furfuryl 6-(4-iso- | 0.10 | 1 | 64.6 | 14.9 |
| propyl-4-methyl-5- |  | 2 | 68.2 |  |
| oxo-2-imidazolin- |  | 3 | 66.1 |  |
| 2-yl)-thieno[2,3-b]- |  | Average | 66.3 |  |
| pyridine-5-carboxylate |  |  |  |  |
|  | 0.05 | 1 | 66.6 | 26.1 |
|  |  | 2 | 74.1 |  |
|  |  | 3 | 77.7 |  |
|  |  | Average | 72.8 |  |
|  | 0.025 | 1 | 52.9 | 10.9 |
|  |  | 2 | 70.6 |  |
|  |  | 3 | 68.7 |  |
|  |  | Average | 64.0 |  |
|  | 0.0125 | 1 | 64.9 | 23.0 |
|  |  | 2 | 72.6 |  |
|  |  | 3 | 75.5 |  |
|  |  | Average | 71.0 |  |
|  | 0.00625 | 1 | 58.6 | 12.5 |
|  |  | 2 | 67.5 |  |
|  |  | 3 | 68.4 |  |
|  |  | Average | 64.9 |  |

What is claimed is:

1. A compound having the structure:

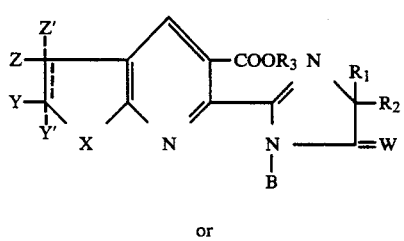

(a)

or

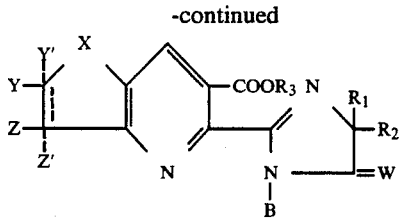

(b)

wherein ═ represents a single or a double bond; $R_1$ is $C_1$–$C_4$ alkyl; $R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl; $R_3$ is hydrogen; $C_1$–$C_4$ alkyl, which may be interrupted by one O or S and is optionally substituted with one of the following groups: furyl, phenyl, mono or di halophenyl, $C_1$–$C_4$ mono or di alkylphenyl, $C_1$–$C_4$ mono or di alkoxy phenyl or mono nitrophenyl; $C_3$–$C_6$ alkenyl optionally substituted with one or two halogens; $C_3$–$C_6$ alkynyl; or a cation of alkali metals, alkaline earth metals, manganese, copper, iron, ammonium or organic ammonium; B is H, $COR_4$ or $SO_2R_5$, provided that when B is $COR_4$, $R_3$ cannot be hydrogen or a salt-forming cation; $R_4$ is $C_1$–$C_4$ alkyl, chloromethyl or phenyl optionally substituted with one chloro, one nitro, one methyl, or one methoxy group; $R_5$ is $C_1$–$C_5$ alkyl or phenyl optionally substituted with one methyl group, chloro or nitro; W is O or S; X is O, S, or, where ═ is a single bond, X is S═O; Y and Y', Z and Z' are hydrogen, halogen, $C_1$–$C_6$ alkyl, $C_1$–$C_6$ alkoxy, $C_1$–$C_6$ alkanoyloxy, $C_1$–$C_4$ alkylthio, phenoxy; methyl, optionally substituted with any combination of from one to three fluorine, chlorine or bromine atoms or $C_2$–$C_4$ alkyl, optionally substituted with any combination of from one to five fluorine, chlorine and bromine atoms, methoxy, optionally substituted with any combination of from one to three fluorine, chlorine or bromine atoms or $C_2$–$C_4$ alkoxy, optionally substituted with any combination of from one to five fluorine, chlorine or bromine atoms; nitro, cyano, $C_1$–$C_4$ dialkylamino or phenyl optionally substituted with one to two $C_1$–$C_4$ alkyl, $C_1$–$C_4$ alkoxy, halogen, or any combination of two of these groups with the proviso that when Y and Z are the same group they are H, halogen, alkyl or alkoxy, and when Y and Y' or Z and Z' are the same group they are hydrogen or alkyl; and, when taken together, Y and Z may form a ring in which YZ are represented by the structure —$(CH_2)_n$—, where n is an integer of 3 or 4, or

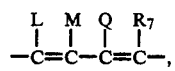

where L, M, Q and $R_7$ each represent hydrogen, halogen, $C_1$–$C_4$ alkyl or $C_1$–$C_4$ alkoxy, with the proviso that only one of L, M, Q or $R_7$, may represent a substituent other than hydrogen, halogen, $C_1$–$C_4$ alkyl or $C_1$–$C_4$ alkoxy; the pyridine N-oxides thereof; when $R_1$ and $R_2$ are not the same, the optical isomers thereof; and, except when $R_3$ is a salt-forming cation, the acid addition salts thereof.

2. A compound according to claim 1 wherein the $R_3$ $C_1$–$C_4$ alkyl, may be optionally substituted with one of the following groups: furyl, phenyl, halophenyl; $C_1$–$C_4$ alkylphenyl, $C_1$–$C_4$ alkoxyphenyl or nitrophenyl; the $R_3$ cation is hydrogen, propynyl, furfuryl, methyl or a cation of alkali metals, alkaline earth metals, ammonium or mono, di, tri, or tetra $C_1$-$C_{22}$ alkylammonium provided that no more than one group may be $C_{19}$-$C_{22}$ alkyl, no more than two groups may be $C_{13}$-$C_{18}$ alkyl, and no more than three groups may be $C_5$-$C_{12}$ alkyl; Y and Y', Z and Z' are hydrogen, halogen, $C_1$-$C_6$ alkyl, $C_1$-$C_6$ alkoxy, $C_1$-$C_6$ alkanoyloxy, $C_1$-$C_4$ haloalkyl, $C_1$-$C_4$ haloalkoxy, nitro, $C_1$-$C_4$ dialkylamino or phenyl with the proviso that when Y and Z are the same group they are H, halogen, alkyl or alkoxy, and that when $\equiv\equiv\equiv$ is a single bond, Y, Y', Z and Z' are hydrogen, alkyl, alkoxy or halogen and when Y and Y' or Z and Z' are the same group they are hydrogen or alkyl; and, when taken together, Y and Z may form a ring in which YZ are represented by the structure $-(CH_2)_n-$, where n is an integer of 3 or 4, or $-CH=CH-CH=CH-$.

3. A compound according to claim 2 having the structure:

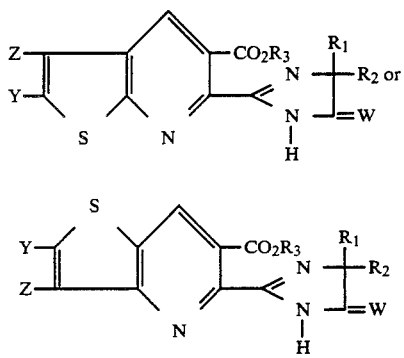

wherein Y and Z are hydrogen, methyl, ethyl, chlorine, bromine, methoxy or phenyl; $R_3$ is a cation of alkali metals, alkaline earth metals, ammonium or mono, di, tri or tetra $C_1$-$C_{22}$ alkylammonium provided that no more than one group may be $C_{19}$-$C_{22}$ alkyl, no more than two groups may be $C_{13}$-$C_{18}$ alkyl, and no more than three groups may be $C_5$-$C_{12}$ alkyl; $R_1$ and $R_2$ are methyl, ethyl, isopropyl, and when taken together form a cyclohexyl or 2-methylcyclohexyl ring; W is O or S, and when $R_1$ and $R_2$ are not the same, the optical isomers thereof.

4. A compound according to claim 2 having the structure:

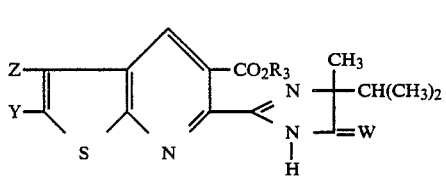

wherein Y is hydrogen or methyl; Z is hydrogen, chlorine or bromine $R_3$ is hydrogen, propynyl, furfuryl or a sodium, ammonium or mono, di, tri or tetra $C_1$-$C_{22}$ alkylammonium cation provided that no more than one group may be $C_{19}$-$C_{22}$ alkyl, no more than two groups may be $C_{13}$-$C_{18}$ alkyl, and no more than three groups may be $C_5$-$C_{12}$ alkyl; W is O or S, and the optical isomers thereof.

5. A compound according to claim 2 having the structure:

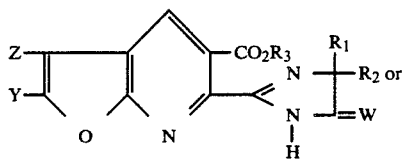

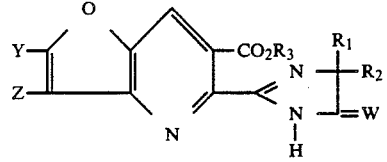

wherein Y and Z are hydrogen, methyl, ethyl, chlorine, bromine, methoxy or phenyl; $R_3$ is hydrogen, propynyl, furfuryl methyl or a cation of alkali metals, alkaline earth metals, ammonium or mono, di, tri or tetra $C_1$-$C_{22}$ alkylammonium provided that no more than one group may be $C_{19}$-$C_{22}$ alkyl, no more than two groups may be $C_{13}$-$C_{18}$ alkyl, and no more than three groups may be $C_5$-$C_{12}$ alkyl; $R_1$ and $R_2$ are methyl, ethyl, isopropyl, or when taken together form a cyclohexyl or 2-methylcyclohexyl ring, W is O or S, and when $R_1$ and $R_2$ are not the same, the optical isomers thereof.

6. A compound according to claim 5 having the structure:

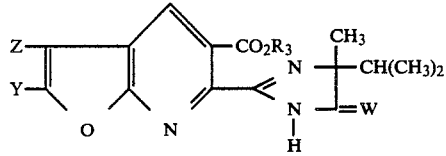

wherein Y is hydrogen or methyl; Z is hydrogen, chlorine or bromine; $R_3$ is hydrogen, furfuryl, or a sodium ammonium or mono, tri or tetra $C_1$-$C_{22}$ alkylammonium cation provided that no more than one group may be $C_{19}$-$C_{22}$ alkyl, no more than two groups may be $C_{13}$-$C_{18}$ alkyl, and no more than three groups may be $C_5$-$C_{12}$ alkyl; W is O or S; and the optical isomers thereof.

7. A compound according to claim 2 having the structure:

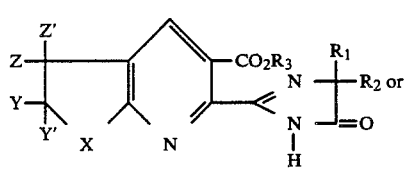

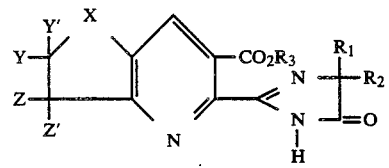

wherein X is oxygen, sulfur, or S=O; Y and Z are hydrogen, methoxy, methyl, or chlorine, with the proviso that one of Y and Z is hydrogen; $R_3$ is hydrogen, furfuryl, propynyl, methyl or a cation of alkali metals, alkaline earth metals, ammonium or mono, di, tri or tetra $C_1$-$C_{22}$ alkylammonium provided that no more than one group may be $C_{19}$-$C_{22}$ alkyl, no more than two groups may be $C_{13}$-$C_{18}$ alkyl, and no more than three groups may be $C_5$-$C_{12}$ alkyl; $R_1$ and $R_2$ are methyl, ethyl, isopropyl, or when taken together form a cyclohexyl or 2-methylcyclohexyl ring, and when $R_1$ and $R_2$ are not the same, the optical isomers thereof.

8. The compound according to claim 3, 2-chloro-5-(4-isopropyl-4-methyl-5-oxo-2-imidazolin-2-yl)-thieno[3,2-b]pyridine-6-carboxylic acid.

9. The compound according to claim 3, furfuryl 5-(4-isopropyl-4-methyl-5-oxo-2-imidazolin-2-yl)-thieno[3,2-b]pyridine-6-carboxylic acid.

10. The compound according to claim 4, furfuryl 6-(4-isopropyl-4-methyl-5-oxo-2-imidazolin-2-yl)-thieno-[2,3-b]pyridine-5-carboxylate.

11. A compound according to claim 4, 6-(4-isopropyl-4-methyl-5-oxo-2-imidazolin-2-yl)-thieno[2,3-b]pyridine-5-carboxylic acid.

12. A compound according to claim 4, 6-(4-isopropyl-4-methyl-5-oxo-2-imidazolin-2-yl)-2-methylthieno[2,3-b]pyridine-5-carboxylic acid.

13. The compound according to claim 4, propynyl-6-(4-isopropyl-4-methyl-5-oxo-2-imidazolin-2-yl)-thieno[2,3-b]pyridine-5-carboxylate.

14. The compound according to claim 4, 3-bromo-6-(4-isopropyl-4-methyl-5-oxo-2-imidazolin-2-yl)thieno-[2,3-b]pyridine-5-carboxylic acid.

15. The compound according to claim 4, 6-(4-isopropyl-4-methyl-5-thioxo-2-imidazolin-2-yl)-thieno[2,3-b]pyridine-5-carboxylic acid.

16. The compound according to claim 5, 5-(4-isopropyl-4-methyl-5-oxo-2-imidazolin-2-yl)furo[3,2-b]pyridine-6-carboxylic acid.

17. The compound according to claim 5, 6-(4-isopropyl-4-methyl-5-thioxo-2-imidazolin-2-yl)-furo[2,3-b]pyridine-5-carboxylic acid.

18. The compound according to claim 6, 6-(4-isopropyl-4-methyl-5-oxo-2-imidazolin-2-yl)furo[2,3-b]pyridine-5-carboxylic acid.

19. The compound according to claim 6, 3-chloro-6-(4-isopropyl-4-methyl-5-oxo-2-imidazolin-2-yl)furo[2,3-b]pyridine-5-carboxylic acid.

20. The compound according to claim 6, 3-bromo-6-(4-isopropyl-4-methyl-5-oxo-2-imidazolin-2-yl)-furo[2,3-b]pyridine-5-carboxylic acid.

21. The compound according to claim 6, (+)6-(4-isopropyl-4-methyl-5-oxo-2-imidazolin-2-yl)furo[2,3-b]pyridine-5-carboxylic acid.

22. The compound according to claim 6, furfuryl 6-(4-isopropyl-4-methyl-5-oxo-2-imidazolin-2-yl)-furo[2,3-b]pyridine-5-carboxylate.

23. The compound according to claim 6, sodium 6-(4-isopropyl-4-methyl-5-oxo-2-imidazolin-2-yl)furo[2,3-b]pyridine-5-carboxylate.

24. The compound according to claim 7, 2,3-dihydro-6-(4-isopropyl-4-methyl-5-oxo-2-imidazolin-2-yl)-furo[2,3-b]-pyridine-5-carboxylic acid.

25. The compound according to claim 7, 2,3-dihydro-5-(4-isopropyl-4-methyl-5-oxo-2-imidazolin-2-yl)-furo[3,2-b]pyridine-6-carboxylic acid.

26. A method for the control of monocotyledonous and dicotyledonous annual, perennial and aquatic plant species comprising: applying to the foliage of said plants or to soil or water containing seeds or other propagating organs thereof, a herbicidally effective amount of a compound having a structure:

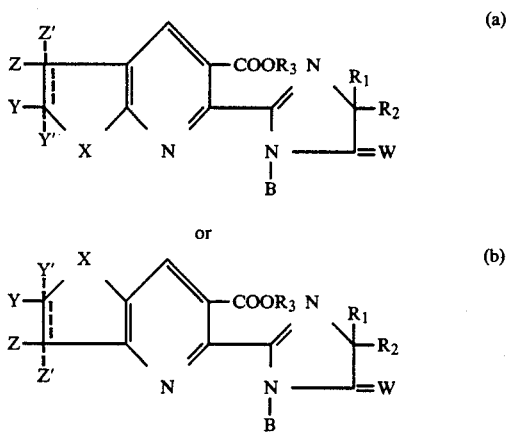

wherein $\mathrel{\overline{\overline{\phantom{xx}}}}$ represents a single or a double bond; $R_1$ is $C_1$-$C_4$ alkyl; $R_2$ is $C_1$-$C_4$ alkyl or $C_3$-$C_6$ cycloalkyl; and when $R_1$ and $R_2$ are taken together with the carbon to which they are attached they may represent $C_3$-$C_6$ cycloalkyl optionally substituted with methyl; $R_3$ is hydrogen; $C_1$-$C_4$ alkyl, which may be interrupted by one O or S and is optionally substituted with one of the following groups: furyl, phenyl, mono or di halophenyl, $C_1$-$C_4$ mono or di alkylphenyl, $C_1$-$C_4$ mono or di alkoxyphenyl or mono nitrophenyl; $C_3$-$C_6$ alkenyl optionally substituted with one or two halogens; $C_3$-$C_6$ alkynyl; or a cation of alkali metals, alkaline earth metals, manganese, copper, iron, ammonium or organic ammonium; B is H, $COR_4$ or $SO_2R_5$, provided that when B is $COR_4$, $R_3$ cannot be hydrogen or a salt-forming cation; $R_4$ is $C_1$-$C_4$ alkyl, chloromethyl or phenyl optionally substituted with one chloro, one nitro, one methyl, or one methoxy group; $R_5$ is $C_1$-$C_5$ alkyl or phenyl optionally substituted with one methyl group, chloro or nitro; W is O or S; X is O, S, or where $\mathrel{\overline{\overline{\phantom{xx}}}}$ is a single bond, X is S=O; Y and Y', Z and Z' are hydrogen, halogen, $C_1$-$C_6$ alkyl, $C_1$-$C_6$ alkoxy, $C_1$-$C_6$ alkanoyloxy, $C_1$-$C_4$ alkylthio, phenoxy; methyl, optionally substituted with any combination of from one to three fluorine, chlorine or bromine atoms or $C_2$-$C_4$ alkyl, optionally substituted with any combination of from one to five fluorine, chlorine and bromine atoms, methoxy, optionally substituted with any combination of from one to three fluorine, chlorine or bromine atoms or $C_2$-$C_4$ alkoxy, optionally substituted with any combination of from one to five fluorine, chlorine or bromine atoms; nitro, cyano, $C_1$-$C_4$ dialkylamino or phenyl optionally substituted with one or two $C_1$-$C_4$ alkyl, $C_1$-$C_4$ alkoxy, halogen, or any combination of two of these groups with the proviso that when Y and Z are the same group they are H, halogen, alkyl or alkoxy, and when Y and Y' or Z and Z' are the same group they are hydrogen or alkyl; and, when taken together, Y and Z may form a ring in which YZ are represented by the structure: —($CH_2$)$_n$—, where n is an integer of 3 or 4, or

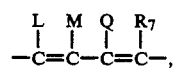

where L, M, Q and $R_7$ each represent hydrogen, halogen, $C_1$-$C_4$ alkyl or $C_1$-$C_4$ alkoxy, with the proviso that only one of L, M, Q or $R_7$, may represent a substituent other than hydrogen, halogen, $C_1$-$C_4$ alkyl or $C_1$-$C_4$ alkoxy; the pyridine N-oxides thereof; and when $R_1$ and $R_2$ are not the same, the optical isomers thereof; and, except when $R_3$ is a salt-forming cation, the acid addition salts thereof.

27. A method according to claim 26 wherein the $R_3$ $C_1$–$C_4$ alkyl, may be optionally substituted with one of the following groups: furyl, phenyl, halophenyl, $C_1$–$C_4$ alkylphenyl, $C_1$–$C_4$ alkoxyphenyl or nitrophenyl; the $R_3$ cation is hydrogen, propynyl, furfuryl, methyl or a cation of alkali metals, alkaline earth metals, ammonium or mono, di, tri, or tetra $C_1$–$C_{22}$ akylammonium provided that no more than one group may be $C_{19}$–$C_{22}$ alkyl, no more than two groups may be $C_{13}$–$C_{18}$ alkyl, and no more than three groups may be $C_5$–$C_{12}$ alkyl; Y and Y', Z and Z' are hydrogen, halogen, $C_1$–$C_6$ alkyl; $C_1$–$C_6$ alkoxy, $C_1$–$C_6$ alkanoyloxy, $C_1$–$C_4$ haloalkyl, $C_1$–$C_4$ haloalkoxy, nitro, $C_1$–$C_4$ dialkylamino or phenyl with the proviso that when Y and Z are the same group they are H, halogen, alkyl or alkoxy, and that when is a single bond, Y, Y', Z and Z' are hydrogen, alkyl, alkoxy or halogen and when Y and Y' or Z and Z' are the same group they are hydrogen or alkyl; and, when taken together, Y and Z may form a ring in which YZ are represented by the structure —$(CH_2)_n$—, where n is an integer of 3 or 4, or —CH=CH—CH=CH—.

28. A method according to claim 27 wherein said compound has the structure:

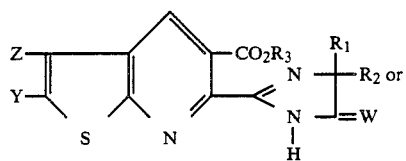

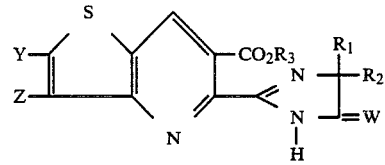

wherein Y and Z are hydrogen, methyl, ethyl, chlorine, bromine, methoxy or phenyl; $R_3$ is hydrogen, propynyl, furfuryl, methyl or a cation of alkali metals, alkaline earth metals, ammonium or mono, di, tri, or tetra $C_1$–$C_{22}$ alkylammonium provided that no more than one group may be $C_{19}$–$C_{22}$ alkyl, no more than two groups may be $C_{13}$–$C_{18}$ alkyl, and no more than three groups may be $C_5$–$C_{12}$ alkyl; $R_1$ and $R_2$ are methyl, ethyl, isopropyl, or when taken together form a cyclohexyl or 2-methylcyclohexyl ring; W is O or S, and when $R_1$ and $R_2$ are not the same, the optical isomers thereof.

29. A method according to claim 27 wherein said compound has the structure:

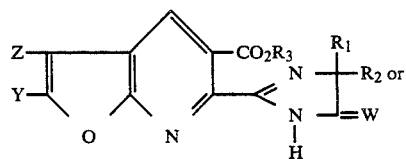

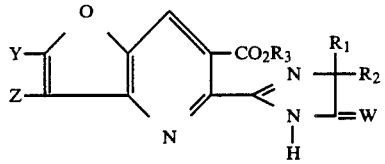

wherein Y and Z are hydrogen, methyl, ethyl, chlorine, bromine, methoxy or phenyl; $R_3$ is hydrogen, propynyl, furfuryl, methyl or a cation of alkali metals, alkaline earth metals, ammonium or mono, di, tri, or tetra $C_1$–$C_{22}$ alkylammonium provided that no more than one group may be $C_{19}$–$C_{22}$ alkyl, no more than two groups may be $C_{13}$–$C_{18}$ alkyl, and no more than three groups may be $C_5$–$C_{12}$ alkyl; $R_1$ and $R_2$ are methyl, ethyl, isopropyl, or when taken together form a cyclohexyl or 2-methylcyclohexyl ring; W is O or S, and when $R_1$ and $R_2$ are not the same, the optical isomers thereof.

30. A method according to claim 27 wherein said compound has the structure:

wherein X is oxygen, sulfur, or S=O; Y and Z are hydrogen, methoxy, methyl, or chlorine, with the proviso that one of Y and Z is hydrogen; $R_3$ is hydrogen, furfuryl, propynyl, methyl or a cation of alkali metals, alkaline earth metals, ammonium or mono, di, tri or tetra $C_1$–$C_{22}$ alkylammonium provided that no more than one group may be $C_{19}$–$C_{22}$ alkyl, no more than two groups may be $C_{13}$–$C_{18}$ alkyl, and no more than three groups may be $C_5$–$C_{12}$ alkyl; $R_1$ and $R_2$ are methyl, ethyl, isopropyl, or when taken together form a cyclohexyl or 2-methylcyclohexyl ring, and when $R_1$ and $R_2$ are not the same, the optical isomers thereof.

31. A method for regulating the growth of plants and increasing the yield of gramineacous and liguminous crops, comprising applying to the foliage of said plants an effective amount of a compound selected from the compounds having the structure:

and

-continued

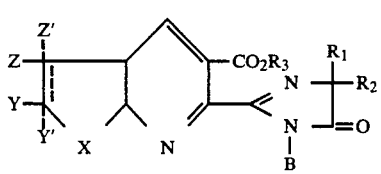

wherein $\doteq$ represents a single or a double bond; $R_1$ is $C_1$–$C_4$ alkyl; $R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl; $R_3$ is hydrogen; $C_1$–$C_4$ alkyl, which may be interrupted by one O or S and is optionally substituted with one of the following groups: furyl, phenyl, mono or di halophenyl, $C_1$–$C_4$ mono or di alkylphenyl, $C_1$–$C_4$ mono or di alkoxy phenyl or mono nitrophenyl; $C_3$–$C_6$ alkenyl optionally substituted with one or two halogens; $C_3$–$C_6$ alkynyl; or a cation of alkali metals, alkaline earth metals, manganese, copper, iron, ammonium or organic ammonium; B is H, COR$_4$ or SO$_2$R$_5$, provided that when B is COR$_4$, $R_3$ cannot be hydrogen or a salt-forming cation; $R_4$ is $C_1$–$C_4$ alkyl, chloromethyl or phenyl optionally substituted with one chloro, one nitro, one methyl, or one methoxy group; $R_5$ is $C_1$–$C_5$ alkyl or phenyl optionally substituted with one methyl group, chloro or nitro; W is O or S; X is O, S, or, where $\doteq$ is a single bond, X is S=O; Y and Y', Z and Z' are hydrogen, halogen, $C_1$–$C_6$ alkyl, $C_1$–$C_6$ alkoxy, $C_1$–$C_6$ alkanoyloxy, $C_1$–$C_4$ alkylthio, phenoxy; methyl, optionally substituted with any combination of from one to three fluorine, chlorine or bromine atoms or $C_2$–$C_4$ alkyl, optionally substituted with any combination of from one to five fluorine, chlorine and bromine atoms, methoxy, optionally substituted with any combination of from one to three fluorine, chlorine or bromine atoms or $C_2$–$C_4$ alkoxy, optionally substituted with any combination from one to five fluorine, chlorine or bromine atoms; nitro, cyano, $C_1$–$C_4$ dialkylamino or phenyl optionally substituted with one or two $C_1$–$C_4$ alkyl, $C_1$–$C_4$ alkoxy, halogen, or any combination of two of these groups with the proviso that when Y and Z are the same group they are H, halogen, alkyl or alkoxy, and when Y and Y' or Z and Z' are the same group they are hydrogen or alkyl; and, when taken together, Y and Z may form a ring in which YZ are represented by the structure —$(CH_2)_n$—, where n is an integer of 3 or 4, or

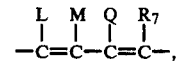

where L, M, Q and $R_7$ each represent hydrogen, halogen, $C_1$–$C_4$ alkyl or $C_1$–$C_4$ alkoxy, with the proviso that only one of L, M, Q or $R_7$, may represent a substituent other than hydrogen, halogen, $C_1$–$C_4$ alkyl or $C_1$–$C_4$ alkoxy; the pyridine N-oxides thereof; when $R_1$ and $R_2$ are not the same, the optical isomers thereof; and, except when $R_3$ is a salt-forming cation, the acid addition salts thereof.

32. A method according to claim 31 wherein the $R_3$ $C_1$–$C_4$ alkyl, may be optionally substituted with one of the following groups: furyl, phenyl, halophenyl; $C_1$–$C_4$ alkylphenyl, $C_1$–$C_4$ alkoxyphenyl or nitrophenyl; the $R_3$ cation is hydrogen, propynyl, furfuryl, methyl or a cation of alkali metals, alkaline earth metals, ammonium or mono, di, tri, or tetra $C_1$–$C_{22}$ alkylammonium provided that no more than one group may be $C_{19}$–$C_{22}$ alkyl, no more than two groups may be $C_{13}$–$C_{18}$ alkyl, and no more than three groups may be $C_5$–$C_{12}$ alkyl; Y and Y', Z and Z' are hydrogen, halogen, $C_1$–$C_6$ alkyl, $C_1$–$C_6$ alkoxy, $C_1$–$C_6$ alkanoyloxy, $C_1$–$C_4$ haloalkyl, $C_1$–$C_4$ haloalkoxy, nitro, $C_1$–$C_4$ dialkylamino or phenyl with the proviso that when Y and Z are the same group they are H, halogen, alkyl or alkoxy, and that when $\doteq$ is a single bond, Y, Y', Z and Z' are hydrogen, alkyl, alkoxy or halogen and when Y and Y' or Z and Z' are the same group they are hydrogen or alkyl; and, when taken together, Y and Z may form a ring in which YZ are represented by the structure —$(CH_2)_n$—, where n is an integer of 3 or 4, or —CH=CH—CH=CH—.

* * * * *

UNITED STATES PATENT OFFICE
CERTIFICATE OF CORRECTION

Page 1 of 4

Patent No. 4,650,514          Dated March 17, 1987

Inventor(s) Marinus Los, David W. Ladner and Barrington Cross

It is certified that error appears in the above-identified patent and that said Letters Patent are hereby corrected as shown below:

Column 1, line 25, first formula should read as follows:

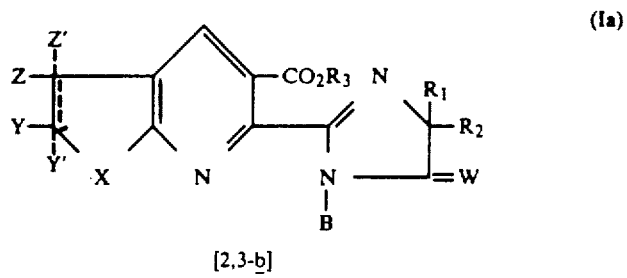

UNITED STATES PATENT OFFICE
CERTIFICATE OF CORRECTION

Patent No. 4,650,514          Dated March 17, 1987

Inventor(s) Marinus Los, David W. Ladner and Barrington Cross

It is certified that error appears in the above-identified patent and that said Letters Patent are hereby corrected as shown below:

Column 43, Example 31 replace entire formula as follows:

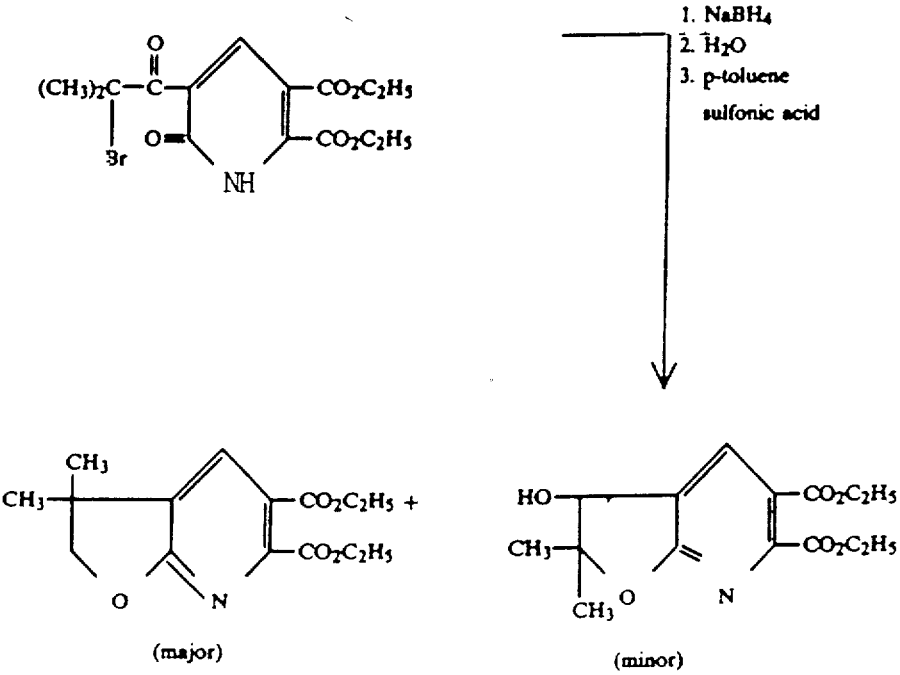

UNITED STATES PATENT OFFICE
CERTIFICATE OF CORRECTION

Patent No. 4,650,514  Dated March 17, 1987

Inventor(s) Marinus Los, David W. Ladner and Barrington Cross

It is certified that error appears in the above-identified patent and that said Letters Patent are hereby corrected as shown below:

Column 56, Example 53 first formula should read as follows:

EXAMPLE 53

Preparation of dimethyl 2,3-dihydrothieno[2,3-b]pyridine-5,6-dicarboxylate

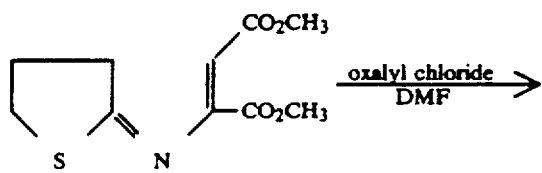

UNITED STATES PATENT OFFICE
CERTIFICATE OF CORRECTION

Patent No. 4,650,514        Dated March 17, 1987

Inventor(s) Marinus Los, David W. Ladner and Barrington Cross

It is certified that error appears in the above-identified patent and that said Letters Patent are hereby corrected as shown below:

Column 81, Claim 31, formula should be as follows:

-continued

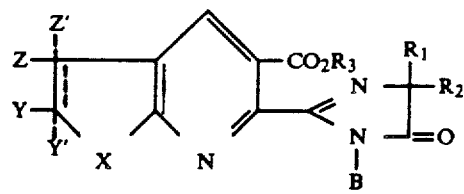

Signed and Sealed this

Eighth Day of March, 1988

Attest:

DONALD J. QUIGG

Attesting Officer        Commissioner of Patents and Trademarks